United States Patent
Lee et al.

(10) Patent No.: US 10,174,116 B2
(45) Date of Patent: Jan. 8, 2019

(54) ANTIBODY SPECIFICALLY BINDING TO HER2

(71) Applicant: ABCLON INC., Seoul (KR)

(72) Inventors: Jong-Seo Lee, Seoul (KR); Kyu-Tae Kim, Seoul (KR); Young-Ha Lee, Seoul (KR); Sook-Yeon Lee, Seoul (KR); In-Sik Hwang, Incheon (KR); Bong-Kook Ko, Seoul (KR)

(73) Assignee: ABCLON INC., Seoul (KR)

( * ) Notice: Subject to any disclaimer, the term of this patent is extended or adjusted under 35 U.S.C. 154(b) by 0 days.

(21) Appl. No.: 14/781,968

(22) PCT Filed: May 14, 2014

(86) PCT No.: PCT/KR2014/004317
§ 371 (c)(1),
(2) Date: Oct. 2, 2015

(87) PCT Pub. No.: WO2014/185704
PCT Pub. Date: Nov. 20, 2014

(65) Prior Publication Data
US 2016/0053011 A1    Feb. 25, 2016

(30) Foreign Application Priority Data
May 16, 2013 (KR) ......................... 10-2013-0055912

(51) Int. Cl.
| | |
|---|---|
| A61K 39/395 | (2006.01) |
| C07K 16/28 | (2006.01) |
| C07K 16/32 | (2006.01) |
| A61K 39/00 | (2006.01) |

(52) U.S. Cl.
CPC ...... C07K 16/2863 (2013.01); A61K 39/3955 (2013.01); A61K 39/39558 (2013.01); C07K 16/32 (2013.01); A61K 2039/507 (2013.01); C07K 2317/565 (2013.01)

(58) Field of Classification Search
None
See application file for complete search history.

(56) References Cited

U.S. PATENT DOCUMENTS

| | | |
|---|---|---|
| 8,241,630 B2 | 8/2012 | Kao et al. |
| 2012/0107270 A1 | 5/2012 | Kaspar et al. |
| 2012/0309942 A1 | 12/2012 | Li et al. |

FOREIGN PATENT DOCUMENTS

| | | |
|---|---|---|
| WO | 01/87336 A1 | 11/2001 |
| WO | 2012/143523 A1 | 10/2012 |

OTHER PUBLICATIONS

Kataja et al., Ann Oncol 2009; 20(sup 4): iv10-14 (PTO-892) (Year: 2009).*
Nelson et al., Ann. Intern Med. 2009; 151:727-737 (Year: 2009).*
Balmana et al. Ann Oncol 2009; 20(supp 4):iv19-20 (Year: 2009).*
Strome et al., The Oncologist, 2007; 12:1084-95 (Year: 2007).*
Brand et al., Anticancer Res. 2006; 26:463-70 (Year: 2006).*
Japan Patent Office, Communication dated Jul. 5, 2016, issued in Japanese counterpart application No. 2016-508909.
Ceyhan Ceran et al.; "Novel anti-HER2 monoclonal antibodies: synergy and antagonism with tumor necrosis factor-alpha" BMC Cancer ( 2012); 12:450, 16 pages total.
Werner Scheuer et al.; "Strongly Enhanced Antitumor Activity of Trastuzumab and Pertuzumab Combination Treatment on HER2-Positive Human Xenograft Tumor Models"; Cancer Res. 2009, Dec. 15, 2009; pp. 9330-9336.
Tohid Kazemi et al.; "Characterization of Novel Murine Monoclonal Anitbodies Directed Against the Extracellular Domain of Human HER2 Tyrosine Kinase Receptor," Hybridoma, vol. 30, No. 4, 2011; pp. 347-353.
Gail D. Lewis Phillips et al., "Targeting HER2-Positive Breast Cancer with Trastuzumab-DM1, an Antibody-Cytotoxic Drug Conjugate", Cancer Research, Nov. 15, 2008, pp. 9280-9290, vol. 68, No. 22.
NCBI, GenBank accession No. AA018825.1,"ze57e10.r1 Soares retina N2b4HR Homo sapiens cDNA clone Image:363114 5-, Mrna Sequence" Jan. 13, 2003; 2 pages.
NCBI, GenBank accession No. AAA70262.1, "This CDS feature is included to show the translation of the corresponding V_region. Presently translation qualifiers on V_region features are illegal, partial [Mus musculus domesticus]" Jul. 23, 1995; 1 page.
International Searching Authority, International Search Report for PCT/KR2014/004317 dated Sep. 2, 2014.
European Patent Office; Communication dated Dec. 23, 2016 in counterpart European application No. 14798440.5.

* cited by examiner

*Primary Examiner* — Sheela J. Huff
(74) *Attorney, Agent, or Firm* — Sughrue Mion, PLLC

(57) ABSTRACT

The present invention relates to HER2 (Human Epidermal Growth Factor Receptor 2) antibodies to prevent or treat cancers. The antibodies of the invention binds specifically to HER2 over-expressed in cancer cells (particularly, breast cancer and stomach cancer cells), specifically to an epitope on HER2 being different from epitope for trastuzumab. The CDR sequences of the present antibodies exhibit low similarity to CDR sequences of publicly known HER2 antibodies, addressing that the CDR sequences are unique. The antibodies of the present invention in combination with trastuzumab kill cancer cells with significantly enhanced cytotoxicity and therefore very effective in therapy of cancer (particularly, breast cancer and stomach cancer). Without wishing to be bound by theory, the enhanced efficacies of the combined therapy would address that the antibodies of the present invention bind to epitope on HER2 being different from epitope for trastuzumab, and inhibit HER2 in a cooperative manner with trastuzumab.

32 Claims, 16 Drawing Sheets
Specification includes a Sequence Listing.

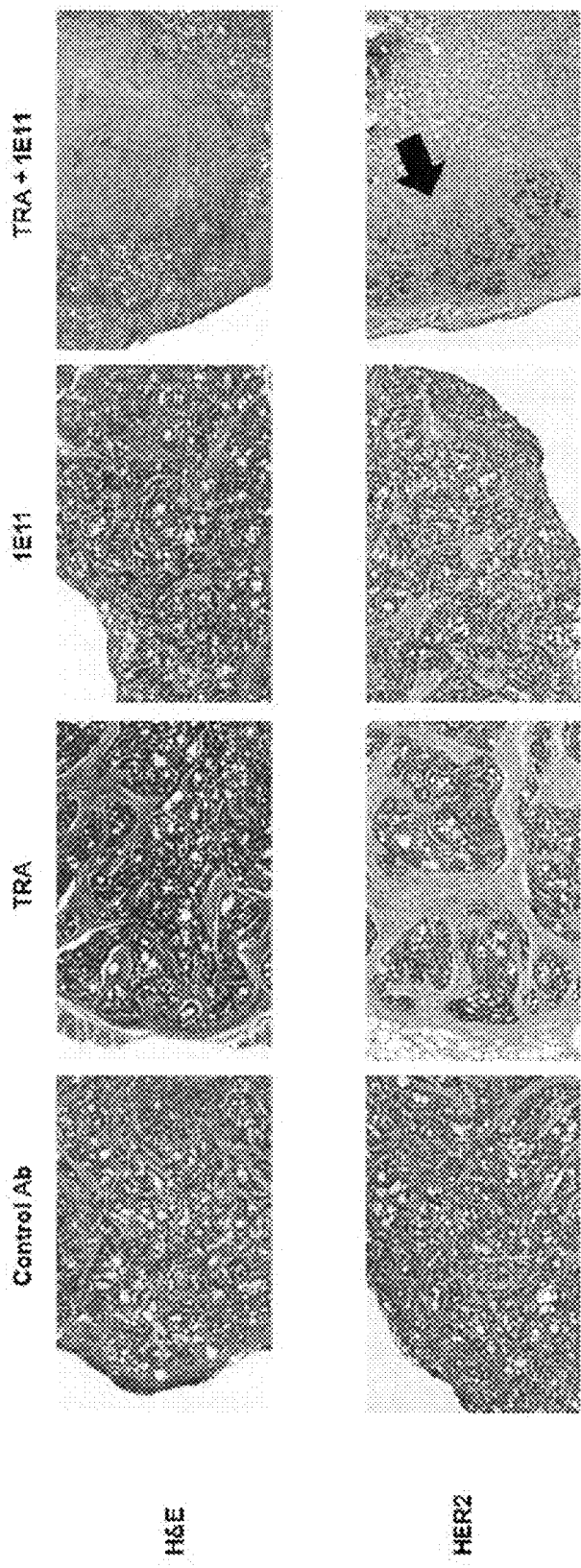

ANTIBODY SPECIFICALLY BINDING TO HER2

CROSS REFERENCE TO RELATED APPLICATIONS

This application is a National Stage of International Application No. PCT/KR2014/004317 filed May 14, 2014, claiming priority based on Korean Patent Application No. 10-2013-0055912 filed May 16, 2013, the contents of all of which are incorporated herein by reference in their entirety.

FIELD OF THE INVENTION

The present invention was made with support of the Korea Institute for the Advancement of Technology under Grant 1415118385 from Nov. 1, 2011 to Oct. 1, 2014 and management of International Cooperation Support Team of KIAT, titled as International Cooperation Technology Development Works and Innovative Epitope Discovery Platform Technology-Based Global Antibody New Drug Development, performed by AbClon, Inc.

The present invention relates to HER2 (Human Epidermal Growth Factor Receptor 2) antibodies to prevent or treat HER2-related diseases, particularly, cancers.

DESCRIPTION OF THE RELATED ART

The HER2/neu(ErbB2) gene encodes 185 kDa transmembrane glycoprotein which is one of EGFR (epidermal growth factor receptors) family members. The HER2 protein consists of an extracellular domain with 620 amino acid residues, a transmembrane domain with 23 amino acid residues and an intracellular domain having tyrosine kinase activity with 490 amino acid residues (Akiyama T, et al., Science, 232(4758):1644-1646(1986)).

In addition, HER2 antibodies with various characteristics are reported in a number of papers: Tagliabue et al., Int. J. Cancer 47:933-937 (1991); McKenzie et al., Oncogene 4:543-548 (1989); Maier et al., Cancer Res. 51:5361-5369 (1991); Bacus et al., Molecular Carcinogenesis 3:350-362 (1990); Stancovski et al., PNAS (USA) 88:8691-8695 (1991); Bacus et al., Cancer Research 52:2580-2589 (1992); Xu et al., Int. J. Cancer 53:401-408 (1993); WO94/00136; Kasprzyk et al., Cancer Research 52:2771-2776 (1992); Hancock et al., Cancer Research. 51:4575-4580 (1991); Shawver et al., Cancer Res. 54:1367-1373 (1994); Arteaga et al., Cancer Res. 54:3758-3765 (1994); Harwerth et al., J. Biol. Chem. 267:15160-15167 (1992); U.S. Pat. No. 5,783,186; Kao et al., U.S. Publ. No. 2009/0285837 (2009); Ross et al., The Oncologist 8:307-325 (2003) and Klapper et al., Oncogene 14:2099-2109 (1997).

Among HER2 antibodies, trastuzumab as the most commercially successful antibody (commercialized as Herceptin™, U.S. Pat. No. 5,821,337) has been intensively studied: Sapino, A., et al., Annals of Oncology (2007) 18: 1963-1968; Bussolati, G, et al., British Journal of Cancer (2005) 92, 1261-1267; and Glazyrin A, et al., J Histology & Cytochemistry (2007) 55(1):25-33.

Even though the trastuzumab has been commercially successful, this antibody is likely to show therapeutic efficacy in only 15% of breast cancer patients overexpressing HER2. Therefore, there have been attempts to improve prognosis of cancer patients being non-responsive or poor-responsive to trastuzumab by a combination therapy, in the context of enhancing extent or spectrum of efficacies of trastuzumab.

For instance, U.S. Pat. Appln. Pub. No. 2011-0086004 discloses a combined cancer therapy with trastuzumab and IL-21. U.S. Pat. Appln. Pub. No. 2012-0107270 describes trastuzumab in combination with tenascin-C targeting antibody conjugated with IL-2.

U.S. Pat. Appln. Pub. No. 2005-0101618 discloses a cancer therapy with trastuzumab and erbB2 ligand. Europe Pat. Appln. Pub. No. 2134364 discloses inhibition of cancer cell proliferation by trastuzumab in combination with telomerase inhibitors. WO 2008/031531 describes that trastuzumab in combination with pertuzumab may suppress cancer metastasis.

Throughout this application, various patents and publications are referenced, and citations are provided in parentheses. The disclosure of these patents and publications in their entities are hereby incorporated by references into this application in order to more fully describe this invention and the state of the art to which this invention pertains.

Technological Problems to be Solved

The present inventors have made intensive researches to develop antibodies capable of preventing or treating HER2-related diseases, particularly cancers (more particularly breast cancer and stomach cancer). In particular, the present inventors have made intensive researches to develop antibodies in combination with trastuzumab capable of overcoming limitations in anticancer efficacies associated with trastuzumab treatment as a single agent. As a result, the present inventors have developed novel antibodies having significant anticancer efficacies per se, and much higher efficacies in combination with trastuzumab for prevention or treatment of cancers (particularly breast cancer and stomach cancer, and more particularly HER2-expressing breast cancer and stomach cancer).

Accordingly, it is an object of this invention to provide an antibody to human epidermal growth factor receptor 2 (HER2) or antigen-binding fragment thereof.

It is another object of this invention to provide a nucleic acid molecule coding for the present HER2 antibody or antigen-binding fragment thereof.

It is still another object of this invention to provide a recombinant vector carrying the nucleic acid molecule.

It is further object of this invention to provide a host cell transfected with the recombinant vector.

It is another object of this invention to provide a pharmaceutical composition for preventing or treating a cancer.

It is still another object of this invention to provide a pharmaceutical composition for inducing apoptosis.

Other objects and advantages of the present invention will become apparent from the detailed description to follow taken in conjugation with the appended claims and drawings.

DETAILED DESCRIPTION OF THIS INVENTION

In a first aspect of this invention, there is provide an antibody to human epidermal growth factor receptor 2 (HER2) or antigen-binding fragment thereof, comprising:

(a) a heavy chain variable region comprising a complementarity determining region (CDR) H1 of SEQ ID NO:1, CDRH2 of SEQ ID NO:2 and CDRH3 represented by the following formula 1; and (b) a light chain variable region:

$X_1$-$X_2$-$X_3$-$X_4$-$X_5$-$X_6$-$X_7$-Phe-Asp-Tyr     (1) (SEQ ID NO: 252)

wherein $X_1$ represents His, Asn, Ser or Ala; $X_2$ represents Leu, Phe, Tyr, His, Met, Trp, Asn, Ile or Ala; $X_3$ represents Gly or Cys; $X_4$ represents Gly or Ser; $X_5$ represents Thr, Met or Ala; $X_6$ represents Ala, Ser, Gly or Thr; and $X_7$ represents Ser, Ala, Cys or Thr.

The present inventors have made intensive researches to develop antibodies capable of preventing or treating HER2-related diseases, particularly cancers (more particularly breast cancer and stomach cancer). In particular, the present inventors have made intensive researches to develop antibodies in combination with trastuzumab capable of overcoming limitations in anticancer efficacies associated with trastuzumab treatment as a single agent. As a result, the present inventors have developed novel antibodies having significant anticancer efficacies per se, and much higher efficacies in combination with trastuzumab for prevention or treatment of cancers (particularly breast cancer and stomach cancer, and more particularly HER2-expressing breast cancer and stomach cancer).

The antibody of this invention has a specific binding capacity to HER2. In particular, the present antibody binds to an epitope on HER2 different from an epitope to which trastuzumab is bound.

The term used herein "trastuzumab" refers to an antibody disclosed in U.S. Pat. No. 5,821,337.

The antibody of the invention exhibits cytotoxicity effects or proliferation inhibition effects against various HER2-expressing cancer cells. There is no intended distinction between the terms "cytotoxicity" and "proliferation inhibition" in conjunction with cancer cells, and these terms are interchangeably used herein.

The term used herein "antibody" refers to HER2-specific antibodies including a whole antibody as well as any antigen-binding fragment of antibodies.

The whole antibody includes two full-length light chains and two full-length heavy chains, and each light chain is linked to the heavy chain by disulfide bond. The heavy chain constant region includes five different isotypes (γ, μ, α, δ and ε) which are classified into subgroups of γ1, γ2, γ3, γ4, α1 and α2. The light chain constant region includes two different isotypes (κ and λ) (Cellular and Molecular Immunology, Wonsiewicz, M. J., Ed., Chapter 45, pp. 41-50, W. B. Saunders Co. Philadelphia, Pa. (1991); Nisonoff, A., Introduction to Molecular Immunology, 2nd Ed., Chapter 4, pp. 45-65, sinauer Associates, Inc., Sunderland, Mass. (1984)).

Antigen-binding fragment refers to any antibody fragment capable of binding to antigen including Fab, F(ab'), F(ab')$_2$, Fv and so on. Fab has one antigen-binding site which is composed of variable domains of heavy chain and light chain of the antibody, a constant domain of light chain and the first constant domain (CH$_1$) of heavy chain. Fab' is different to Fab in the sense that there is a hinge region containing one or more cysteine residues at C-terminal of CH$_1$ domain of heavy chain. F(ab')$_2$ antibody is produced by forming a disulfide bond between cysteine residues of hinge region of Fab'. Fv is a minimal antibody fragment composed of variable regions of heavy chain and light chain, and recombinant technique to prepare a Fv fragment is disclosed in PCT WO 88/10649, WO 88/106630, WO 88/07085, WO 88/07086 and WO 88/09344. In two-chain, variable regions of heavy chain and light chain are linked by non-covalent bond, and in single-chain Fv, variable regions of heavy chain and light chain are generally linked by covalent bond via a peptide linker or directly linked to each other at C-terminal, forming a dimer such as two-chain Fv. Such antibody fragments may be obtained using a proteolytic enzymes (e.g., a whole antibody is digested with papain to produce Fab fragments, and pepsin treatment results in the production of F(ab')$_2$ fragments), and may be prepared by genetic recombination techniques.

According to an embodiment, the antibody of this invention includes Fab antibodies and whole antibodies. In addition, the heavy chain constant region is selected from the isotypes consisting of γ, μ, α, δ or ε. Preferably, the heavy chain constant region includes γ1, γ3 and γ4 isotypes, most preferably γ1 isotype. The light chain constant region may be κ and λ isotype, preferably, κ isotype. Therefore, a preferable embodiment of the present antibody is Fab or IgG1 antibody comprising κ light chain and γ1 heavy chain.

The term "heavy chain" used herein refers to both a full-length heavy chain and its portion, which includes variable domain ($V_H$) containing the amino acid sequence of a variable region sequence for specifically binding to antigen and three constant domains ($C_{H1}$, $C_{H2}$ and $C_{H3}$). The term "light chain" used herein refers to both a full-length light chain and its part, which includes variable domain ($V_L$) containing the amino acid sequence of a variable region sequence for specifically binding to antigen and a constant domain (CO.

The term used herein "CDR (complementarity determining region)" refers to an amino acid sequence of hypervariable regions of heavy and light chains of immunoglobulins (Kabat et al., Sequences of Proteins of Immunological Interest, 4th Ed., U.S. Department of Health and Human Services, National Institutes of Health (1987)). Each of the heavy and light chains comprises three CDRs (heavy chain (CDRH1, CDRH2 and CDRH3) and light chain (CDRL1, CDRL2 and CDRL3)). CDR provides contacting residues playing a crucial role in antibody binding to an antigen or epitope.

In the present antibody, CDRH3 is represented by the formula 1.

In the formula 1, $X_1$ represents His, Asn, Ser or Ala; specifically His, Asn or Ser; more specifically His or Asn; still more specifically His.

In the formula 1, $X_2$ represents Leu, Phe, Tyr, His, Met, Trp, Asn, Ile or Ala; specifically Leu, Phe, Tyr, His, Met, Trp, Asn or Ile; more specifically Leu, Phe or Tyr; still more specifically Leu.

In the formula 1, $X_3$ represents Gly or Cys; specifically Gly.

In the formula 1, $X_4$ represents Gly or Ser; specifically Gly.

In the formula 1, $X_5$ represents Thr, Met or Ala; specifically Thr.

In the formula 1, $X_6$ represents Ala, Ser, Gly or Thr; specifically Ala.

In the formula 1, $X_7$ represents Ser, Ala, Cys or Thr; specifically Ser.

According to an embodiment, $X_1$ represents His, Asn or Ser; $X_2$ represents Leu, Phe or Tyr; $X_3$ represents Gly; $X_4$ represents Gly; $X_5$ represents Thr, Met or Ala; $X_6$ represents Ala, Ser, Gly or Thr; and $X_7$ represents Ser, Ala, Cys or Thr.

More specifically, $X_1$ represents His, Asn or Ser; $X_2$ represents Leu, Phe or Tyr; $X_3$ represents Gly; $X_4$ represents Gly; $X_5$ represents Thr; $X_6$ represents Ala; and $X_7$ represents Ser.

Still more specifically, CDRH3 comprises the amino acid sequence selected from the group of SEQ ID NOs:3, 27-28, 32 and 39-86; still much more specifically, CDRH3 comprises the amino acid sequence of SEQ ID NOs:3, 43, 64, 67, 71, 76, 83, 84 or 85; most specifically, SEQ ID NO:3.

According to an embodiment, the light chain variable region comprises CDRL1 of SEQ ID NO:4, CDRL2 of SEQ ID NO:5 and CDRL3 represented by the following formula 2:

$$Y_1\text{-}Y_2\text{-}Y_3\text{-}Y_4\text{-}Y_5\text{-}Y_6\text{-Pro-Trp-Thr} \qquad (2)\ (\text{SEQ ID NO: 253})$$

wherein $Y_1$ represents Gln, Asp or Ala; $Y_2$ represents Gln, Asn, Glu or Ala; $Y_3$ represents Leu, Met, Asn, Ile, Ser, Thr, Ala or Lys; $Y_4$ represents Tyr, Ala, Ser, Arg, Val, Gly, Met or Phe; $Y_5$ represents Ser, Phe, Tyr, Arg, Ile, Gly, Lys, Asn, Val or Ala; and $Y_6$ represents Thr, Ser, Val, Ile, Ala, Gly, Asn, Glu, Phe or Leu.

In the formula 2, $Y_1$ represents Gln, Asp or Ala; specifically Gln or Asp; more specifically Gln.

In the formula 2, $Y_2$ represents Gln, Asn, Glu or Ala; specifically Gln, Asn or Glu; more specifically Gln.

In the formula 2, $Y_3$ represents Leu, Met, Asn, Ile, Ser, Thr, Ala or Lys; specifically Leu, Met, Asn, Ile, Ser or Thr; more specifically Leu, Met, Asn or Ile; still more specifically Leu or Met; most specifically, Leu.

In the formula 2, $Y_4$ represents Tyr, Ala, Ser, Arg, Val, Gly, Met or Phe; specifically Tyr or Ala.

In the formula 2, $Y_5$ represents Ser, Phe, Tyr, Arg, Ile, Gly, Lys, Asn, Val or Ala; specifically Ser, Phe, Tyr, Arg or Ile; more specifically Ser, Phe or Tyr.

In the formula 2, $Y_6$ represents Thr, Ser, Val, Ile, Ala, Gly, Asn, Glu, Phe or Leu; specifically Thr, Ser, Val, Ile, Ala, Gly or Asn; more specifically Thr, Ser or Ala.

According to an embodiment, $Y_1$ represents Gln or Asp; $Y_2$ represents Gln; $Y_3$ represents Leu, Met, Asn, Ile, Ser or Thr; $Y_4$ represents Tyr, Ala, Ser, Arg, Val, Gly, Met or Phe; $Y_5$ represents Ser, Phe, Tyr, Arg or Ile; and $Y_6$ represents Thr, Ser, Val, Ile, Ala, Gly or Asn.

More specifically, CDRL3 comprises the amino acid sequence of SEQ ID NOs:6, 33-38 or 87-245; still more specifically, CDRL3 comprises the amino acid sequence of SEQ ID NOs:6, 88, 109, 131, 155, 156, 157, 178, 218, 220, 222 or 239; most specifically, SEQ ID NOs:6, 88 (hz1E11-3), 218 (hz1E11-133) or 239 (hz1E11-154).

According to an embodiment, the heavy chain variable region comprises the amino acid sequence of SEQ ID NOs:8 (1E11) or 24 (hz1E11).

According to an embodiment, the light chain variable region comprises the amino acid sequence of SEQ ID NOs:10 (1E11), 26 (hz1E11), 247 (hz1E11-3), 249 (hz1E11-133) or 251 (hz1E11-154).

As demonstrated in Examples, while the antibody of the present invention is specifically bound to sub-domain 4 among extracellular domains of HER2, the present antibody is bound to an epitope on sub-domain 4 being different from an epitope of trastuzumab.

The present HER2 antibody or its antigen-binding fragment includes variants of amino acid sequences set forth in the appended Sequence Listing so long as they are capable of specifically recognizing HER2. For example, amino acid sequences of antibodies may be altered to improve binding affinity and/or the other biological characteristics of antibodies. For example, such alterations include deletion, insertion and/or substitution of amino acid residues of antibodies.

Such amino acid variations may be provided on the basis of a relative similarity of amino acid side chains, e.g., hydrophobicity, hydrophilicity, charge and size. By the analysis for size, shape and type of the amino acid side chains, it could be clear that all of arginine, lysine and histidine residues are those having positive charge; alanine, glycine and serine have a similar size; phenylalanine, tryptophan and tyrosine have a similar shape. Accordingly, based on these considerable factors, arginine, lysine and histidine; alanine, glycine and serine; and phenylalanine, tryptophan and tyrosine may be considered to be functional equivalents biologically.

For introducing variations, a hydropathic index of amino acids may be considered. Based on the hydrophobicity and the charge, the hydropathic index is given to each amino acid: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

For providing an interactive biological function of proteins, the hydropathic index of the amino acid is very important. It is well known to one of skill in the art that variants can possess a similar biological activity only where proteins are replaced with amino acids having similar hydropathic index. Where variations are introduced based on the hydropathic index, the substitution is preferably performed between amino acid residues having no more than ±2 difference in hydropathic index values more preferably within ±1, much more preferably within ±0.5.

It would be also obvious to those of skill in the art that substitutions of amino acids with other amino acids having similar hydrophilicity values may result in the generation of variants having biologically equivalent activities. As disclosed in U.S. Pat. No. 4,554,101, each amino acid residue is assigned the following hydrophilicity values: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Where variations are intended to introduced based on the hydrophilicity value, the substitution is preferably performed between amino acid residues having no more than ±2 difference in hydrophilicity values, more preferably within ±1, much more preferably within ±0.5.

The alteration of amino acid residues without substantially impairing protein activity is well known to one skilled in the art (H. Neurath, R. L. Hill, The Proteins, Academic Press, New York, 1979). Such amino acid alteration includes substitutions of Ala/Ser, Val/Ile, Asp/Glu, Thr/Ser, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu and Asp/Gly, but not limited thereto.

Considering the afore-mentioned variations having biologically equivalent activities, it could be understood that either antibody of this invention or the nucleic acid encoding the same includes substantially identical sequences to the sequences set forth in the appended Sequence Listing. The substantially identical sequences refers to those showing preferably at least 61%, more preferably at least 70%, still more preferably at least 80%, most preferably at least 90% nucleotide similarity to the sequences of the appended Sequence Listing, as measured using one of the conventionally used sequence comparison algorithms. Methods of alignment of sequences for comparison are well-known in the art. Various programs and alignment algorithms are described in: Smith and Waterman, *Adv. Appl. Math.* 2:482 (1981); Needleman and Wunsch, *J. Mol. Bio.* 48:443(1970); Pearson and Lipman, *Methods in Mol. Biol.* 24: 307-31 (1988); Higgins and Sharp, *Gene* 73:237-44(1988); Higgins and Sharp, *CABIOS* 5: 151-3(1989); Corpet et al., *Nuc. Acids Res.* 16:10881-90(1988); Huang et al., *Comp. Appl.*

*BioSci.* 8:155-65(1992); and Pearson et al., *Meth. Mol. Biol.* 24:307-31(1994). The NCBI Basic Local Alignment Search Tool (BLAST) (Altschul et al., *J. Mol. Biol.* 215: 403-10 (1990)) is available from several sources, including the National Center for Biological Information (NBCI, Bethesda, Md.) and on the Internet, for use in connection with the sequence analysis programs for blastp, blasm, blastx, tblastn and tblastx. It can be accessed at the NCBI website (ncbi.nlm.nih.gov/BLAST/). A description of how to determine sequence identity using this program is available at the website ncbi.nlm.nih.gov/BI-AST/blasthelp.html.

The antibody of the present invention includes, but not limited to, monoclonal antibody, multispecific antibody, human antibody, humanized antibody, chimeric antibody, single-chain Fvs (scFV), single-chain antibody, Fab fragment, F(ab') fragment, disulfide-linked Fvs (sdFV) and anti-idiotype (anti-Id) antibody, and epitope-binding fragment thereof.

The CDR sequences of the present antibodies exhibit low similarity to CDR sequences of publicly known antibodies, addressing that the CDR sequences are unique. For example, antibodies disclosed in U.S. Pat. Nos. 7,329,737 and 7,993,646 that have the highest similarity to the present antibodies in BLAST search ncbi.nlm.nih.gov/BLAST/) show similarity of less than 50% to the CDR sequences of 1E11 antibody, a mother antibody, and furthermore are bound to hK-1 being different from the target of the present antibodies.

Accordingly, the amino acid sequences of the present antibodies may be considered novel and unique.

In another aspect of this invention, there is provided a nucleic acid molecule encoding the present antibody or antigen-binding fragment thereof.

The term used herein "nucleic acid molecule" comprehensively refers to a DNA (gDNA and cDNA) or RNA molecule, and the basic nucleotides of nucleic acid molecule also include analogues with modified sugar or base as well as natural nucleotides (Scheit, Nucleotide Analogs, John Wiley, New York (1980); Uhlman and Peyman, Chemical Reviews, 90:543-584 (1990)). The sequence of the present nucleic acid molecule encoding the variable regions of heavy and light chain could be modified. Such modification includes addition, deletion or non-conservative or conservative substitution of nucleotide.

According to an embodiment, the nucleic acid molecule encoding the heavy chain variable region comprises a nucleotide sequence of SEQ ID NO:7 or 23.

According to an embodiment, the nucleic acid molecule encoding the light chain variable region comprises a nucleotide sequence of SEQ ID NO:9, 25, 246, 248 or 250.

The nucleic acid molecule coding for the present HER2 antibody also includes a nucleotide sequence sharing substantial homology with the above nucleotide sequence. The substantial homology means the nucleotide sequence sharing homology of at least 80%, more preferably 90% and most preferable 95% by sequence alignment analysis using maximal alignment between the nucleotide sequence of this invention and other random sequences and algorithm ordinarily known to those skilled in the art.

In still another aspect of this invention, there is provided a recombinant vector comprising the present nucleic acid molecule described above.

The term used herein "vector" is a tool for expressing a target gene in a host cell, including a plasmid vector; a cosmid vector; and a virus vector such as a bacteriophage vector, an adenovirus vector, a retrovirus vector and an adeno-associated virus vector.

According to an embodiment, the nucleic acid molecules encoding the variable regions of light and heavy chains are operatively linked to a promoter.

The term used herein "operatively linked" refers to functional linkage between a nucleic acid expression control sequence (e.g., a promoter, signal sequence, or array of transcription factor binding sites) and a second nucleic acid sequence, wherein the expression control sequence affects transcription and/or translation of the nucleic acid corresponding to the second sequence.

The recombinant vectors of this invention may be constructed by various methods known to those skilled in the art and its practical methods are described in Sambrook et al., *Molecular Cloning, A Laboratory Manual*, Cold Spring Harbor Laboratory Press (2001), which is herein incorporated by reference.

Typically, the vector of this invention may be constructed as cloning or expression vector. In addition, the vector of this invention may be constructed using a prokaryotic or eukaryotic cell as a host cell.

For instance, where the expression vector is constructed for eukaryotic host cell, a promoter derived from the genome of mammalian cells (e.g., metallothionein promoter, β-actin promoter, human hemoglobin promoter and human muscle creatine promoter) or mammalian virus (e.g., adenovirus late promoter; vaccinia virus 7.5K promoter, SV40 promoter, cytomegalovirus promoter, tk promoter of HSV, mouse mammary tumor virus (MMTV) promoter, LTR promoter of HIV, moloney virus promoter, Epstein-Barr virus (EBV) promoter and Rous sarcoma virus (RSV) promoter) may be used. The vector generally contains a polyadenylation sequence as a transcription terminator.

The vector of this invention may be fused with other sequences to purify an antibody expressed. For example, a sequence to be fused includes glutathione-S-transferase (Pharmacia, USA), maltose-binding protein (NEB, USA), FLAG (IBI, USA) and 6×His (hexahistidine; Quiagen, USA) and so on.

Since the protein expressed by the vector of the present invention is antibody, the expressed antibody could be also purified throughout protein A column in an easy manner without additive sequences for purification.

The expression vector of this invention includes an antibiotics-resistance gene known to those ordinarily skilled in the art as a selection marker, for example resistant genes against ampicillin, gentamycin, carbenicillin, chloramphenicol, streptomycin, kanamycin, geneticin, neomycin and tetracycline.

In further aspect of this invention, there is provided a host cell transformed with the above-described recombinant vector.

The host cells in which the present vector is stably and successively cloned and expressed, also utilize any one known to those skilled in the art, for example, suitable eukaryotic host cell including COST cell (monkey kidney cell), NSO cell, SP2/0, CHO (Chinese hamster ovary) cell, W138, BHK (baby hamster kidney) cell, MDCK, myeloma cell line, HuT 78 cell and HEK-293 cell, but not limited thereto.

In another aspect of this invention, there is provided a pharmaceutical composition for preventing or treating a cancer, comprising: (a) a pharmaceutically effective amount of the present antibody to HER2 or antigen-binding fragment thereof; and (b) a pharmaceutically acceptable carrier.

Since the present pharmaceutical composition comprises the HER2 antibody of the present invention or its antigen-binding fragment as an active ingredient, the common descriptions between them are omitted in order to avoid undue redundancy leading to the complexity of this specification.

As addressed in Examples, the HER2 antibody of the present invention in combination with trastuzumab kills cancer cells (particularly, breast cancer cells, more particularly, HER2-expressing breast cancer cells) with significantly enhanced cytotoxicity and therefore very effective in therapy of cancer (particularly, breast cancer and stomach cancer, more particularly, HER2-expressing breast cancer and stomach cancer). According to an embodiment, the pharmaceutical composition further comprises trastuzumab.

The cancer to be prevented or treated by the present composition includes various cancers known to one of skill in the art, for example, breast cancer, ovarian cancer, stomach cancer, lung cancer, liver cancer, bronchus cancer, nasopharyngeal cancer, laryngeal cancer, pancreatic cancer, bladder cancer, colorectal cancer, colon cancer, cervical cancer, brain cancer, prostate cancer, bone cancer, head and neck cancer, skin cancer, thyroid cancer, parathyroid cancer or ureteral cancer.

Specifically, the cancer to be prevented or treated by the composition is HER2-expressing cancer, more specifically HER2-expressing breast cancer or stomach cancer.

In still another aspect of this invention, there is provided a pharmaceutical composition for inducing apoptosis, comprising: (a) a pharmaceutically effective amount of the present antibody to HER2 or antigen-binding fragment thereof; and (b) a pharmaceutically acceptable carrier.

According to an embodiment, the pharmaceutical composition induces apoptosis for prevention or treatment of a hyperproliferative disease; wherein the hyperproliferative disease is cancer, hyperplasia, keloid, Cushing syndrome, primary aldosteronism, erythroplakia, polycythemia vera, leukoplakia, hyperplastic scar, lichen planus, lentiginosis, arteriosclerosis, atherosclerosis, restenosis or stenosis.

The pharmaceutically acceptable carrier may be conventional one for formulation, including lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but not limited thereto. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in Remington's Pharmaceutical Sciences (19th ed., 1995), which is incorporated herein by reference.

The pharmaceutical composition according to the present invention may be parenterally administered, for example, by intravenous, subcutaneous, intramuscular, intraperitoneal, local, nasal, pulmonary or rectal administration.

A suitable dose of the pharmaceutical composition of the present invention may vary depending on pharmaceutical formulation methods, administration methods, the patient's age, body weight, sex, severity of diseases, diet, administration time, administration route, an excretion rate and sensitivity to the pharmaceutical composition. Preferably, the pharmaceutical composition of the present invention is administered with a daily dose of 0.0001-100 mg/kg (body weight). The term "pharmaceutically effective amount" refers to an amount suitable to prevent or treat cancer.

According to the conventional techniques known to those skilled in the art, the pharmaceutical composition may be formulated with pharmaceutically acceptable carrier and/or excipient, finally providing several forms including a unit dose form and a multi-dose form. Formulation may be oil or aqueous media, resuspension or emulsion, extract, powder, suppository, granule, tablet or capsule and further comprise dispersant or stabilizer.

The antibody of the present invention may be used to diagnose HER2-expressing related disorders, diseases or conditions.

In further aspect of this invention, there is provided a kit for diagnosing a HER2-expressing related disorder, disease or condition comprising the present antibody to HER2 or antigen-binding fragment thereof.

The HER2-expressing related disorder, disease or condition is particularly cancer, for example, breast cancer, ovarian cancer, stomach cancer, lung cancer, liver cancer, bronchus cancer, nasopharyngeal cancer, laryngeal cancer, pancreatic cancer, bladder cancer, colorectal cancer, colon cancer, cervical cancer, brain cancer, prostate cancer, bone cancer, head and neck cancer, skin cancer, thyroid cancer, parathyroid cancer or ureteral cancer. Specifically, the diagnosis kit of the present invention is used to diagnose HER2-expressing cancer, more specifically HER2-expressing breast cancer or stomach cancer.

The antibody of the present invention may be used to analyze a drug responsiveness of the present antibody in a patient.

In another aspect of this invention, there is provided a kit for analyzing a drug responsiveness comprising the present antibody.

The analysis kit of the present invention is used to evaluate a drug responsiveness of the present antibody in a patient. For example, where cancer cells obtained from a patient are incubated with the antibody of this invention and the antibody is elucidated to be bound to the cells, the patient is determined to possess a drug responsiveness of the present antibody.

Since the present kit comprises antibodies, it may be fabricated for immunoassay or immunostaining. The immunoassay or immunostaining format includes, but not limited to, radioimmunoassay, radioimmuno-precipitation, enzyme-linked immunosorbent assay (ELISA), capture-ELISA, inhibition or competition assay, sandwich assay, flow cytometry, immunofluorescence staining and immunoaffinity purification, but not limited thereto. The immunoassay or immunostaining procedures can be found in Enzyme Immunoassay, E. T. Maggio, ed., CRC Press, Boca Raton, Fla., 1980; Gaastra, W., Enzyme-linked immunosorbent assay (ELISA), in *Methods in Molecular Biology*, Vol. 1, Walker, J. M. ed., Humana Press, N J, 1984; and Ed Harlow and David Lane, *Using Antibodies*, A Laboratory Manual, Cold Spring Harbor Laboratory Press, 1999, which are incorporated herein by reference.

For example, according to the radioimmunoassay method, the radioisotope (e.g., $C^{14}$, $I^{125}$, $P^{32}$ and $S^{35}$) labeled antibody may be used to identify HER2 on the surface of cancer cells. According to the ELISA method, the specific example of the present method may comprise the steps of: (i) coating a surface of a solid substrate with a biosample to be analyzed; (ii) incubating the biosample with the HER2 antibody of this invention as a primary antibody; (iii) incubating the resultant of step (ii) with a secondary antibody conjugated with an enzyme; and (iv) measuring the activity of the enzyme.

The solid substrate may be hydrocarbon polymers (e.g., polystyrene and polypropylene), glass, metals or gels. Most preferably, the solid substrate is a microtiter plate.

The enzyme conjugated to the secondary antibody includes an enzyme catalyzing colorimetric, fluorometric, luminescence or infra-red reactions, for example alkaline phosphatase, β-galactosidase, horseradish peroxidase, luciferase and Cytochrome $P_{450}$. Where using alkaline phosphatase, bromochloroindolylphosphate (BCIP), nitro blue tetrazolium (NBT), naphthol-AS-B 1-phosphate and ECF (enhanced chemifluorescence) may be used as a substrate; in the case of using horseradish peroxidase, chloronaphtol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine, Pierce), HYR (p-phenylenediamine-HCl and pyrocatechol), TMB (3,3,5,5-tetramethylbenzidine), ABTS (2,2-Azine-di[3-ethylbenzthiazoline sulfonate]), o-phenylenediamine (OPD) and naphthol/pyronine, glucose oxidase and t-NBT (nitroblue tetrazolium) and m-PMS (phenzaine methosulfate) may be used as a substrate.

According to the capture-ELISA method, the specific example of the present method may comprise the steps of: (i) coating a surface of a solid substrate with the HER2 antibody as a capturing antibody; (ii) incubating the capturing antibody with a biosample to be analyzed; (iii) incubating the resultant of step (ii) with the HER2 antibody conjugated with a label generating a detectable signal as a detecting antibody; and (iv) measuring the signal generated from the label.

The detecting antibody has a label generating a detectable signal. The label includes, but not limited to, a chemical (e.g., biotin), an enzymatic (e.g., alkaline phosphatase, β-galactosidase, horseradish peroxidase, and Cytochrome $P_{450}$), a radioactive (e.g., $C^{14}$, $I^{125}$, $P^{32}$ and $S^{35}$), a fluorescent (e.g., fluorescein), a luminescent, a chemiluminescent and a FRET (fluorescence resonance energy transfer) label. Various labels and methods for labeling antibodies may be found in Ed Harlow and David Lane, Using Antibodies, A Laboratory Manual, Cold Spring Harbor Laboratory Press, 1999.

The measurement of the enzyme activity or signal in ELISA and capture-ELISA can be carried out by various processes well known in the art. Where biotin is used as labels, the detection may be performed using streptavidin. Where luciferase is used, the detection may be performed using luciferin.

The biosample applicable to the present kit includes, but not limited to, cells, tissues, tissue-derived extracts, lysate or purified product, blood, plasma, serum, lymph and ascitic fluid.

The antibody of the present invention may be used for in vivo or in vitro imaging. In another aspect of this invention, there is provided an imaging composition comprising the antibody of the present invention and a signal-generating label conjugated to the antibody.

The signal-generating label includes, but not limited to, T1 contrast agent (e.g., Gd chelate compound), T2 contrast agent (e.g., superparamagnetic materials (e.g., magnetite, $Fe_3O_4$, $\gamma$-$Fe_2O_3$, manganese ferrite, cobalt ferrite and nickel ferrite)), radioisotope (e.g. $^{11}C$, $^{15}O$, $^{13}N$, $P^{32}$, $S^{35}$, $^{44}Sc$, $^{45}Ti$, $^{118}I$, $^{136}La$, $^{198}Tl$, $^{200}Tl$, $^{205}Bi$ and $^{206}Bi$), fluorescent materials (e.g., fluorescein, phycoerythrin, rhodamine, lissamine, Cy3 and Cy5), chemiluminescent materials, magnetic particles, mass labels and electron dense particles.

Although the antibody of the present invention alone is useful in cancer therapy, it may be provided in the form of ADC (antibody drug conjugate) by conjugating with other drug because the antibody is able to target HER2-expressing cells.

Therefore, in another aspect of this invention, there is provided an ADC (antibody drug conjugate) comprising the antibody of the present invention and a drug conjugated with the antibody.

The drug conjugated with the antibody includes, but not limited to, chemicals, radionuclides, immunotherapeutics, cytokines, chemokines, toxins, biological agents and enzyme inhibitors, specifically anticancer drugs as follows: acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, *Bacillus* calmette-guerin (BCG), Baker's Antifol, beta-2'-deoxythioguanosine, bisantrene HCl, bleomycin sulfate, busulfan, buthionine sulfoximine, BWA773U82, BW 502U83/HCl, BW 7U85 mesylate, ceracemide, carbetimer, carboplatin, carmustine, chlorambucil, chloroquinoxaline-sulfonamide, chlorozotocin, chromomycin A3, cisplatin, cladribine, corticosteroids, *Corynebacterium parvum*, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, doxorubicin, echinomycin, dedatrexate, edelfosine, eflornithine, Elliott's solution, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5-fluorouracil, Fluosol™, flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, 4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extraction residue of *Bacillus* calmette-guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, TNF (tumor necrosis factor), uracil mustard, vinblastine sulfate, vincristine sulfate, vindesine, vinorelbine, vinzolidine, Yoshi 864, zorubicin, cytosine arabinoside, etoposide, melphalan, taxotere and taxol.

Effects of this Invention

The features and advantages of the present invention will be summarized as follows:

(a) The antibody of the invention binds specifically to HER2 over-expressed in cancer cells (particularly, breast cancer and stomach cancer cells), specifically to an epitope on HER2 being different from epitope for trastuzumab.

(b) The CDR sequences of the present antibodies exhibit low similarity to CDR sequences of publicly known HER2 antibodies, addressing that the CDR sequences are unique.

(c) The antibodies of the present invention in combination with trastuzumab kill cancer cells with significantly enhanced cytotoxicity and therefore very effective in therapy of cancer (particularly, breast cancer and stomach cancer).

(d) Without wishing to be bound by theory, the enhanced efficacies of the combined therapy would address that the antibodies of the present invention bind to epitope on HER2 being different from epitope for trastuzumab, and inhibit HER2 in a cooperative manner with trastuzumab.

(e) The antibodies of the present invention capable of inducing apoptosis can be used for prevention or treatment of hyperproliferative diseases.

(f) The present invention can also be useful in cancer diagnosis, drug responsiveness analysis, imaging and ADC (antibody drug conjugate) as well as cancer therapy.

BRIEF DESCRIPTION OF THE DRAWINGS

FIGS. 3A and 3B respectively show the results of SPR analysis and ELISA analysis.

FIGS. 7A through 7C show the tumor cell growth inhibitory effects in an NCI-N87 xenograft animal model by the treatment with 1E11 antibody or trastuzumab alone or in combination thereof. FIG. 7A shows a graph illustrating the change in tumor volume, FIG. 7B shows a graph illustrating the change in tumor weight, and FIG. 7C shows an image illustrating the staining result of tumor tissues. Control Ab is palivizumab.

Figure 1:
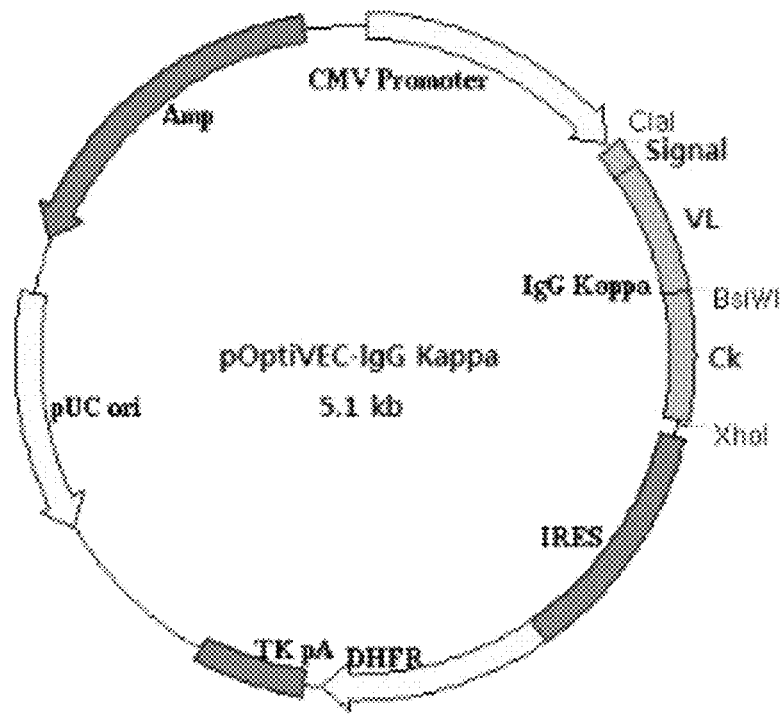
FIG. 1 shows genetic maps of pcDNA3.3-IgG Heavy vector and pOptiVEC-IgG Kappa vector.
Figure 1:
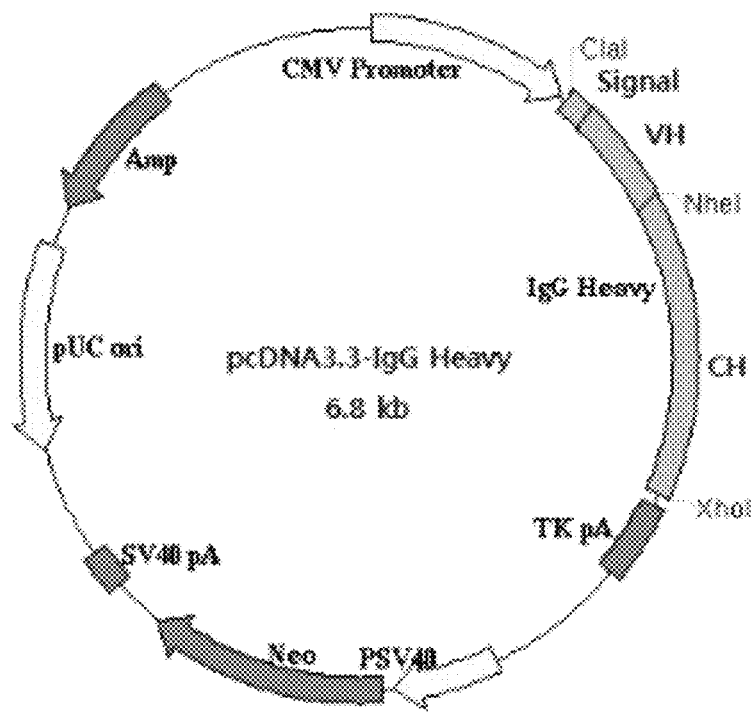

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Development of HER2 Antibodies

For preparing antibodies, the extracellular domain (ECD) of HER2 protein was produced using animal cells and then used it as an antigen. The DNA, where a hinge region of human IgG1 and Fc portion (CH2-CH3) were bound to the C-terminus of ECD, was cloned using HindIII and BamHI restriction enzymes. Then, the cloned vector was transiently transfected into the FreeStyle™ 293F (Invitrogen, Cat. No. R790-07) cell using polyethyleneimine (Polyscience Inc., Cat. No. 23966), and HER2-ECD Fc fusion protein was purified from the cell culture using Protein-A Ceramic HyperD F resin (PALL, Cat No. 20078-028). The purified protein was quantitated using a Protein assay dye (Bio-Rad, Cat. No. 500-0006), subjected to SDS-PAGE, and its concentration and purity were confirmed via Coomassie staining. 100 μg of the purified protein antigen was mixed with Freund's adjuvant (Sigma, Cat. No. F5506) and then intraperitoneally injected into BALB/c mice (DBL Co., Ltd., Korea). In two weeks, 100 μg of the antigen was diluted in PBS and injected again, and three days thereafter, the spleen of the mouse was taken out and lymphocytes were isolated therefrom. The isolated lymphocytes were mixed with the myeloma cell line SP2/0-Ag14 (ATCC, Cat. No. CRL-1581) at a 5:1 ratio, and fused using PEG-1500 (Roche, Cat. No. 783641). The fused cells were cultured in a medium containing the HAT supplement (Sigma, Cat. No. H0262), and the fused cells (hybridoma) were selectively sorted out and cultured.

The thus-obtained hybridoma cells were examined via ELISA assay to determine whether they were the cells producing antibodies that bind to antigens. HER2-ECD-Fc or ChromPure human IgG (hIgG, Jackson Immunoresearch Lab. Inc., Cat. No. 009-000-003) was immobilized at room temperature to a Costar 96-well plate (Corning, Cat. No. 3590) at a concentration of 1 μg/mL for 1 hour. The resultant was washed 3 times with TBS-T (0.05% Triton X-100) and then blocked at room temperature with 300 μL of TBS-T/SM (2% skim milk) for 30 minutes. The blocked plate was washed 3 times and added with a hybridoma culture broth, and allowed to bind to antibodies at 37° C. for 1 hour. After washing the resultant 3 times, anti-mouse IgG-HRP (Pierce, Cat. No. 31439) as a secondary antibody was diluted in TBS-T/SM at a 1:5,000 ratio and allowed to bind thereto at 37° C. for 1 hour. After washing the resultant 3 times, TMB (SurModics, Cat. No. TMBC-1000-01) was added thereto and allowed to develop a color at room temperature for 5 minutes and added with 1 N sulfuric acid (DukSan, Cat. No. 254) to stop the color development. The absorbance was measured at 450 nm using Victor X3 (PerkinElmer, Cat. No. 2030-0030), and the antibodies that bind specifically to HER2-ECD-Fc were selected.

Since HER2 is a protein expressed on the cell surface, it was examined whether the developed antibodies were bound to HER2-overexpressing cells via cell-based ELISA assay. The HER2-overexpressing ovary cancer cell line, SKOV-3 (Korean Cell Line Bank (KCLB), Cat. No. 30077) was aliquoted into the Costar 96-well cell culture plate (Corning, Cat. No. 3595) at a concentration of 10,000 cell/well and cultured for 24 hours. On the following day, after removing the cell culture supernatant, the resultant was washed with PBS 3 times, added with hybridoma culture broth, and cultured further at 37° C. for 2 hours. After washing the resultant 3 times with TBS-T, goat anti-mouse IgG-HRP as a secondary antibody which was diluted in PBS/FBS (3% FBS) at a 1:5,000 ratio, added thereto, and treated at room temperature for 1 hour. After washing the resultant 3 times with TBS-T, it was allowed to develop a color using TMB. 61 clones showing higher absorbance than that of the SP2/0 cell culture as a negative control were selected.

Example 2: Comparison of Inhibitory Effects of Developed Antibodies Against the Growth of Breast Cancer Cells In order to perform a cell viability assay for confirming the inhibitory effect against the proliferation of breast cancer cells, the antibodies from the hybridoma culture broth were purified. The hybridoma was cultured in a culture medium containing 3% FBS, and the antibodies in the form of IgG were purified using Protein-A resin. The purified antibodies were quantitated via BCA assay (Pierce, Cat. No. 23227), subjected to SDS-PAGE, and their concentration and purity were confirmed via Coomassie staining.

Cell viability assay was performed by a single treatment or a combined treatment along with trastuzumab regarding BT-474, the representative breast cancer cell line, and NCI-N87 cell line, the representative stomach cancer cell line, where HER2 is overexpressed. For the combined treatment, a mixture of the developed antibodies and trastuzumab mixed at a 1:1 ratio (weight ratio) was used. To the 96-well plate were aliquoted BT-474 (ATCC, Cat. No. HTB-20, 10,000 cells/well) and NCI-N87 (ATCC, Cat No. CRL-5822, 10,000 cells/well) cells, and cultured for 24 hours. The purified antibodies were respectively treated to have a concentration of 5 μg/mL, and BT-474 and NCI-N87 cell lines were cultured further for 4 days. For cell viability assay, CCK-8 (Dojindo, Cat. No. CK-04-13) was added to a final concentration of 10%, treated at 37° C. for 3 hours, and their absorbance was measured. The relative viability was calculated relative to the absorbance of the well not treated with the antibody, which was set at 100% of viability. Based on the above, 1E11 antibody was selected.

Example 3: Analysis of Antibody Sequence

For antibody sequence assay, a phage Fab antibody library was constructed using the respective hybridoma RNA, and a three-step panning was proceeded to obtain a phage that binds to the HER2-ECD-Fc (Phage display: a laboratory manual, Carlos Barbas III, et al., Cold Spring Harbor Laboratory Press). After culturing the hybridoma, RNA was isolated using SV Total RNA Isolation System (Promega, Cat. No. Z3100) and a cDNA was synthesized therefrom. Using a known primer set (see: Phage display: a laboratory manual, Carlos Barbas III, et al., Cold Spring Harbor Laboratory Press), the variable region of the antibody was amplified, and cloned into pComb3X vector (Barbas laboratory, The Scripps Research Institute) using SfiI restriction enzyme after ligating to human Ck and CH1, and then transformed into ER2537 bacteria (New England Biolabs, Cat. No. 801-N). The transformed bacteria were transfected with VCSM13 helper phage (Stratagene, Cat. No. 200251) to obtain a phage, and a clone which binds to HER2-ECD-Fc was acquired using an immunotube, to which HER2-ECD-Fc was immobilized.

Among the colonies for each of the antibodies, the antibodies that bind to HER2-ECD-Fc were confirmed via ELISA assay. The colonies of the transformed bacteria were cultured at 37° C. until their absorbance at 600 nm reached 0.5, and treated with IPTG at a final concentration of 1 mM, allowed to and expressed antibodies in the form of Fab while culturing overnight at 30° C. After culturing 5 mL, cells were collected by centrifugation, suspended in 0.4 mL 1×TES (50 mM Tris, 1 mM EDTA, 20% (v/v) sucrose, pH 8.0), and treated at 4° C. for 10 minutes. After adding 0.6 mL of 0.2×TES thereto, the resultant was treated at 4° C. for 30 minutes, centrifuged and the supernatant was recovered. After washing the Costar 96-well half area plate (Corning Inc., Cat. No. 3690), which was coated with HER2-ECD-Fc at a concentration of 1 μg/mL, 3 times with TBS-T, it was blocked with TBS-T/SM (3% non-fat skim milk, 0.05% Triton X-100) at room temperature for 1 hour. The culture broth or periplasmic extract (Periplasm) for each colony was treated by diluting it at a 1:3 ratio using TBS-T/SM, and allowed to bind at room temperature for 1 hour. After washing 3 times, anti-HA-HRP (Roche, Cat. No. 120-138-190-01) as a secondary antibody was diluted at a 1:5000 ratio, allowed to bind at room temperature for 1 hour, washed 3 times, and allowed to develop a color using TMB.

Most colonies in the cell culture broth or periplasmic extract had absorbance of 0.2 or higher, and the sequences of the antibodies were analyzed regarding these clones. The sequence analysis revealed that the colonies derived from a single hybridoma were shown to have the same sequences. The amino acid sequences of complementarity determining region (CDR) of the 1E11 antibody are summarized in Table 1 below.

TABLE 1

Amino acid sequences of complementarity determining region (CDR) of the 1E11 antibody

|  | Light Chain | Heavy Chain |
|---|---|---|
| CDR1 | LASQTIGTWLA (SEQ ID NO: 4) | SYTMS (SEQ ID NO: 1) |
| CDR2 | ATSLAD (SEQ ID NO: 5) | YISNGGGSTYYPDTVKG (SEQ ID NO: 2) |
| CDR3 | QQLYSTPWT (SEQ ID NO: 6) | HLGGTASFDY (SEQ ID NO: 3) |

TABLE 2

Primers for amplification of variable regions

| Primers | Sequence |
|---|---|
| LF-1 | CCGATCGATATGGAGACAGACACACTCCTGCTATGGG<u>TACTGCTGCTCTGGGTTCCAGGTTCCACGTGGGATATTCAGATG</u> (SEQ ID NO: 15) |
| LR-1 | CGGCGTACGTTTCAGCTCCAGCTTGG (SEQ ID NO: 16) |
| HF-1 | CCGATCGATATGGAGACAGACACACTCCTGCTATGGG<u>TACTGCTGCTCTGGGTTCCAGGTTCCACGTGGGAGGTGAAGCT</u> (SEQ ID NO: 17) |
| HR-1 | CGGGCTAGCTGAGGAGACGGTGAC (SEQ ID NO: 18) |

TABLE 3

Primers for amplification of constant regions

| Primers | Sequence |
|---|---|
| Ck-F | GGAGCTGAAACGTACGGTGGCTGCACC (SEQ ID NO: 19) |
| Ck-R | CCGCTCGAGTTAACACTCTCCCCTGTTG (SEQ ID NO: 20) |
| CH-F | CACCGTCTCCTCAGCTAGCACCAAGGGCCCATCG (SEQ ID NO: 21) |
| CH-R | CCGCTCGAGTCATTTACCCGGGGACAGGGAG (SEQ ID NO: 22) |

In the above Tables, the bold letters indicate the restriction sites for restriction enzymes, whereas the underlined parts indicate signal sequences.

The maps of the finally constructed pcDNA3.3-IgG Heavy vector and pOptiVEC-IgG Kappa vector are illustrated in FIG. 1.

Then, the cloned vectors were transiently transfected into FreeStyle™ 293F (Invitrogen, Cat. No. R790-07) animal cells using polyethyleneimine (Polyscience Inc., Cat. No. 23966), and chimeric antibodies were purified from the cell culture broth using Protein-A Ceramic HyperD F resin (PALL, Cat No. 20078-028). The purified chimeric antibodies were quantitated via BCA assay (Pierce, Cat. No. 23227), subjected to SDS-PAGE, and their concentration and purity were confirmed via Coomassie staining.

Example 4: Construction and Production of Chimeric Antibodies

Chimeric antibodies were constructed to prepare the antibodies of the present invention in a more druggable form.

The variable region of the mouse antibodies, for which the nucleotide sequence analysis was completed, was amplified and bound to the human constant regions Cκ and CH, and the heavy chain part was TA cloned by pcDNA3.3-TOPO (Invitrogen, Cat. No., K8300-01) vector, whereas the light chain part was TA cloned by pOptiVEC-TOPO (Invitrogen, Cat. No., 12744-017) vector. The primers used for amplification are shown in Tables 2 and 3 below. The forward primers were inserted with a ClaI restriction site, whereas the reverse primers were added with NheI restriction site for the heavy chain and BsiWI restriction site for the light chain, respectively. Additionally, the forward primers in the variable region were added with a signal sequence so that the chimeric antibodies could be secreted in cell culture broth. The nucleotide sequences and amino acid sequences of Cκ and CH used in the present invention are described in SEQ ID NOs: 11 through 14.

A PCR reaction (30 sec. at 95° C.; 30 sec. at 58° C.; and 30 sec. at 72° C.) was repeatedly performed for 35 cycles using the primers and GoTaq DNA polymerase (Promega, Cat. No. M3005) described above. Each of the amplified PCR products of the variable regions and the constant regions, after being subjected to a 1% agarose gel electrophoresis, was purified using a Qiaquick gel extraction kit (QIAGEN, Cat. No. 28706). In order to connect the variable regions and the constant regions, the PCR products of the variable regions and the constant regions were mixed in an equal amount, and an overlap extension PCR was performed using the forward primers for the variable regions and the reverse primers for the constant regions to obtain gene products, and the products were purified in the same manner as described above. The overlap extension PCR (30 sec. at 95° C.; 30 sec. at 58° C.; and 45 sec. at 72° C.) was repeatedly performed for 35 cycles using the primers and was performed using the GoTaq DNA polymerase (Promega, Cat. No. M3005). The amplified gene products were TA cloned into pcDNA3.3-TOPO (Invitrogen, Cat. No., K8300-01) vector for the heavy chain part, and TA cloned into pOptiVEC-TOPO (Invitrogen, Cat. No., 12744-017) vector for the light chain part, according to the manufacturer's manual.

Figure 2A:
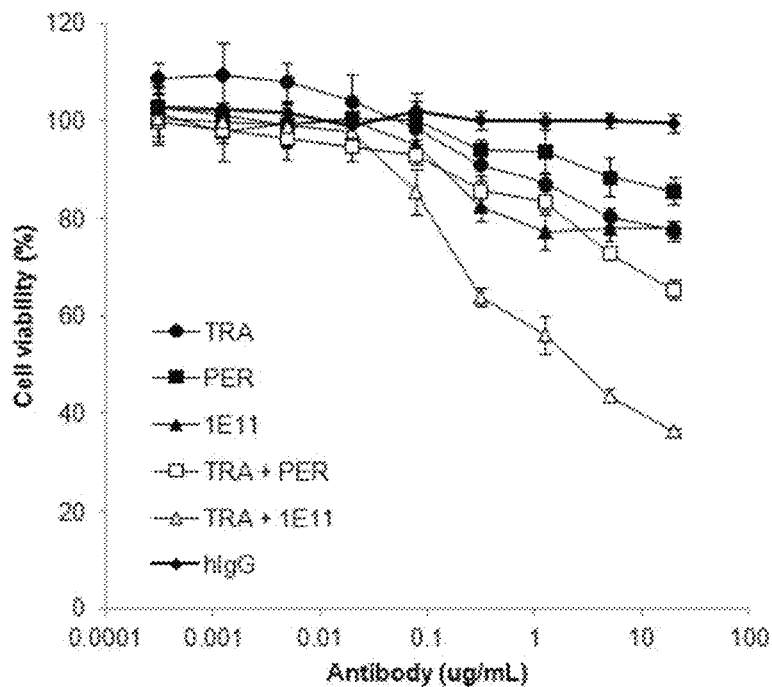
FIGS. 2A and 2B are graphs respectively showing the proliferation inhibitory effects of a single treatment by 1E11 antibody and a combined treatment of 1E11 antibody and trastuzumab against NCI-N87 cancer cell line and BT-474 cancer cell line. TRA, PER, and hIgG respectively indicate trastuzumab, pertuzumab, and human IgG (negative control).
Figure 2B:
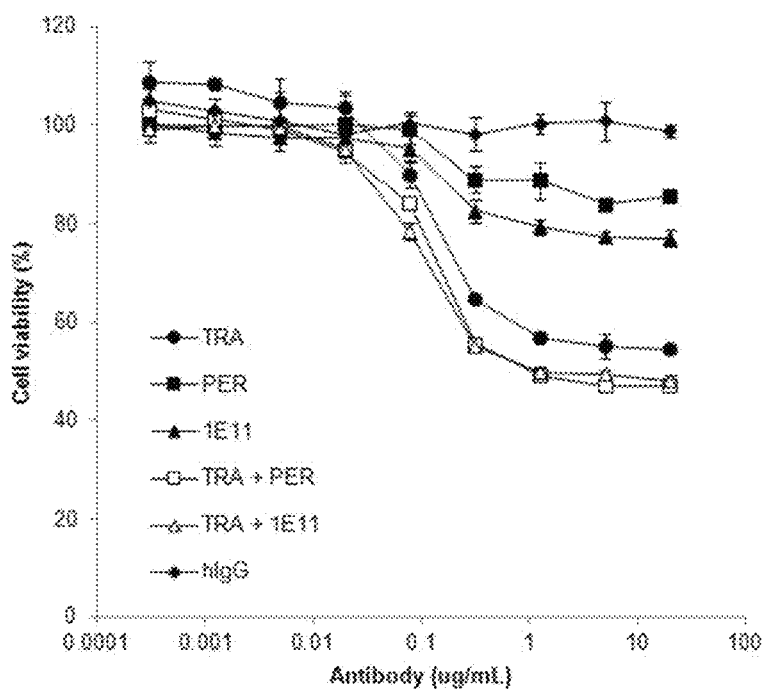

Example 5: Comparison of Inhibitory Effects of Developed Antibodies Against the Growth of Breast Cancer and Stomach Cancer In order to confirm the anticancer effects of the developed antibodies according to their concentration, a cell viability assay was performed regarding cancer cell lines which overexpress HER2 such as, BT-474 (a breast cancer cell line), and NCI-N87 (a stomach cancer cell line). BT-474 (10,000 cells/well) and NCI-N87 (10,000 cells/well) at a volume of 70 μL were aliquoted to a 96-well plate, and immobilized thereto while culturing for 24 hours. On the next day, 30 μL of the antibodies were added to the culturing cells. The final concentration of the treated antibodies was at maximum 20 μg/mL per each antibody and sequentially diluted at a 1:4 ratio, and the assay was performed at 5 different concentrations. When treated in combination of trastuzumab, the ratio between the developed antibodies and trastuzumab was set at a 1:1 ratio (for example, in FIGS. 2A and 2B, when the amount of administration was 1 μg/mL, 1 μg/mL of TRA and 1 μg/mL of 1E11 were administered). After the treatment with the antibodies, BT-474 and NCI-N87 cells were cultured for 4 additional days, added with CCK-8 to a final concentration of 10%, and treated at 37° C. for 3 hours. Then, the absorbance of the treated cells was measured at 450 nm using Victor X-3. The absorbance of the cells not treated with the antibodies was set at 100%, and their relative viability was calculated (FIGS. 2A and 2B).

The developed 1E11 antibody showed an inhibitory effect against the proliferation of NCI-N87 (FIG. 2A) and BT-474 (FIG. 2B) cell lines, which were responsive to trastuzumab. Furthermore, the combined treatment of 1E11 antibody and trastuzumab showed a higher inhibitory activity against cancer cell proliferation than trastuzumab treatment alone, regarding the NCI-N87 and BT-474 cell lines. Interestingly, the combined treatment of 1E11 antibody and trastuzumab showed a higher inhibitory activity against cancer cell proliferation than the combined treatment of trastuzumab and pertuzumab, regarding the NCI-N87 cell line (FIG. 2A).

Example 6: Confirmation of Synergistic Effect of Developed Antibodies in Combination Treatment with Trastuzumab In order to confirm whether the anticancer effect of the combined treatment of the developed 1E11 antibody and trastuzumab in stomach cancer was synergistic effect, NCI-N87 cells were treated with 1E11 antibody or trastuzumab alone or in combination thereof the anticancer effects were analyzed (FIG. 2A). The anticancer effect according to concentration was analyzed via CalcuSyn program (Biosoft) using Chou & Talalay method (Chou et al., Adv. Enzyme. Regul. 22:27-55(1984)) which analyzes the effect of combined administration of at least two drugs (Table 4). When two drugs are administered in combination they either become agonistic, additive, or synergistic. The mutual interactions of drugs can be analyzed using Chou & Talalay method in terms of combination index (CI). The CI value of 1 or greater indicates an agonistic effect, while CI values of 1, and 1 or less indicate an additive effect, and a synergistic effect, respectively.

TABLE 4

| 1E11 + Trastuzumab | | | |
|---|---|---|---|
| C.I. | | | |
| ED50 | ED75 | ED90 | r |
| 0.0315 | 0.0459 | 0.0751 | 0.95921 |

In the above Table, ED50, ED75 and ED90 indicate the effective doses, which show effects in 50%, 75% and 90% populations, respectively. 'r' indicates a linear correlation coefficient of a median-effect plot.

As can be seen in FIG. 2A and Table 4, the CI value of the two drugs of trastuzumab and 1E11 clones at the time of their combined treatment was below 0.1, and thus the two antibodies were confirmed to have a synergistic effect when administered in combination.

Example 7: Comparison of Epitopes Between the Developed Antibodies and Trastuzumab Trastuzumab, the antibody to HER2, is known to bind to domain-4 among the four domains of the HER2 ECD. In order to confirm whether the epitopes on HER2 of the developed antibodies overlap with those of trastuzumab, an epitope binning was performed via surface plasmon resonance (SPR) using Biacore 3000 (GE Healthcare). About 1,000 RU (response unit) of trastuzumab was immobilized to a CM5 sensor chip (GE Healthcare, Cat. No. BR-1000-12) via an amine coupling method using ECD/NHS. HER2-ECD-His protein at a concentration of 320 nM was allowed to bind to the sensor chip, to which the trastuzumab was immobilized, using HBS-P buffer (10 mM HEPES, 150 mM NaCl, 1 mM EDTA, 0.005% Tween-20, pH 7.4) for 4 minutes, and only the buffer was flowed thereonto for 5 minutes thereafter to stabilize the binding between trastuzumab and HER2-ECD. Then, the secondary antibodies at a concentration of 1 μg/mL were allowed to bind thereto for 4 minutes, and the buffer was allowed to flow thereonto. In all experiments, the flow rate was set at 50 μL/min. If the secondarily bound antibodies further bind to the HER2-ECD protein, to which trastuzumab was bound, they are antibodies that do not share the common epitope with trastuzumab.

Figure 3A:
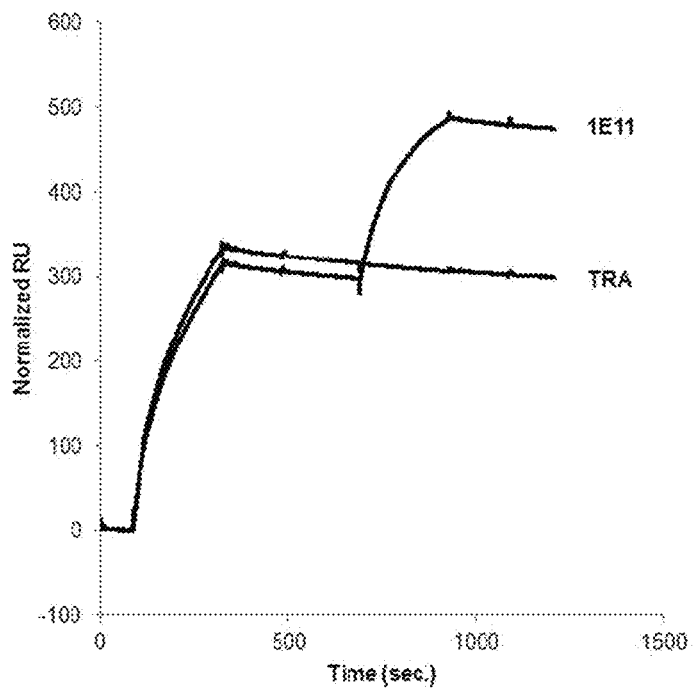
FIGS. 3A and 3B show that 1E11 antibody binds to a domain of HER2 sub-domain which is different from the binding domain of trastuzumab'.

As can be seen in FIG. 3A, hIgG, which was used as a secondary antibody, does not bind to HER2 and thus there was no additional binding, and since trastuzumab has the same epitope it did not bind further. In contrast, the 1E11 antibody was additionally bound to HER2-ECD, which was bound to trastuzumab, and thus it was confirmed to have an epitope which is different from that of trastuzumab.

Figure 3B:
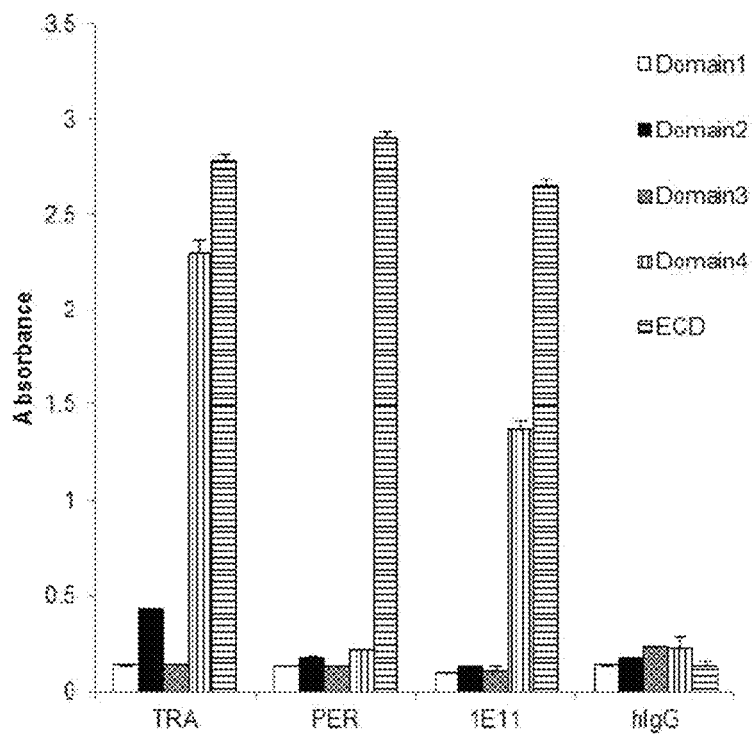

In order to confirm the domain region to which the 1E11 clones bind, the four sub-domains (domains 1-4) which constitute the extracellular domain of HER2 protein were individually produced using animal cells, to which the hinge region and the Fc region of human IgG1 were bound, and purified using Protein-A. The binding of the 1E11 clones, trastuzumab, pertuzumab was confirmed via ELISA assay regarding the thus-produced recombinant protein. As can be seen in FIG. 3B, the 1E11 clones were shown to bind to the sub-domain 4, as in the case with trastuzumab.

From the foregoing results, it was confirmed that 1E11 clones bind to the sub-domain 4 of ECD of the HER2 protein but they bind to an epitope which is different from that of trastuzumab (FIG. 3).

Example 8: Specificity of Developed Antibody to HER2

Whether the developed 1E11 antibodies bind specifically to HER2 among the ErbB family proteins, to which HER2 belongs, and whether they bind to HER2 of species other than humans were confirmed via ELISA assay. In order to confirm whether the developed 1E11 antibodies bind specifically to HER2 among the ErbB family proteins, the extracellular domains of EGFR, HER2, HER3 and HER4, which belong to the ErbB family, were examined via ELISA assay. The extracellular domains of EGFR (EGFR-ECD-Fc) were produced in the same manner as in HER2-ECD-Fc, and HER3 (R&D Systems, #348-RB-050) and HER4 (R&D Systems, #1131-ER-050) were purchased. In order to confirm whether the developed antibodies exhibit interspecific cross-reactions to HER2 proteins of different species, HER2 extracellular domains of humans, a rhesus monkey, a cynomolgus monkey, a mouse, and a rat were used and confirmed via ELISA assay. The extracellular domain of a cynomolgus monkey was produced in the same manner as in human HER2-ECD-Fc, and the HER2 extracellular domain of a rhesus monkey (Sino Biological Inc., #90020-K08H), the HER2 extracellular domain of a mouse (Sino Biological Inc., #50714-M08H), and the HER2 extracellular domain of a rat (Sino Biological Inc., #80079-R08H) were purchased.

Figure 4A:
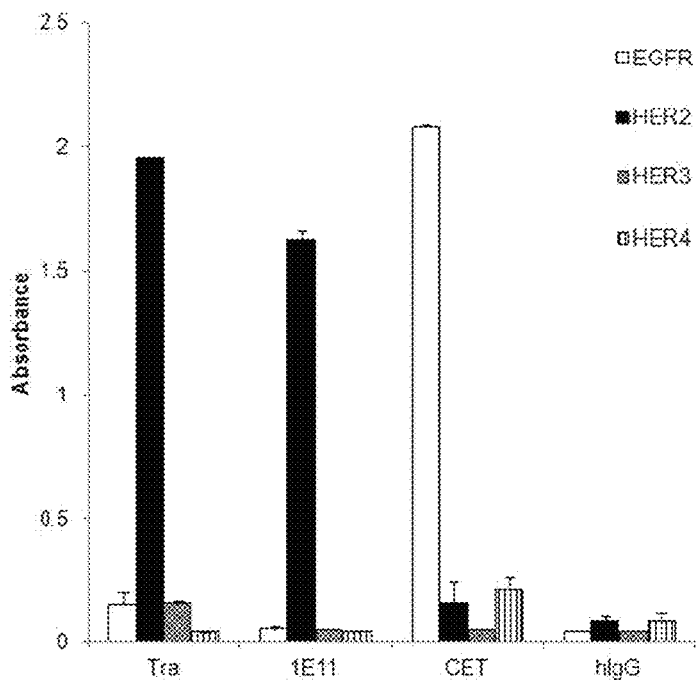
FIG. 4A shows the result of ELISA analysis to examine whether 1E11 antibody binds specifically to HER2 among ErbB family proteins to which HER2 belongs. Cetuximab (CET) was used as a control antibody against EGFR protein.
Figure 4B:
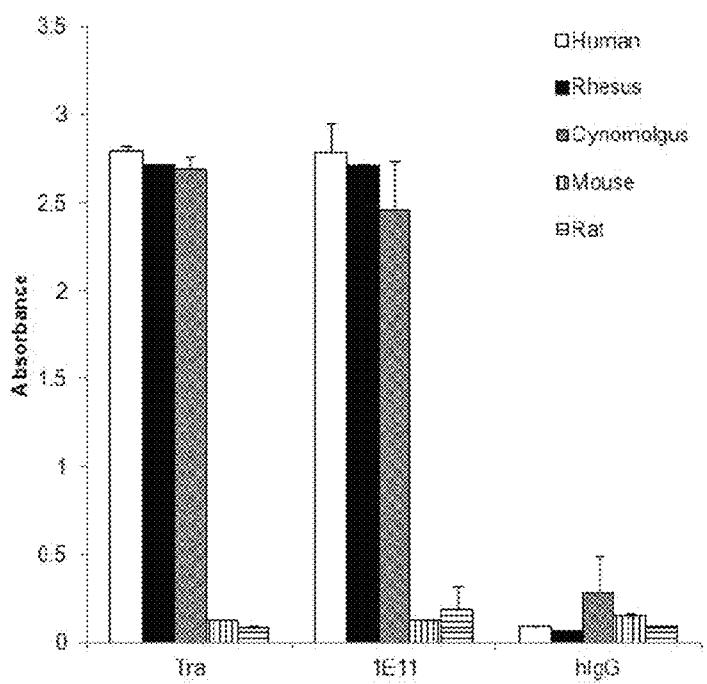
FIG. 4B shows the result of ELISA analysis to examine whether 1E11 antibody binds to HER2 other than humans.

As can be seen in FIGS. 4A and 4B, it was confirmed that the developed 1E11 antibodies specifically bind to HER2 among the human ErbB family proteins, and have interspecific cross-reactions to HER2 proteins of a rhesus monkey and a cynomolgus monkey.

Example 9: Apoptosis Analysis of HER2 Antibodies

Figure 5A:
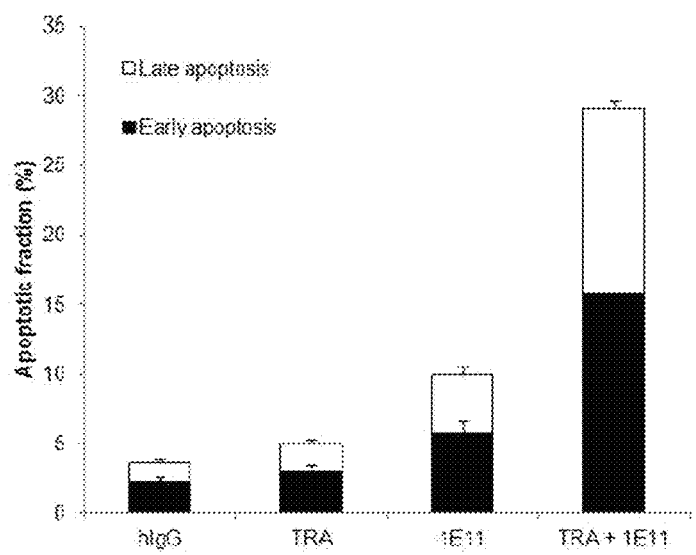
FIG. 5A shows the analysis result of the percentage of cancer cells where apoptosis occurred when NCI-N87 cells were treated with 1E11 antibody or trastuzumab alone or in combination thereof.
Figure 5B:
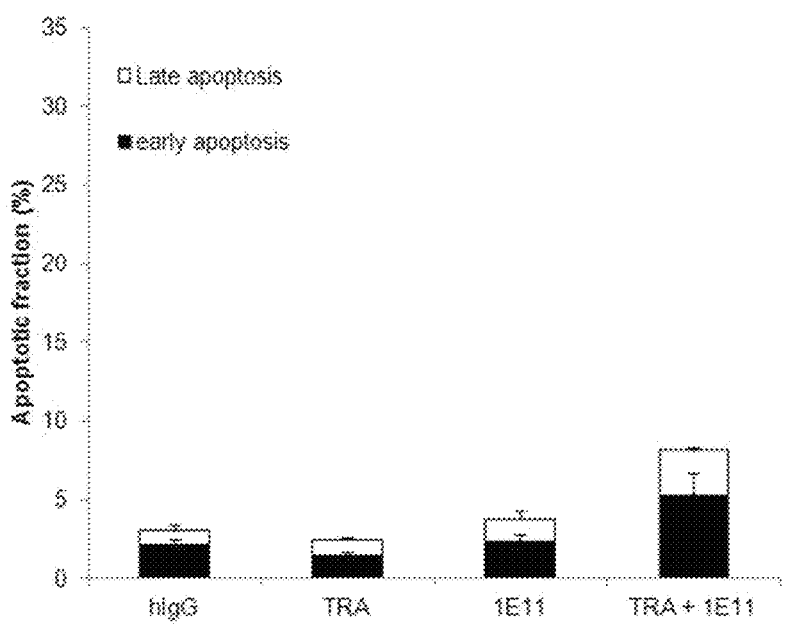
FIG. 5B shows the analysis result of the percentage of cancer cells where apoptosis occurred when BT-474 cells were treated with 1E11 antibody or trastuzumab alone or in combination thereof.

We analyzed apoptosis induction abilities of HER2 antibodies to elucidate an underlying molecular mechanism of anticancer effects of 1E11 antibody co-administered with trastuzumab. To investigate apoptosis induction abilities, NCI-N87 and BT-474 cells were treated with 10 µg/mL of 1E11 antibody, trastuzumab or its combination for 48 hr (10 µg/mL of 1E11 and 10 µg/mL of trastuzumab for combined administration). After the antibody treatment, cells were detached with trypsin and 500,000 cells were analyzed using ApoScreen Annexin V Apoptosis kit (SouthernBiotech, #10010-02) by a flow cytometry analysis (Cytomics FC500, Beckman Coulter Inc.) (FIGS. 5A and 5B).

Figure 5C:
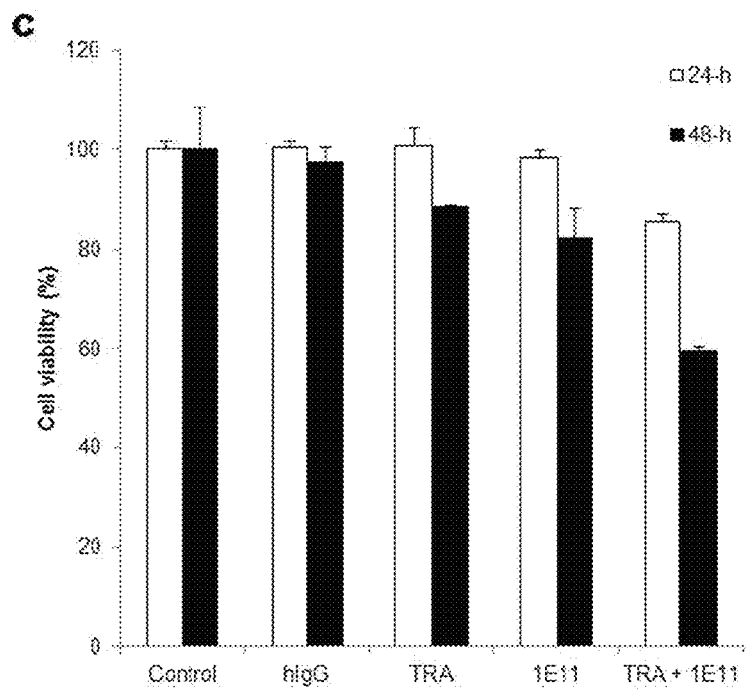
FIG. 5C shows the result of cell viability analyses 24 hours and 48 hours after treating NCI-N87 cells with 1E11 antibody or trastuzumab alone or in combination thereof. The control group shows the viability of cells treated with PBS only, the solvent for the antibodies.
Figure 5D:
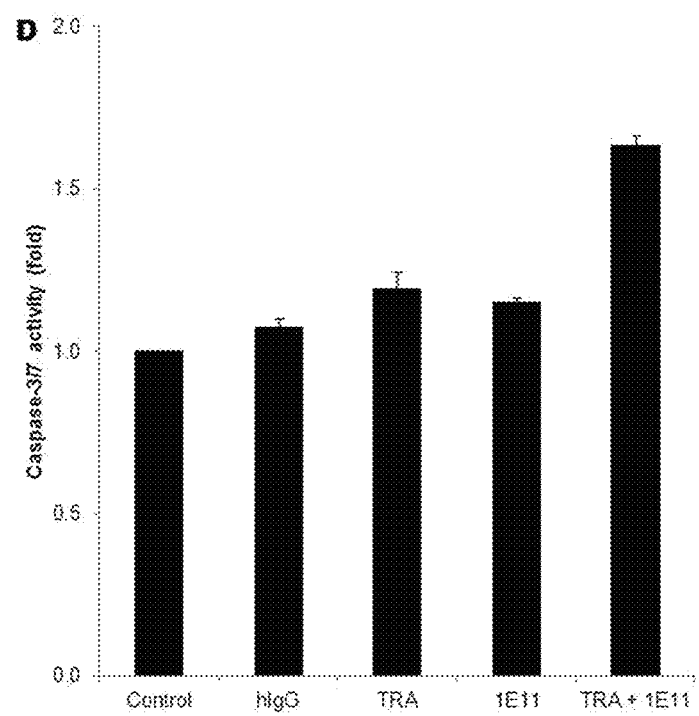
FIG. 5D shows the analysis result of Caspase-3/7 activity, 24 hours after treating NCI-N87 cells with 1E11 antibody or trastuzumab alone or in combination thereof. The control group shows the viability of cells treated with PBS only, the solvent for the antibodies.

To measure activities of caspase-3 and caspase-7 playing a crucial role in apoptosis, anticancer efficacies of 1E11 antibody, trastuzumab or combination thereof were analyzed over treatment time. NCI-N87 cells were treated with 10 µg/mL of antibodies. After 24 hr and 48 hr of the treatment, cell viability assay was performed using Caspase-Glo (Promega, #G7571) (FIG. 5C). It was shown that the cell viability was sharply decreased after 24 hr of the treatment. Based on such results, the activities of caspase-3/7 were measured after 24 hr of the treatment. NCI-N87 cells were treated with 10 µg/mL of antibodies for 24 hours. Caspase-Glo 3/7 Assay (Promega, #G809) was used to measure caspase-3/7 activity (FIG. 5D).

As represented in FIGS. 5a and 5b, 1E11 antibody alone was shown to exert apoptotic activity to HER2-overexpressing stomach cancer (NCI-N87 cells) and breast cancer (BT-474 cells), which are unlike trastuzumab. The apoptotic activity of 1E11 antibody was further increased with combined treatment with trastuzumab. The increased apoptotic activity of the combined treatment with 1E11 and trastuzumab was analyzed to be due to increase in caspase-3/7 activity playing a crucial role in apoptosis (FIG. 5D).

Example 10: HER2 Cell Signaling Inhibition by Antibodies

To elucidate the anticancer mechanism of 1E11 in combination with trastuzumab against HER2-overexpressing stomach cancer and breast cancer, we analyzed HER2 signaling activities in cells. NCI-N87 cells were treated with 10 µg/mL of antibodies for 24 hours. Then cells were lysed with cell lysis solution [50 mM Tris, pH 7.4, 150 mM NaCl, 1% NP-40, 0.1% sodium dodecyl sulfate, 1 mM NaF, 1 mM Na3VO4, 1 mM PMSF and protease inhibitor cocktail (Sigma)] for obtaining a cell lysate. The cell lysate underwent the Western blot analysis. HER2 (#4290), pHER2 (#2243), pHER3 (#4791), EGFR (#4267), pEGFR (#3777), AKT (#4691), pAKT (#4060), ERK (#4695), and pERK (#4370) antibodies were purchased from Cell Signaling Technology. HER3 (sc-285) antibody was purchased from Santa Cruz Biotechnology and GAPDH (AbC-1001) antibody as a loading control was purchased from AbClon. The horseradish peroxidase-conjugated anti-mouse (AbC-5001) and anti-rat (AbC-5003) antibodies were also purchased from AbClon. The bands were visualized using AbSignal (AbClon, AbC-3001).

We further examined whether the combined treatment of 1E11 and trastuzumab inhibits heterodimerization between HER2 and EGFR or HER3 as another ErbB family proteins. NCI-N87 cells were treated with EGF for induction of heterodimerization between HER2 and EGFR, and treated with HRG for induction of heterodimerization between HER2 and HER3. NCI-N87 cells were aliquoted in a cell medium supplemented with 0.1% FBR and cultured for 24 hr. Then, the cells were treated with 10 µg/mL of antibodies for 1 hr, and then with 200 ng/mL of EGF (R&D Systems, #236-EG-200) or HRG (R&D Systems, #377-HB/CF). Three-day later, the cell viability was tested.

Figure 6A:
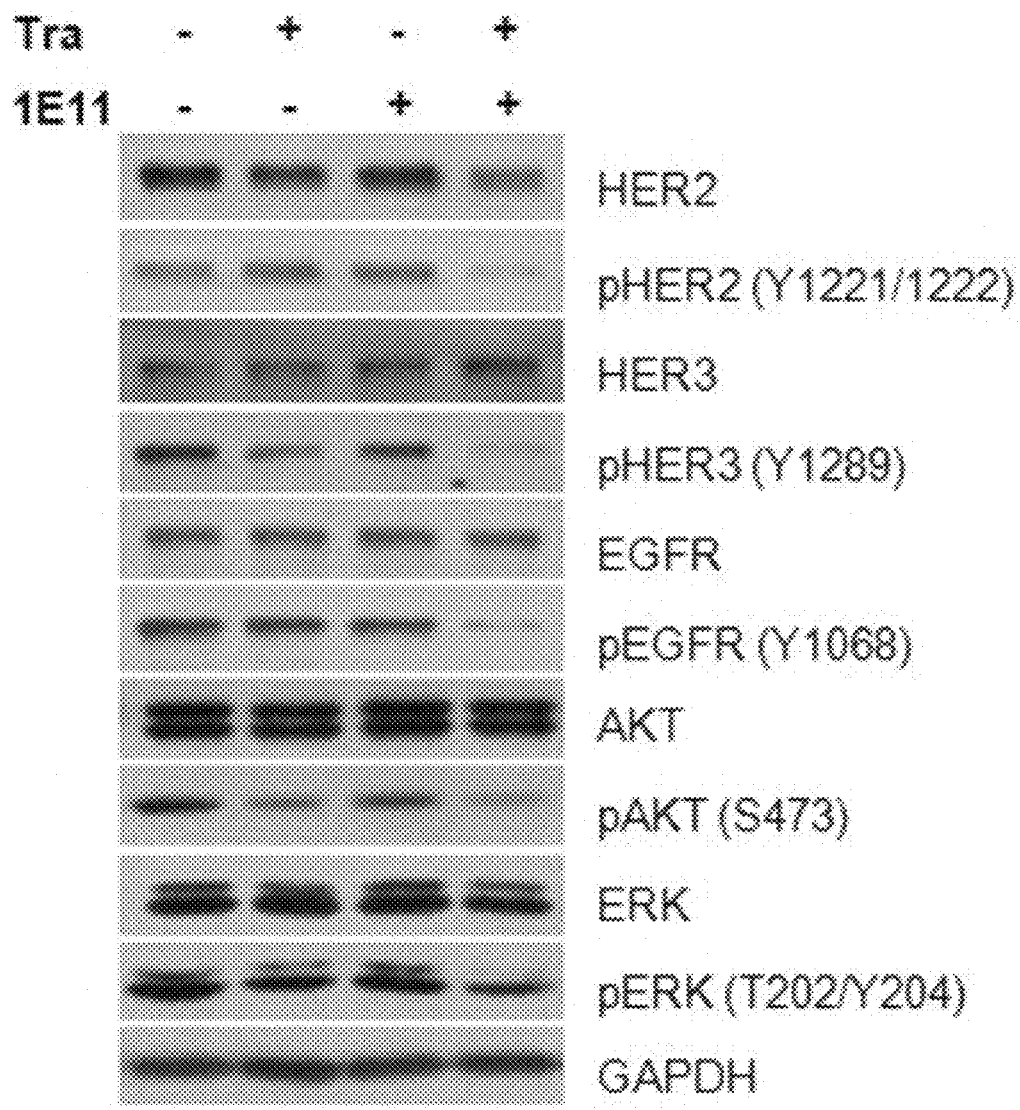
FIG. 6A shows the result of western blot analysis illustrating the decrease in HER2 downstream signaling by treatment with 1E11 antibody or trastuzumab alone or in combination thereof.

As shown in FIG. 6a, the combined treatment of 1E11 and trastuzumab contributes to decrease in level of the HER2 protein. Upon decrease in level of the HER2 protein, the phosphorylated HER2 protein was also decreased. We observed reduced phosphorylated HER3 and EGFR level without total protein level change. Such results demonstrate that the combined treatment of 1E11 and trastuzumab is able to control activities of HER2, HER3 and EGFR. By such activity controls, activities of AKT and ERK, well-known HER2 downstream factors, were also altered without total protein level change.

Figure 6B:
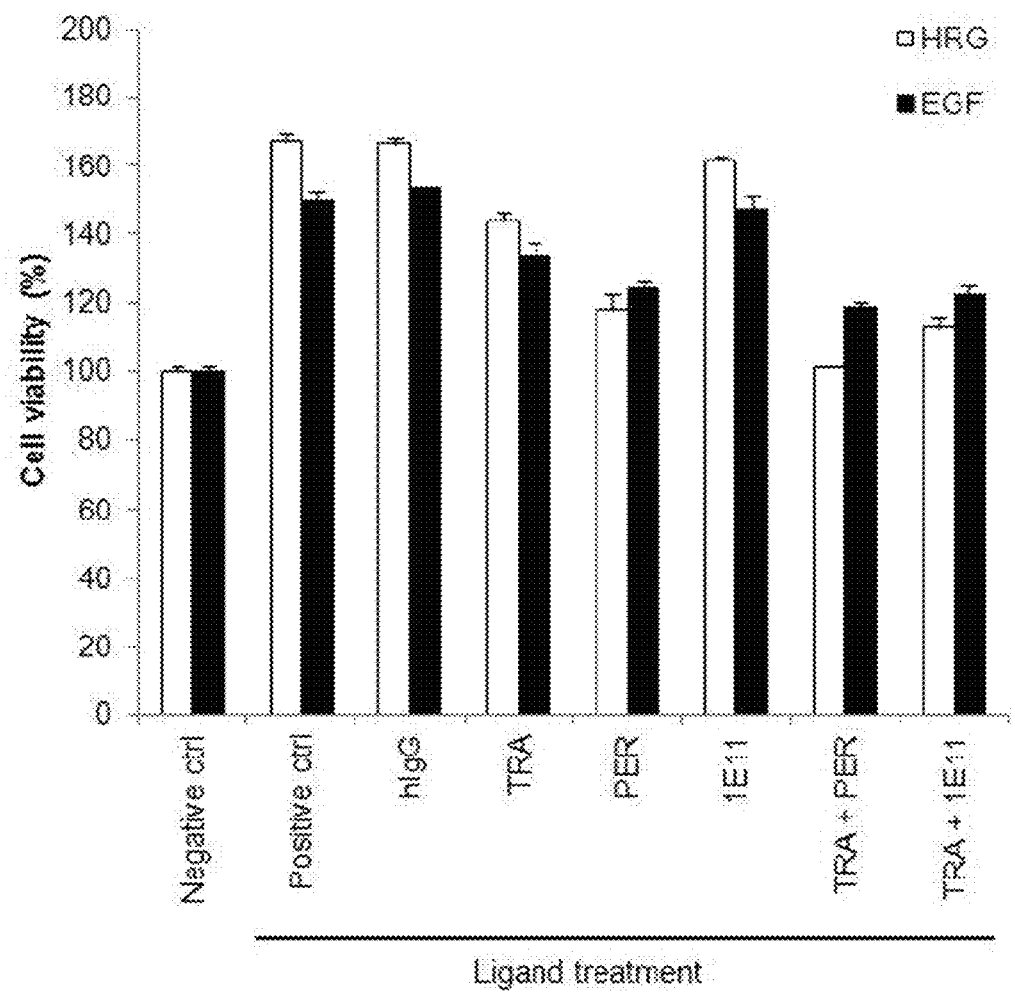
FIG. 6B is a graph showing the inhibitory effect for the heterodimerization-induced cell proliferation by the treatment with 1E11 antibody or trastuzumab alone or in combination thereof. A negative control (Negative ctrl) shows the viability of cells neither treated with ligands nor antibodies, and a positive control (Positive ctrl) shows the viability of cells treated with ligands only without treatment with antibodies.

It was shown that the combined treatment of 1E11 and trastuzumab resulted in reduction of cell proliferation by heterodimerization between HER2 and EGFR (or HER3) (FIG. 6b). NCI-N87 cell proliferation by EGF capable of inducing heterodimerization between HER2 and EGFR, and HRG capable of inducing heterodimerization between HER2 and HER3, was reduced by the combined treatment of 1E11 and trastuzumab to a similar level to pertuzumab known to inhibit HER2 binding to other receptors.

These results address that cell signaling through heterodimerization between HER2 and EGFR (or HER3) was suppressed by the combined treatment of 1E11 and trastuzumab.

Example 11: Anticancer Efficacies of Antibodies in Animal Models

The anticancer efficacies of 1E11 antibody were evaluated using animal models. Athymic nude female mice (Daehan Biolink, Korea) were injected subcutaneously with $5\times10^6$ of NCI-N87 cells to prepare xenograft model. Tumors were allowed to grow about 200 mm$^3$ in size, and mice were then randomized into four groups. Animals of the four groups received twice weekly intraperitoneal administration of 10 mg/kg of palivizumab (as isotype control of trastuzumab (MedImmune LLC.)), 1E11, trastuzumab, and combination of 1E11 and trastuzumab, respectively. For combined administration, each antibody was administered in a dose of 10 mg/kg. Tumor volumes were measured over time. On day 22, the animals were sacrificed and the tumors were isolated. Tumor volumes were calculated using the formula (L*W*W)/2, where "L" represents the larger tumor diameter and "W" represents the smallest tumor diameter. The isolated tumors were weighed and prepared for immunohistochemistry analyses. Tumor xenograft tissues were processed as formalin-fixed and paraffin-embedded specimen sections. These were examined by hematoxylin (DAKO, #CS700) and eosin (DAKO, #CS701) (H&E) staining and HER2 protein staining using HER2 antibody (Cell Signaling Technology, #4290).

Figure 7A:
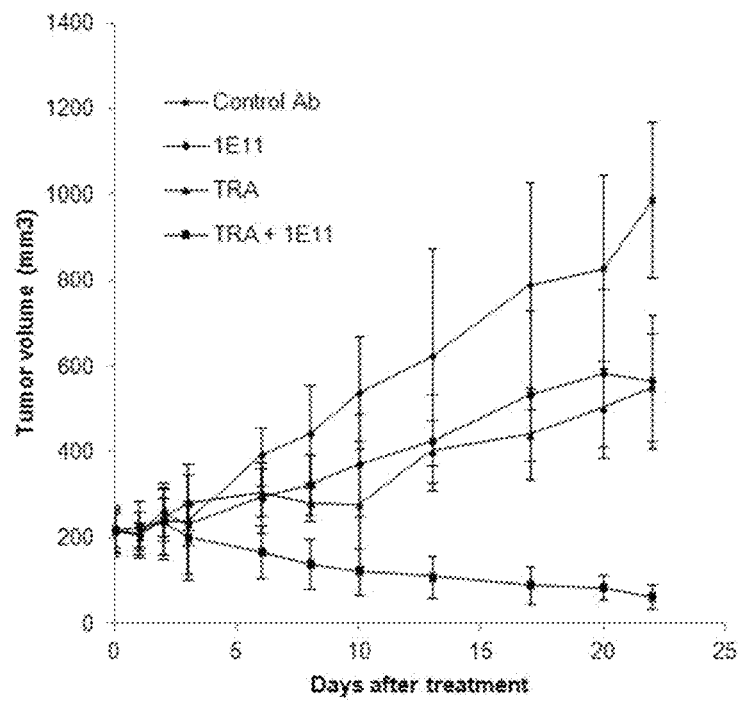
Figure 7B:
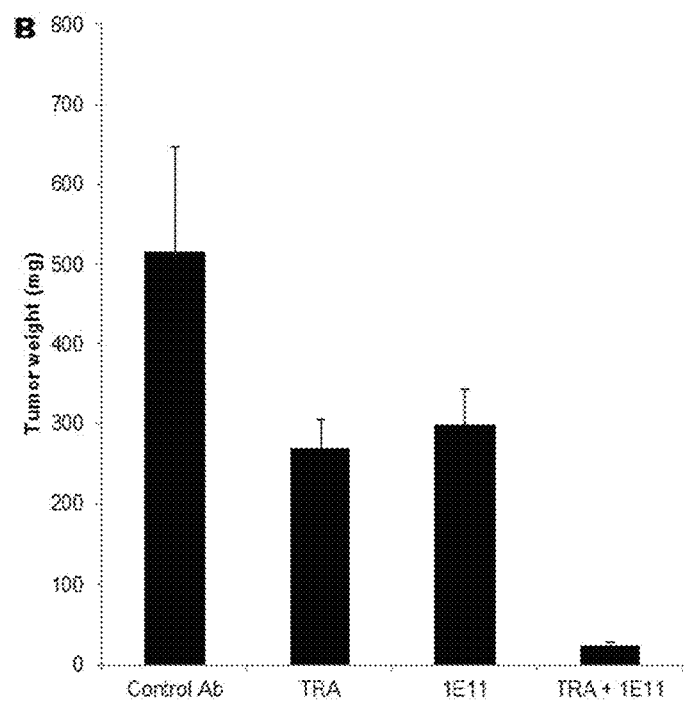

1E11 alone inhibited tumor growth to an extent similar to trastuzumab (FIG. 7a). 1E11 showed dramatically increased antitumor activity in combination with trastuzumab compared with each single antibody treatment. The antitumor activity was also confirmed by analyzing tumor mass extracted after experiments (FIG. 7b). The reduction of HER2-expressing cells by the combined treatment of 1E11 and trastuzumab was observed in immunohistochemistry staining (FIG. 7c), which is compatible with results of the Western blotting (FIG. 6a). These results indicate that 1E11 in combination with trastuzumab dramatically inhibits tumor growth compared with single antibody treatment, which is due to suppression of expression of the HER2 protein.

Example 12: Development of Humanized Antibodies and Confirmation of their Effects The humanized antibodies of the chimeric 1E11 antibodies developed in Example 4 were developed using a CDR grafting method. Regarding the human antibodies to receive the CDR of the developed antibodies, V and J genes of human germline antibody genes with high nucleotide sequence based-homology were selected using IMGT/V-QUEST (Brochet, X. et al., Nucl Acids Res. 36:503-508 (2008)). As a V gene and a J gene of a heavy chain, IGHV3-48*03 gene and IGHJ4*01 gene were selected, respectively, and their sequence homology was 85.07% and 87.23%, respectively. Additionally, as a V gene and a J gene of a light chain, IGKV1-39*01 gene and IGKJ1*01 gene were selected, respectively, and their sequence homology was 81.36% and 81.08%, respectively. Considering a report that grafting of CDR only decreases affinity, H49 based on the Kabat numbering of the heavy chain corresponding to the Vernier zone that can affect the entire structure of an antibody was replaced with alanine instead of serine, which is on the human germline gene. The developed humanized antibody hz1E11 was produced in the form of IgG using FreeStyle™ 293F cell line. The amino acid sequences of the heavy chain variable region and the light chain variable region of the developed hz1E11 are described in SEQ ID NOS: 24 and 26, respectively.

The affinity of hz1E11, the developed humanized antibody of 1E11, for HER2 was measured via surface plasmon resonance (SPR) assay. All the experiments were performed using Biacore 3000. First, the goat antibodies to human IgG were immobilized at a concentration of 1000 RU to a CM5 sensor chip via an amine coupling method. Trastuzumab, pertuzumab, and hz1E11 were respectively diluted to 2.84 µM, 5.68 µM, and 7.1 µM using a HBS-P buffer. Before binding to HER2-ECD-His protein, each antibody was bound at a rate of 50 µL/min for 180 seconds, and allowed the buffer to flow thereonto for stabilization purpose. Then, HER2-ECD-His protein was allowed to bind at concentrations of 640 nM, 320 nM, 160 nM, 80 nM, 40 nM, 20 nM, and 0 nM for 4 minutes, and allowed the buffer to flow thereonto for 15 minutes. The sensor chip was recycled by allowing 10 mM Glycine-HCl (pH 1.5) buffer to flow thereonto. All the sensorgram data was analyzed via a 1:1 interaction model using BIAevaluation software. The affinities of antibodies are summarized in Table 5 below. The affinities of trastuzumab and pertuzumab were 1.94 nM and 1.89 nM, respectively, whereas the affinity of the developed antibody 1E11 was 16.0 nM. The affinity of the humanized antibody of 1E11 was 10.4 nM, showing almost no difference from the existing 1E11 antibody.

TABLE 5

| Antibodies | Ka (M-1s-1) | Kd (s-1) | KD (nM) |
| --- | --- | --- | --- |
| Trastuzumab | 3.9E+04 | 7.6E−05 | 1.94 |
| Pertuzumab | 3.6E+04 | 6.8E−05 | 1.89 |
| 1E11 | 3.0E+04 | 4.7E−04 | 16.0 |
| hz1E11 | 4.9E+04 | 5.1E−04 | 10.4 |

Figure 8A:
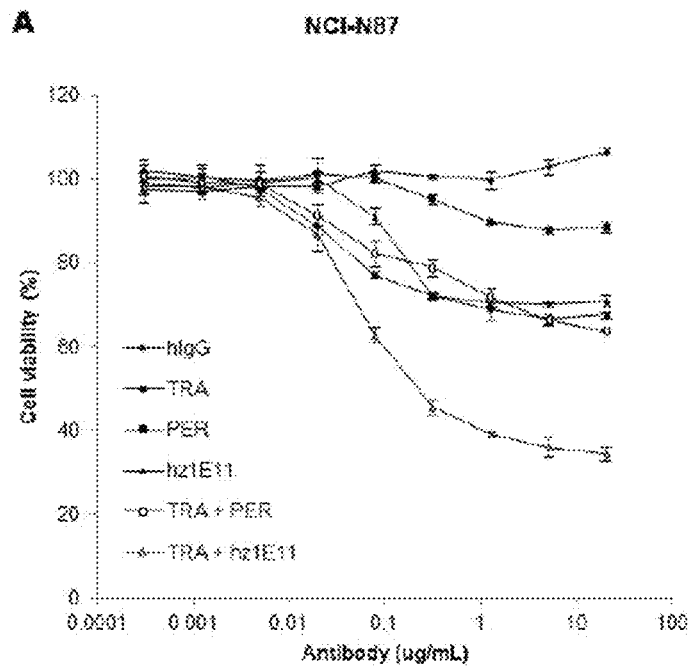
FIGS. 8A and 8B are graphs respectively showing the proliferation inhibitory effects for NCI-N87 cancer cell line and OE-19 cancer cell line, by a single treatment with hz1E11 antibody, which is a humanized antibody, and a combined treatment of hz1E11 antibody and trastuzumab.
Figure 8B:
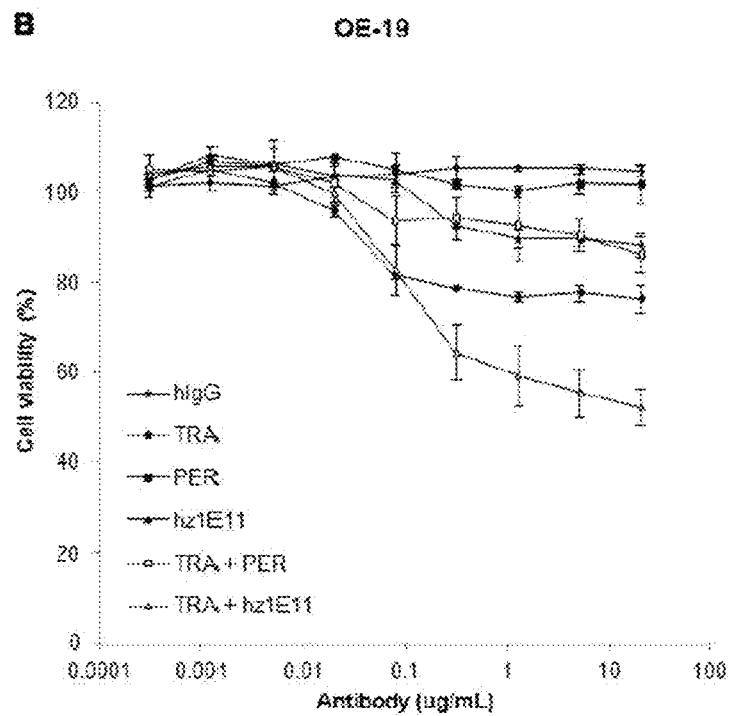

The anticancer effect of hz1E11, the developed humanized antibody of 1E11, was confirmed in human stomach cancer cell lines NCI-N87 and OE-19, which overexpress HER2 (FIG. 8). The single treatment of hz1E11 in NCI-N87 cells showed a decrease in cancer survival rate similar to that of trastuzumab treatment, whereas the combined treatment of hz1E11 and trastuzumab showed a significantly higher decrease in cancer survival rate compared to the single treatment by either antibody (FIG. 8A). Additionally, the combined treatment of hz1E11 and trastuzumab in OE-19, a different human stomach cancer cell line, showed a higher decrease in cancer survival rate compared to the single treatment by either antibody (FIG. 8B). Additionally, the combined treatment of hz1E11 and trastuzumab showed a bit higher inhibitory effect than the combined treatment of 1E11 and trastuzumab (FIG. 2A) against the proliferation of cancer cells (FIG. 8A). The combined treatment of hz1E11 and trastuzumab showed a higher inhibitory effect in NCI-N87 OE-19 cell lines than the combined treatment of trastuzumab and pertuzumab against the proliferation of cancer cells.

The above results indicate that the hz1E11, the developed humanized antibody of 1E11, has an equal binding capacity and a bit improved anticancer effect as compared to the conventional 1E11.

Figure 9:
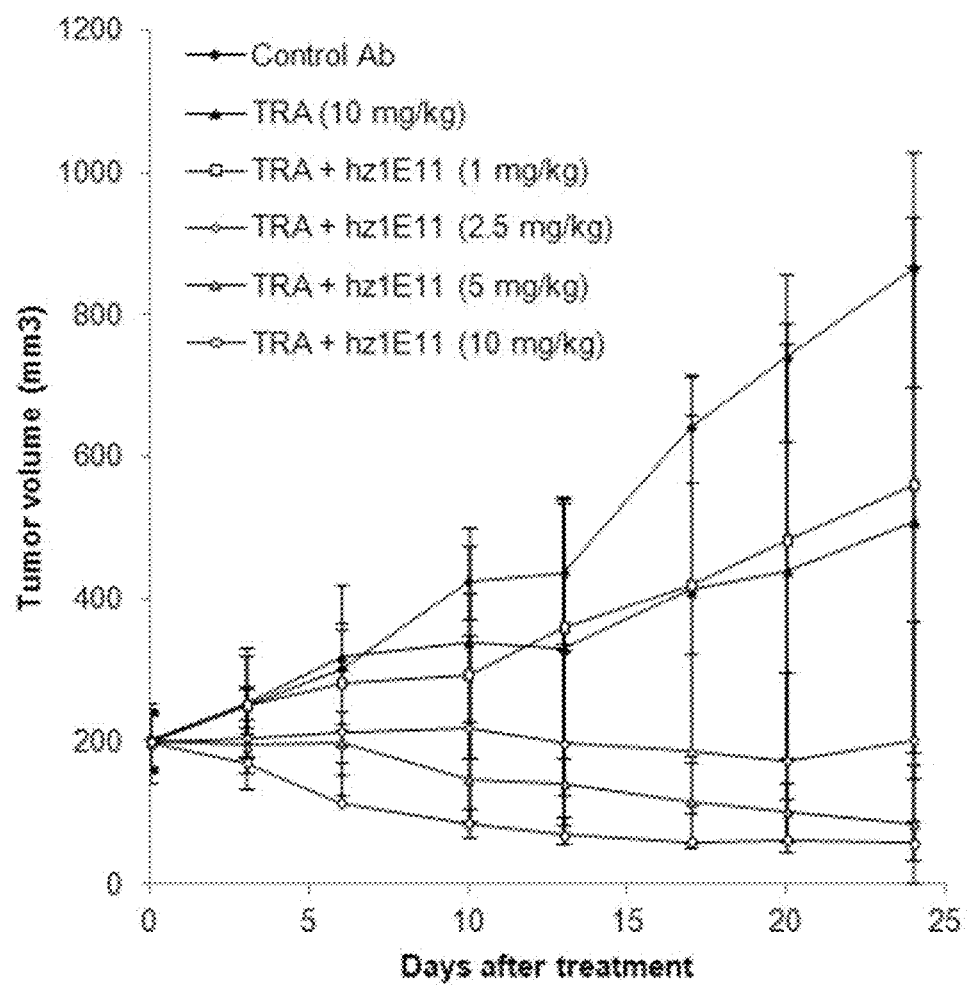
FIG. 9 shows the tumor cell growth inhibitory effect in an NCI-N87 xenograft animal model by the treatment with hz1E11 antibody or trastuzumab alone or in combination thereof. Control Ab is palivizumab.

The anticancer effect of the combined treatment of the hz1E11, the developed humanized antibody of 1E11, along with trastuzumab was confirmed in a xenograft model using NCI-N87. The mice having a cancer formed via NCI-N87 transplantation were intraperitoneally injected twice a week with the developed antibody and an isotype control group of trastuzumab, hz1E11, trastuzumab, and a combination of hz1E11 and trastuzumab, respectively. The isotype control group and trastuzumab were administered at a dose of 10 mg/kg. In the case of a combined treatment, hz1E11 and trastuzumab were mixed at a 1:1 ratio, and administered at a dose of 1 mg/kg, 2.5 mg/kg, 5 mg/kg and 10 mg/kg based on each antibody. The combined treatment of hz1E11 and trastuzumab showed a decrease of cancer growth in a dose-dependent manner (FIG. 9). The anticancer effect observed with administration of 10 mg/kg of trastuzumab was also observed with administration of 1 mg/kg of hz1E11 or trastuzumab. The administration of hz1E11 and trastuzumab in a dose of greater than 5 mg/kg was shown to not only inhibit the growth of cancer but also decrease the cancer already formed.

Example 13: Confirmation of Binding Region of Developed Antibodies

In order to confirm the important region of the developed antibodies for binding to antigens, an alanine scanning assay which examines the binding capacity by changing the amino acids corresponding to CDR3 of the heavy chain and the light chain to alanine was performed. Histidine (H), leucine (L), glycine (G), glycine (G), threonine (T) and serine (S) among the CDR3 region of the heavy chain which correspond to 95, 96, 97, 98, 99 and 100a according to the Kabat numbering, and glutamine (Q), glutamine (Q), leucine (L), tyrosine (Y), serine (S) and threonine (T) among the CDR3 region of the light chain which correspond to 89, 90, 91, 92, 93 and 94 according to the Kabat numbering, were changed to alanine using the QuikChange Site-directed Mutagenesis kit (Stratagene, #200518). Among the CDR3 of the heavy chain, A100 was excluded from the assay because the developed antibody has alanine. After expressing each modified antibody in bacteria, its expression was confirmed via a dot-blot after obtaining a periplasmic extract therefrom, and the binding capacity was analyzed regarding the HER2-ECD via ELISA assay (see: FIG. 10).

TABLE 6

|  | Mutated sequence | Mutated position | Binding capacity to Her2-ECD (absorbance at 450 nm) |
|---|---|---|---|
| CDR-L3 | AQLYSTPWT (SEQ ID NO: 33) | Q89A | 1.711 |
|  | QALYSTPWT (SEQ ID NO: 34) | Q90A | 1.705 |
|  | QQAYSTPWT (SEQ ID NO: 35) | L91A | 1.492 |
|  | QQLASTPWT (SEQ ID NO: 36) | Y92A | 1.803 |
|  | QQLYATPWT (SEQ ID NO: 37) | S93A | 1.733 |
|  | QQLYSAPWT (SEQ ID NO: 38) | T94A | 1.628 |
| CDR-H3 | ALGGTASFDY (SEQ ID NO: 27) | H95A | 1.59 |
|  | HAGGTASFDY (SEQ ID NO: 28) | L96A | 1.66 |
|  | HLAGTASFDY (SEQ ID NO: 29) | G97A | 1.08 |
|  | HLGATASFDY (SEQ ID NO: 30) | G98A | 0.051 |
|  | HLGGAASFDY (SEQ ID NO: 31) | T99A | 0.839 |
|  | HLGGTAAFDY (SEQ ID NO: 32) | S100aA | 1.597 |
|  | Parent Antibody | hz1E11 | 1.75 |

Figure 10A:
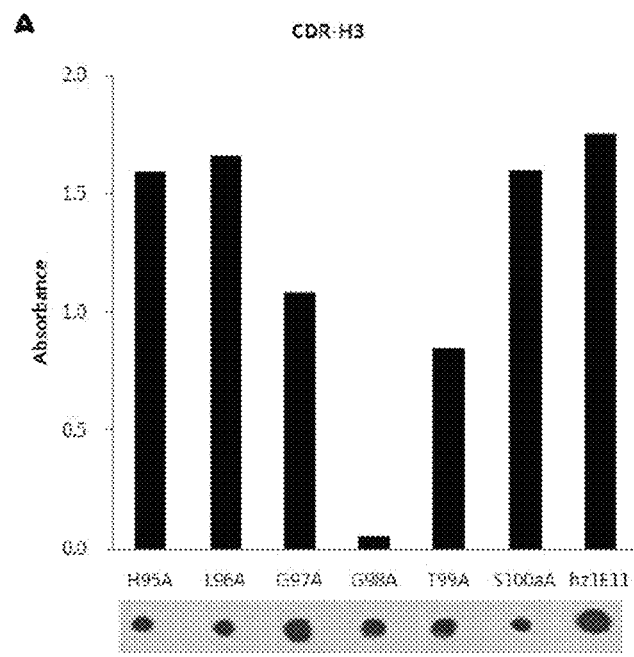
FIGS. 10A and 10B respectively show alanine scanning results of CDRH3 and CDRL3 of the hz1E11 antibody.
Figure 10B:
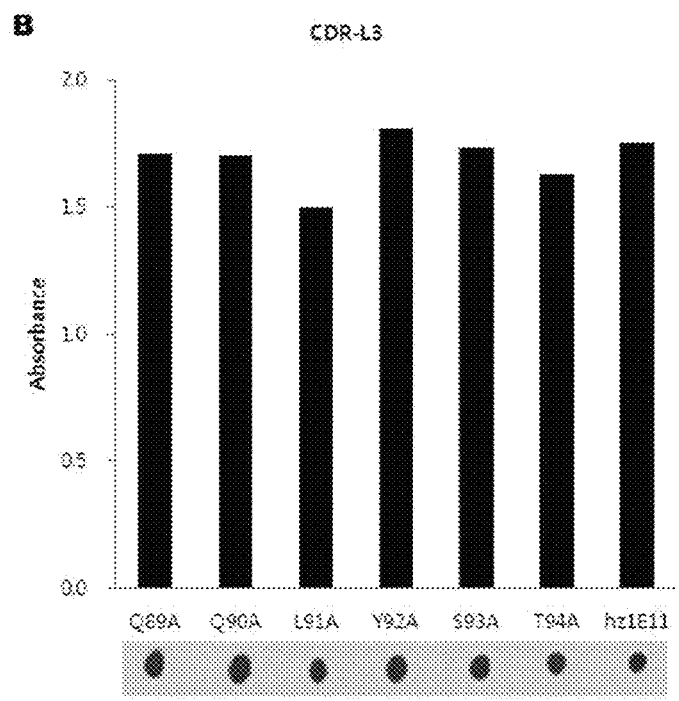
Figure 11A:
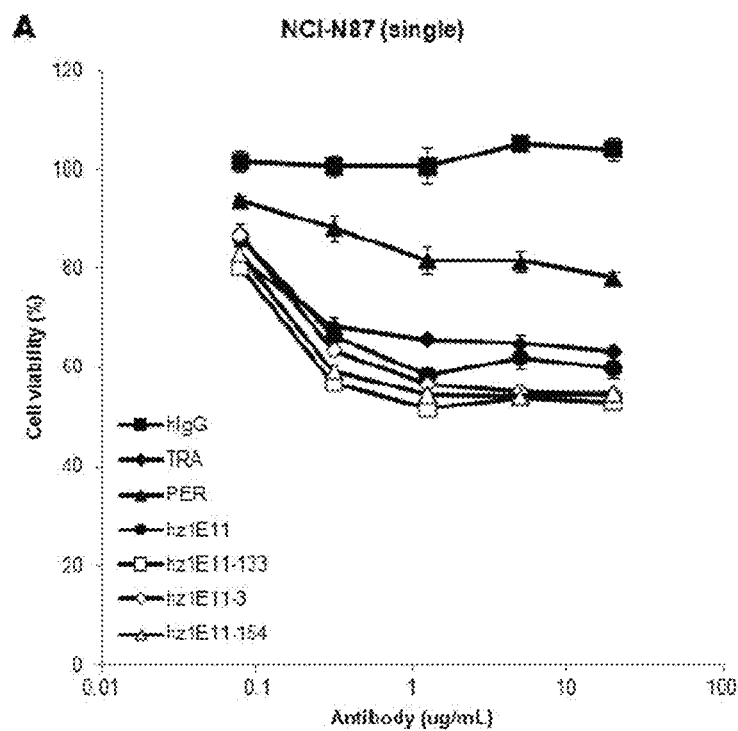
FIGS. 11A through 11F are graphs showing the proliferation inhibitory effects for NCI-N87, OE-19, and BT-474 cancer cell lines by a single treatment with hz1E11-3, hz1E11-133, and hz1E11-154 antibodies, which are affinity-improved humanized antibodies, and a combined treatment of trastuzumab therewith.
Figure 11B:
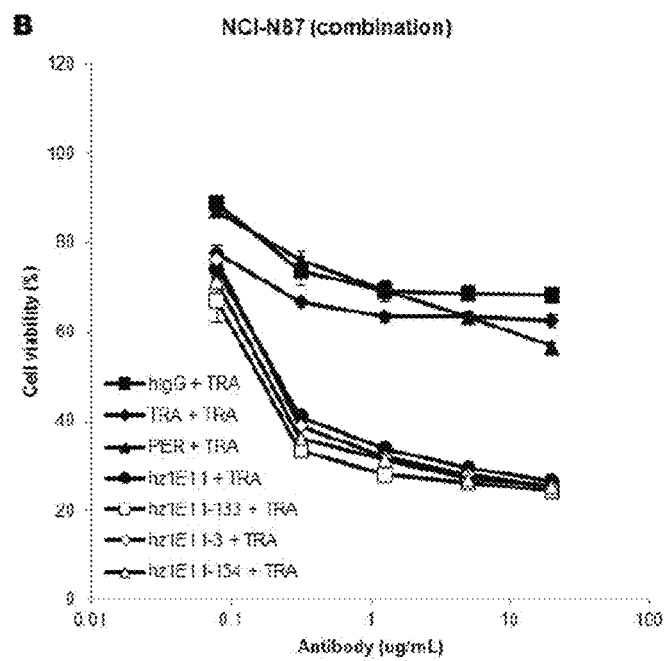
Figure 11C:
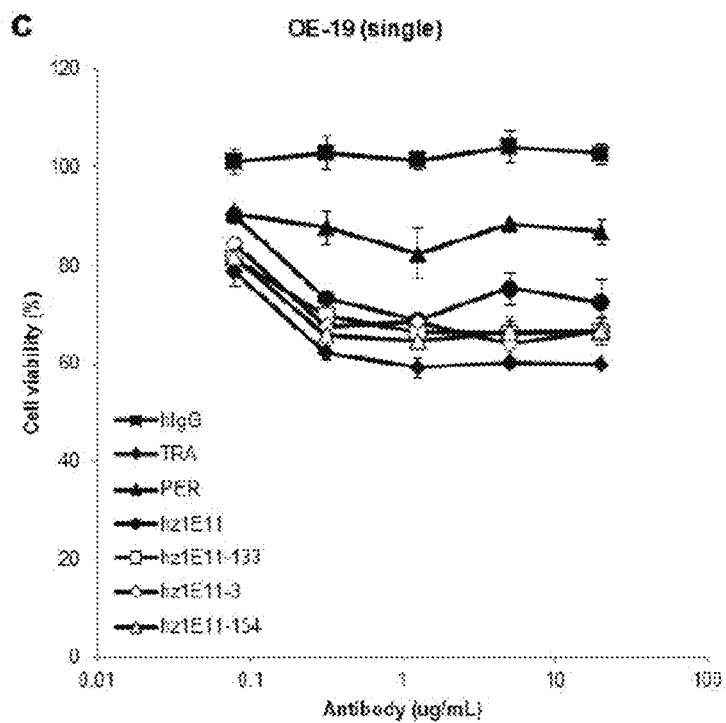
Figure 11D:
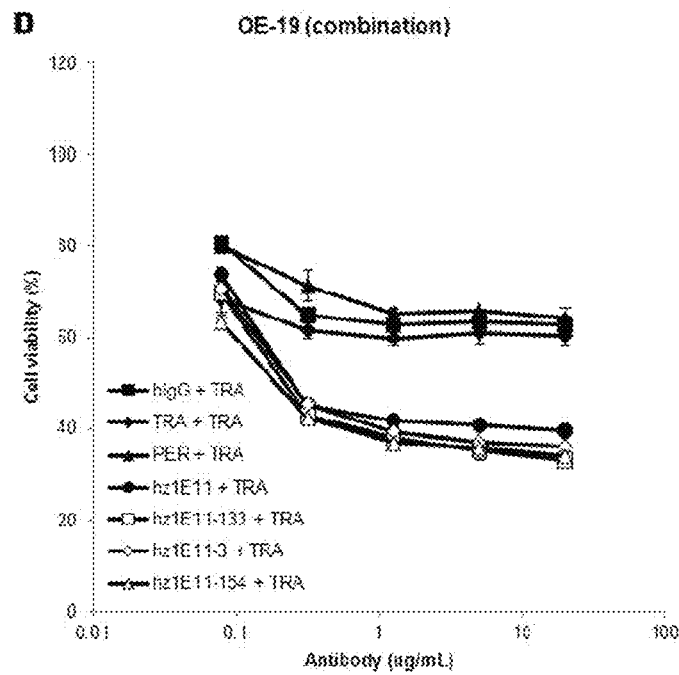
Figure 11E:
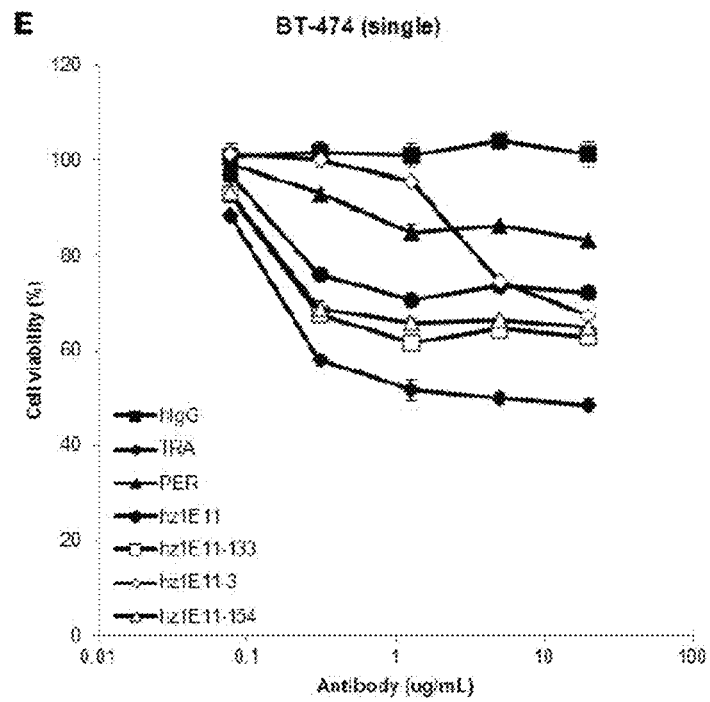
Figure 11F:
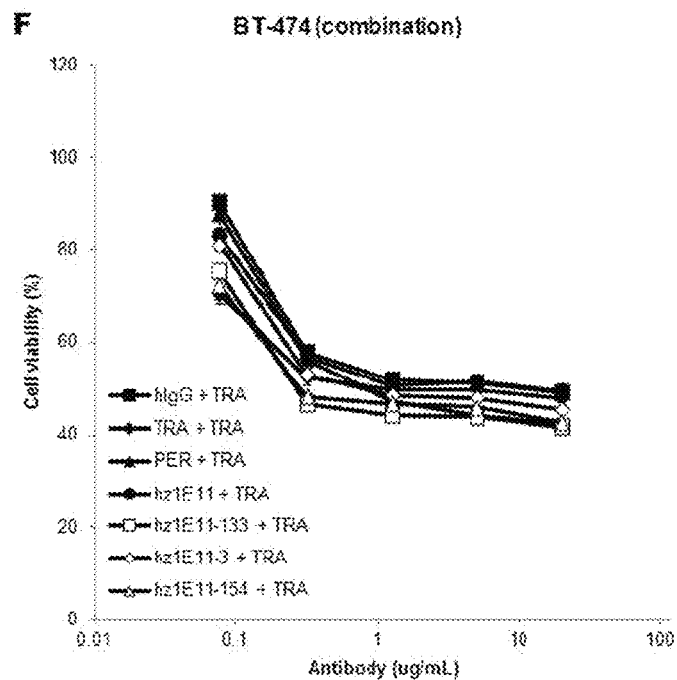

As can be seen in Table 6 and FIGS. 10A and 10B, the modified antibodies were expressed in a similar level, whereas G98A of the heavy chain showed a complete loss of its binding capacity, and G97A of the heavy chain showed a marked decrease in its binding capacity. The change in other regions did not show any noticeable effect on the antigen-antibody binding.

Example 14: Improvement of Affinities of Developed Antibodies

In order to improve the affinities of the developed antibodies, a library with randomized CDR3 of the light chain and the heavy chain was developed. F, D, and Y among the CDR3 of the heavy chain which correspond to F100b, D101, and Y102, the amino acid numbers according to the Kabat numbering, and P, W, and T among the CDR3 of the light chain which correspond to P95, W96, and T97 according to the Kabat numbering were excluded from the randomization because they are commonly discovered amino acids in human antibodies. A phage antibody library with 20 randomized amino acids of CDR3 amino acids of the heavy chain and the light chain exclusive of the amino acids described in the above technology was developed (Phage display: a laboratory manual, Carlos Barbas III, et al., Cold Spring Harbor Laboratory Press). In particular, the primers used above relate to the region corresponding to CDR3 of the heavy chain and the light chain, and were synthesized such that adenine (A), cytosine (C), guanine (G) and thymine (T) were mixed in an equal ratio to be inserted randomly into the first and second positions of the codon corresponding to the amino acid to be randomized, and guanine (G) or cytosine (C) were mixed in an equal ratio to be inserted into the third position.

In order to select the clones with improved affinities from the developed library, the HER2-ECD-His protein was biotinylated using the EZ-Link Sulfo-NHS-LC-Biotinylation kit (Thermo Scientific, #21435), and used as antigens for selecting antibodies. The developed phage antibody library and biotin-HER2-ECD-His protein were allowed to bind at room temperature for 2 hours, and the phages bound to the antigens were separated using 50 μL of Dynabeads M-270 Streptavidin (Invitrogen, #653.06). The above selection process was performed 4 times, and the colonies that expressed antibodies that bind to HER2-ECD among the thus-selected colonies were selected via ELISA assay using periplasmic extracts, and the sequences of the antibodies expressed in the selected colonies were confirmed via nucleotide analysis. The amino acid sequences of CDR3 of the heavy chain and the light chain of the antibodies that bind to HER2-ECD are summarized in Tables 7 and 8 below. The number 1 in each Table represents the amino acid sequence of CDR3 of the heavy chain and the light chain of hz1E11.

TABLE 7

| CDRH3 sequences of mutants selected from the process of improving affinity | |
|---|---|
| 1 | HLGGTASFDY (SEQ ID NO: 3) |
| 2 | AFGGTASFDY (SEQ ID NO: 39) |
| 3 | DLGGTASFDY (SEQ ID NO: 40) |
| 4 | FWGGTASFDY (SEQ ID NO: 41) |
| 5 | HCGGTASFDY (SEQ ID NO: 42) |
| 6 | HFGGTASFDY (SEQ ID NO: 43) |
| 7 | HHGGTASFDY (SEQ ID NO: 44) |
| 8 | HIGGTASFDY (SEQ ID NO: 45) |
| 9 | HLCSTASFDY (SEQ ID NO: 46) |
| 10 | HLCVTASFDY (SEQ ID NO: 47) |
| 11 | HLGGAASFDY (SEQ ID NO: 48) |
| 12 | HLGGLPSFDY (SEQ ID NO: 49) |
| 13 | HLGGMASFDY (SEQ ID NO: 50) |
| 14 | HLGGMSSFDY (SEQ ID NO: 51) |
| 15 | HLGGMTSFDY (SEQ ID NO: 52) |
| 16 | HLGGSSSFDY (SEQ ID NO: 53) |
| 17 | HLGGTACFDY (SEQ ID NO: 54) |
| 18 | HLGGTGAFDY (SEQ ID NO: 55) |
| 19 | HLGGTGSFDY (SEQ ID NO: 56) |
| 20 | HLGGTSTFDY (SEQ ID NO: 57) |
| 21 | HLGGTTSFDY (SEQ ID NO: 58) |

TABLE 7-continued

CDRH3 sequences of mutants selected from the process of improving affinity

| | |
|---|---|
| 22 | HLGSTASFDY (SEQ ID NO: 59) |
| 23 | HLYRTASFDY (SEQ ID NO: 60) |
| 24 | HMGGTASFDY (SEQ ID NO: 61) |
| 25 | HRGGTASFDY (SEQ ID NO: 62) |
| 26 | HVGGTASFDY (SEQ ID NO: 63) |
| 27 | HWGGTASFDY (SEQ ID NO: 64) |
| 28 | HYGGTASFDY (SEQ ID NO: 65) |
| 29 | MNGGTASFDY (SEQ ID NO: 66) |
| 30 | NFGGTASFDY (SEQ ID NO: 67) |
| 31 | NHGGMASFDY (SEQ ID NO: 68) |
| 32 | NHGGTASFDY (SEQ ID NO: 69) |
| 33 | NIGGTASFDY (SEQ ID NO: 70) |
| 34 | NLGGTASFDY (SEQ ID NO: 71) |
| 35 | NMGGTASFDY (SEQ ID NO: 72) |
| 36 | NNGGTASFDY (SEQ ID NO: 73) |
| 37 | NWGGTASFDY (SEQ ID NO: 74) |
| 38 | NYGGAASFDY (SEQ ID NO: 75) |
| 39 | NYGGTASFDY (SEQ ID NO: 76) |
| 40 | PLGGTASFDY (SEQ ID NO: 77) |
| 41 | QLAGTASFDY (SEQ ID NO: 78) |
| 42 | SFGGTASFDY (SEQ ID NO: 79) |
| 43 | SHGGTASFDY (SEQ ID NO: 80) |
| 44 | SLGGTASFDY (SEQ ID NO: 81) |
| 45 | SMGGTASFDY (SEQ ID NO: 82) |
| 46 | SNGGTASFDY (SEQ ID NO: 83) |
| 47 | SWGGTASFDY (SEQ ID NO: 84) |
| 48 | SYGGTASFDY (SEQ ID NO: 85) |
| 49 | YYGGTASFDY (SEQ ID NO: 86) |

TABLE 8

CDRL3 sequences of mutants selected from the process of improving affinity

| | |
|---|---|
| 1 | QQLYSTPWT (SEQ ID NO: 6) |
| 2 | DQLYGTPWT (SEQ ID NO: 87) |
| 3 | DQMYSTPWT (SEQ ID NO: 88) |
| 4 | HQLAFTPWT (SEQ ID NO: 89) |
| 5 | LQHNEFPWT (SEQ ID NO: 90) |
| 6 | QDMSRTPWT (SEQ ID NO: 91) |
| 7 | QELSTTPWT (SEQ ID NO: 92) |

TABLE 8-continued

CDRL3 sequences of mutants selected from the process of improving affinity

| | |
|---|---|
| 8 | QEMMRTPWT (SEQ ID NO: 93) |
| 9 | QNLAYSPWT (SEQ ID NO: 94) |
| 10 | QNMYGTPWT (SEQ ID NO: 95) |
| 11 | QQAAFSPWT (SEQ ID NO: 96) |
| 12 | QQAAYSPWT (SEQ ID NO: 97) |
| 13 | QQAAYVPWT (SEQ ID NO: 98) |
| 14 | QQCTSDPWT (SEQ ID NO: 99) |
| 15 | QQHDVGPWT (SEQ ID NO: 100) |
| 16 | QQIAFGPWT (SEQ ID NO: 101) |
| 17 | QQIAFNPWT (SEQ ID NO: 102) |
| 18 | QQIAFSPWT (SEQ ID NO: 103) |
| 19 | QQIAFTPWT (SEQ ID NO: 104) |
| 20 | QQIAFVPWT (SEQ ID NO: 105) |
| 21 | QQIAKTPWT (SEQ ID NO: 106) |
| 22 | QQIAYSPWT (SEQ ID NO: 107) |
| 23 | QQIAYTPWT (SEQ ID NO: 108) |
| 24 | QQIAYVPWT (SEQ ID NO: 109) |
| 25 | QQIFSVPWT (SEQ ID NO: 110) |
| 26 | QQIGFSPWT (SEQ ID NO: 111) |
| 27 | QQIGWTPWT (SEQ ID NO: 112) |
| 28 | QQIMTLPWT (SEQ ID NO: 113) |
| 29 | QQIREIPWT (SEQ ID NO: 114) |
| 30 | QQISFMPWT (SEQ ID NO: 115) |
| 31 | QQISFSPWT (SEQ ID NO: 116) |
| 32 | QQIYITPWT (SEQ ID NO: 117) |
| 33 | QQKAYAPWT (SEQ ID NO: 118) |
| 34 | QQKKGIPWT (SEQ ID NO: 119) |
| 35 | QQKMGNPWT (SEQ ID NO: 120) |
| 36 | QQKSVAPWT (SEQ ID NO: 121) |
| 37 | QQLAFAPWT (SEQ ID NO: 122) |
| 38 | QQLAFMPWT (SEQ ID NO: 123) |
| 39 | QQLAFSPWT (SEQ ID NO: 124) |
| 40 | QQLAFVPWT (SEQ ID NO: 125) |
| 41 | QQLAYEPWT (SEQ ID NO: 126) |
| 42 | QQLAYSPWT (SEQ ID NO: 127) |
| 43 | QQLAYTPWT (SEQ ID NO: 128) |
| 44 | QQLAYVPWT (SEQ ID NO: 129) |
| 45 | QQLGFAPWT (SEQ ID NO: 130) |

TABLE 8-continued

CDRL3 sequences of mutants selected from the process of improving affinity

| | | |
|---|---|---|
| 46 | QQLGFIPWT | (SEQ ID NO: 131) |
| 47 | QQLGFSPWT | (SEQ ID NO: 132) |
| 48 | QQLGFVPWT | (SEQ ID NO: 133) |
| 49 | QQLGYAPWT | (SEQ ID NO: 134) |
| 50 | QQLGYSPWT | (SEQ ID NO: 135) |
| 51 | QQLHSTPWT | (SEQ ID NO: 136) |
| 52 | QQLKNTPWT | (SEQ ID NO: 137) |
| 53 | QQLMRKPWT | (SEQ ID NO: 138) |
| 54 | QQLRASPWT | (SEQ ID NO: 139) |
| 55 | QQLRNLPWT | (SEQ ID NO: 140) |
| 56 | QQLRNSPWT | (SEQ ID NO: 141) |
| 57 | QQLRNVPWT | (SEQ ID NO: 142) |
| 58 | QQLRSAPWT | (SEQ ID NO: 143) |
| 59 | QQLRSSPWT | (SEQ ID NO: 144) |
| 60 | QQLRSVPWT | (SEQ ID NO: 145) |
| 61 | QQLRVIPWT | (SEQ ID NO: 146) |
| 62 | QQLSFTPWT | (SEQ ID NO: 147) |
| 63 | QQLSFVPWT | (SEQ ID NO: 148) |
| 64 | QQLSKTPWT | (SEQ ID NO: 149) |
| 65 | QQLSRAPWT | (SEQ ID NO: 150) |
| 66 | QQLSRSPWT | (SEQ ID NO: 151) |
| 67 | QQLSVTPWT | (SEQ ID NO: 152) |
| 68 | QQLSYAPWT | (SEQ ID NO: 153) |
| 69 | QQLSYSPWT | (SEQ ID NO: 154) |
| 70 | QQLVRIPWT | (SEQ ID NO: 155) |
| 71 | QQLVRNPWT | (SEQ ID NO: 156) |
| 72 | QQLVRTPWT | (SEQ ID NO: 157) |
| 73 | QQLVRVPWT | (SEQ ID NO: 158) |
| 74 | OQLYSSPWT | (SEQ ID NO: 159) |
| 75 | QQMAFAPWT | (SEQ ID NO: 160) |
| 76 | QQMAFGPWT | (SEQ ID NO: 161) |
| 77 | QQMAFIPWT | (SEQ ID NO: 162) |
| 78 | QQMAFNPWT | (SEQ ID NO: 163) |
| 79 | QQMAFSPWT | (SEQ ID NO: 164) |
| 80 | QQMAFTPWT | (SEQ ID NO: 165) |
| 81 | QQMAFVPWT | (SEQ ID NO: 166) |
| 82 | QQMAFYPWT | (SEQ ID NO: 167) |
| 83 | QQMAGFPWT | (SEQ ID NO: 168) |
| 84 | QQMASVPWT | (SEQ ID NO: 169) |
| 85 | QQMAYGPWT | (SEQ ID NO: 170) |
| 86 | QQMAYSPWT | (SEQ ID NO: 171) |
| 87 | QQMAYTPWT | (SEQ ID NO: 172) |
| 88 | QQMDFTPWT | (SEQ ID NO: 173) |
| 89 | QQMEHTPWT | (SEQ ID NO: 174) |
| 90 | QQMFAIPWT | (SEQ ID NO: 175) |
| 91 | QQMFGSPWT | (SEQ ID NO: 176) |
| 92 | QQMFRTPWT | (SEQ ID NO: 177) |
| 93 | QQMFSTPWT | (SEQ ID NO: 178) |
| 94 | QQMFSVPWT | (SEQ ID NO: 179) |
| 95 | QQMGFSPWT | (SEQ ID NO: 180) |
| 96 | QQMGYAPWT | (SEQ ID NO: 181) |
| 97 | QQMGYSPWT | (SEQ ID NO: 182) |
| 98 | QQMHIFPWT | (SEQ ID NO: 183) |
| 99 | QQMMAVPWT | (SEQ ID NO: 184) |
| 100 | QQMMKSPWT | (SEQ ID NO: 185) |
| 101 | QQMMRTPWT | (SEQ ID NO: 186) |
| 102 | QQMMRVPWT | (SEQ ID NO: 187) |
| 103 | QQMRKIPWT | (SEQ ID NO: 188) |
| 104 | QQMRNVPWT | (SEQ ID NO: 189) |
| 105 | QQMRRVPWT | (SEQ ID NO: 190) |
| 106 | QQMRSTPWT | (SEQ ID NO: 191) |
| 107 | QQMSFSPWT | (SEQ ID NO: 192) |
| 108 | QOMSHSPWT | (SEQ ID NO: 193) |
| 109 | QQMSKIPWT | (SEQ ID NO: 194) |
| 110 | QQMSRVPWT | (SEQ ID NO: 195) |
| 111 | QQMSYAPWT | (SEQ ID NO: 196) |
| 112 | QQMSYGPWT | (SEQ ID NO: 197) |
| 113 | QQMSYIPWT | (SEQ ID NO: 198) |
| 114 | QQMSYSPWT | (SEQ ID NO: 199) |
| 115 | QQMSYTPWT | (SEQ ID NO: 200) |
| 116 | QQMSYVPWT | (SEQ ID NO: 201) |
| 117 | QQMTRVPWT | (SEQ ID NO: 202) |
| 118 | QQMVIIPWT | (SEQ ID NO: 203) |
| 119 | QQMVREPWT | (SEQ ID NO: 204) |
| 120 | QQMVRSPWT | (SEQ ID NO: 205) |
| 121 | QQMVRTPWT | (SEQ ID NO: 206) |
| 122 | QQMVRVPWT | (SEQ ID NO: 207) |

TABLE 8-continued

CDRL3 sequences of mutants selected from the process of improving affinity

| | |
|---|---|
| 123 | QQMVSIPWT (SEQ ID NO: 208) |
| 124 | QQMYGTPWT (SEQ ID NO: 209) |
| 125 | QQMYKTPWT (SEQ ID NO: 210) |
| 126 | QQMYRTPWT (SEQ ID NO: 211) |
| 127 | QQNAFEPWT (SEQ ID NO: 212) |
| 128 | QQNAFGPWT (SEQ ID NO: 213) |
| 129 | QQNAFIPWT (SEQ ID NO: 214) |
| 130 | QQNAFSPWT (SEQ ID NO: 215) |
| 131 | QQNAFTPWT (SEQ ID NO: 216) |
| 132 | QQNAFVPWT (SEQ ID NO: 217) |
| 133 | QQNAYAPWT (SEQ ID NO: 218) |
| 134 | QQNAYGPWT (SEQ ID NO: 219) |
| 135 | QQNAYNPWT (SEQ ID NO: 220) |
| 136 | QQNAYSPWT (SEQ ID NO: 221) |
| 137 | QQNFIAPWT (SEQ ID NO: 222) |
| 138 | QQNMIVPWT (SEQ ID NO: 223) |
| 139 | QQNRISPWT (SEQ ID NO: 224) |
| 140 | QQNRIWPWT (SEQ ID NO: 225) |
| 141 | QQNRVIPWT (SEQ ID NO: 226) |
| 142 | QQNRVVPWT (SEQ ID NO: 227) |
| 143 | QQNSYSPWT (SEQ ID NO: 228) |
| 144 | QQNVIVPWT (SEQ ID NO: 229) |
| 145 | QQNVNVPWT (SEQ ID NO: 230) |
| 146 | QQNYKLPWT (SEQ ID NO: 231) |
| 147 | QQSAFVPWT (SEQ ID NO: 232) |
| 148 | QQSAYAPWT (SEQ ID NO: 233) |
| 149 | QQSAYIPWT (SEQ ID NO: 234) |
| 150 | QQSEACPWT (SEQ ID NO: 235) |
| 151 | QQSFNTPWT (SEQ ID NO: 236) |
| 152 | QQSKTVPWT (SEQ ID NO: 237) |
| 153 | QQTAFGPWT (SEQ ID NO: 238) |
| 154 | QQTAFSPWT (SEQ ID NO: 239) |
| 155 | QQTAYAPWT (SEQ ID NO: 240) |
| 156 | QQTAYSPWT (SEQ ID NO: 241) |
| 157 | QQTRRTPWT (SEQ ID NO: 242) |
| 158 | QQTSFAPWT (SEQ ID NO: 243) |
| 159 | QQVAYSPWT (SEQ ID NO: 244) |
| 160 | QQVFAIPWT (SEQ ID NO: 245) |

In order to select clones with improved Koff among the selected clones, the clones were analyzed via Biacore 3000 (GE Healthcare). The HER2-ECD-His protein was immobilized to a CM5 sensor chip via an amine coupling method using ECD/NHS. After expressing the antibody from each clone using IPTG, a periplasmic extract was obtained therefrom, and allowed to bind to HER2-ECD-His. The Koff value for each antibody was analyzed via BIAevaluation software. Based on the above, the antibodies with improved Koff value were selected (see: Table 9a). Table 9a disclose the representative examples of the clones showing similar or improved Koff values compared to the hz1E11 parent antibody, among the clones developed by the present inventors.

TABLE 9a

| | hz1E11 | | Mutation-introduced | | Degree of reduction |
|---|---|---|---|---|---|
| Clones | LCDR3 | HCDR3 | chain | koff | (Fold) |
| hz1E11 | QQLYSTPWT (SEQ ID NO: 6) | HLGGTASFDY (SEQ ID NO: 3) | — | 1.13E-03 | 1.0 |
| M3-L-A1-3-1A12 (hz1E11-133) | QQNAYAPWT (SEQ ID NO: 218) | HLGGTASFDY (SEQ ID NO: 3) | L | 3.72E-05 | 30.4 |
| M3-L-A1-3-1F11 (hz1E11-154) | QQTAFSPWT (SEQ ID NO: 239) | HLGGTASFDY (SEQ ID NO: 3) | L | 1.17E-04 | 9.7 |
| M1-L-A1-3-1C3 (hz1E11-3) | DQMYSTPWT (SEQ ID NO: 88) | HLGGTASFDY (SEQ ID NO: 3) | L | 1.52E-04 | 7.4 |
| M3-H-A1-2-1B12 | QQLYSTPWT (SEQ ID NO: 6) | NYGGTASFDY (SEQ ID NO: 76) | H | 2.12E-04 | 5.3 |
| M1-H-A1-2-1B5 | QQLYSTPWT (SEQ ID NO: 6) | HFGGTASFDY (SEQ ID NO: 43) | H | 4.53E-04 | 2.5 |

TABLE 9a-continued

| Clones | hz1E11 LCDR3 | hz1E11 HCDR3 | Mutation-introduced chain | koff | Degree of reduction (Fold) |
|---|---|---|---|---|---|
| M3-H-A1-1-1C11 | QQLYSTPWT (SEQ ID NO: 6) | SWGGTASFDY (SEQ ID NO: 84) | H | 5.67E-04 | 2.0 |
| M3-H-A1-1-1A10 | QQLYSTPWT (SEQ ID NO: 6) | SYGGTASFDY (SEQ ID NO: 85) | H | 1.16E-03 | 1.0 |
| M3-LH-A1-1-1H1 | QQNFIAPWT (SEQ ID NO: 222) | NYGGTASFDY (SEQ ID NO: 76) | LH | 1.66E-03 | 0.7 |
| M3-LH-A3-3-2B1 | QQLVRNPWT (SEQ ID NO: 156) | NFGGTASFDY (SEQ ID NO: 67) | LH | 1.65E-04 | 6.5 |
| M3-L-A3-4-2E8 | QQIAYVPWT (SEQ ID NO: 109) | HLGGTASFDY (SEQ ID NO: 3) | L | 1.80E-04 | 5.9 |
| M1-LH-A3-3-1A6 | QQLVRTPWT (SEQ ID NO: 157) | NYGGTASFDY (SEQ ID NO: 76) | LH | 1.84E-04 | 5.8 |
| M3-H-A3-3-2A7 | QQLSYSTPWT (SEQ ID NO: 154) | NFGGTASFDY (SEQ ID NO: 67) | H | 2.26E-04 | 4.7 |
| M3-LH-A3-3-2F1 | QQNAYNPWT (SEQ ID NO: 220) | HLGGTASFDY (SEQ ID NO: 3) | L | 2.45E-04 | 4.4 |
| M3-LH-A3-3-2A5 | QQMFSTPWT (SEQ ID NO: 178) | HWGGTASFDY (SEQ ID NO: 64) | LH | 2.98E-04 | 3.6 |
| M3-H-A3-3-2D8 | QQLYSTPWT (SEQ ID NO: 6) | HWGGTASFDY (SEQ ID NO: 64) | H | 3.30E-04 | 3.2 |
| M3-LH-A1-2-2F4 | QQLVRIPWT (SEQ ID NO: 155) | NLGGTASFDY (SEQ ID NO: 71) | LH | 3.31E-04 | 3.2 |
| M3-L-A1-3-2C2 | QQLGFIPWT (SEQ ID NO: 131) | HLGGTASFDY (SEQ ID NO: 3) | L | 5.26E-04 | 2.0 |
| M3-H-A3-1-2F3 | QQLYSTPWT (SEQ ID NO: 6) | NLGGTASFDY (SEQ ID NO: 71) | H | 7.70E-04 | 1.4 |
| M3-H-A2-1-1F2 | QQLYSTPWT (SEQ ID NO: 6) | SNGGTASFDY (SEQ ID NO: 83) | H | 1.27E-03 | 0.8 |

As can be seen in Table 9a, various CDRH3s represented by general formula 1 and CDRL3s represented by general formula 2 of the present invention show similar or improved Koff values compared to CDRH3 and CDRL3 of the parent antibody, hz1E11.

Among the randomized CDR3 sequence of the light chain, experiments were performed using hz1E11-3, hz1E11-133 and hz1E11-154.

The heavy chain variable regions of hz1E11-3, hz1E11-133 and hz1E11-154 were the same as that of hz1E11, and the amino acid sequence of the light chain variable regions are described in SEQ ID NOS: 247, 249 and 251, respectively.

In order to confirm the increase in affinities of the selected 3 kinds of antibodies, the antibodies were produced in the form of IgG. The goat anti-human IgG (Invitrogen, #H10500) at a concentration of 2000 RU was immobilized to a CM5 sensor chip via ECD/NHS method. Then, the antibodies were allowed to bind at a rate of 50 μL/min for 5 minutes, and allowed the buffer to flow thereonto for 5 minutes for stabilization purpose. The concentrations of the antibodies used for binding of the antibodies were 0.4 μg/mL for Trastuzumab (TRA), 0.8 μg/mL for pertuzumab (PER), and 1 μg/mL for hz1E11 and the selected antibodies. After stabilizing the antibodies, the HER2-ECD-His protein at concentrations of 640 nM, 320 nM, 160 nM, 80 nM, 40 nM, 20 nM, and 0 nM was allowed to bind at a rate of 50 μL/min for 4 minutes, and allowed the buffer to flow thereonto for 15 minutes to separate. After analyzing each of the concentrations, they were recycled using 10 mM Glycine (pH 1.5) and performed the subsequent assays. The affinities of the antibodies were analyzed via BIAevaluation software. The results of analysis are summarized in Table 9b.

TABLE 9b

| Antibodies | Ka (1/Ms) | kd (1/s) | Rmax | KD (M) |
|---|---|---|---|---|
| hz1E11 | 3.60E+04 | 8.30E-04 | 61 | 2.30E-08 |
| hz1E11-3 | 3.80E+04 | 2.00E-04 | 64 | 5.20E-09 |
| hz1E11-133 | 6.40E+04 | 9.90E-05 | 68 | 1.50E-09 |
| hz1E11-154 | 8.60E+04 | 9.90E-05 | 65 | 1.10E-09 |
| TRA | 4.90E+04 | 1.50E-04 | 43 | 3.00E-09 |
| PER | 3.80E+04 | 1.20E-04 | 56 | 3.30E-09 |

In Table 9b above, ka, kd Rmax and KD respectively indicate association rate constant, dissociation rate constant, maximum binding capacity, and equilibrium dissociation constant.

As can be seen in Table 9b, hz1E11-133 and hz1E11-154 showed an 8.4-fold decrease in Koff value, i.e., kd values, compared to that of hz1E11, whereas they showed a bit increase in kon value, i.e., ka value. Conclusively, with respect to final affinity, hz1E11-133 showed 1.5 nM and hz1E11-154 showed 1.1 nM, which were a 15-fold improvement and a 20-fold improvement compared to that of hz1E11.

Example 15: Confirmation of Anticancer Effects of Antibodies with Improved Affinities The anticancer effects of the antibodies with improved affinities were confirmed regarding HER2-overexpressing stomach cancer and breast cancer. Cancer cell survival rates when NCI-N87 and OE-19, HER2-overexpressing stomach cancer cell lines, BT-474, a HER2-overexpressing breast cancer cell line treated with single treatment by each antibody alone or a combined treatment along with of trastuzumab, according to concentration, were analyzed As can be seen in FIGS. 11A to 11F, the hz1E11-3, hz1E11-133, and hz1E11-154 antibodies with improved affinities showed improved effects in single treatment and combined treatment compared to that of hz1E11.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. An antibody to human epidermal growth factor receptor 2 (HER2) or antigen-binding fragment thereof, comprising:
   (i) a heavy chain variable region comprising a complementarity determining region (CDR) H1 of SEQ ID NO:1, CDRH2 of SEQ ID NO:2 and CDRH3 of SEQ ID NO:3 and a light chain variable region comprising CDRL1 of SEQ ID NO:4, CDRL2 of SEQ ID NO:5 and CDRL3 of SEQ ID NO:6;
   (ii) a heavy chain variable region comprising CDRH1 of SEQ ID NO:1, CDRH2 of SEQ ID NO:2 and CDRH3 of SEQ ID NO:3 and a light chain variable region comprising CDRL1 of SEQ ID NO:4, CDRL2 of SEQ ID NO:5 and CDRL3 of SEQ ID NO:218;
   (iii) a heavy chain variable region comprising CDRH1 of SEQ ID NO:1, CDRH2 of SEQ ID NO:2 and CDRH3 of SEQ ID NO:3 and a light chain variable region comprising CDRL1 of SEQ ID NO:4, CDRL2 of SEQ ID NO:5 and CDRL3 of SEQ ID NO:239;
   (iv) a heavy chain variable region comprising CDRH1 of SEQ ID NO:1, CDRH2 of SEQ ID NO:2 and CDRH3 of SEQ ID NO:3 and a light chain variable region comprising CDRL1 of SEQ ID NO:4, CDRL2 of SEQ ID NO:5 and CDRL3 of SEQ ID NO:88;
   (v) a heavy chain variable region comprising CDR H1 of SEQ ID NO:1, CDRH2 of SEQ ID NO:2 and CDRH3 of SEQ ID NO:76 and a light chain variable region comprising CDRL1 of SEQ ID NO:4, CDRL2 of SEQ ID NO:5 and CDRL3 of SEQ ID NO:6;
   (vi) a heavy chain variable region comprising CDR H1 of SEQ ID NO:1, CDRH2 of SEQ ID NO:2 and CDRH3 of SEQ ID NO:43 and a light chain variable region comprising CDRL1 of SEQ ID NO:4, CDRL2 of SEQ ID NO:5 and CDRL3 of SEQ ID NO:6;

(vii) a heavy chain variable region comprising CDR H1 of SEQ ID NO:1, CDRH2 of SEQ ID NO:2 and CDRH3 of SEQ ID NO:84 and a light chain variable region comprising CDRL1 of SEQ ID NO:4, CDRL2 of SEQ ID NO:5 and CDRL3 of SEQ ID NO:6;

(viii) a heavy chain variable region comprising CDR H1 of SEQ ID NO:1, CDRH2 of SEQ ID NO:2 and CDRH3 of SEQ ID NO:85 and a light chain variable region comprising CDRL1 of SEQ ID NO:4, CDRL2 of SEQ ID NO:5 and CDRL3 of SEQ ID NO:6;

(ix) a heavy chain variable region comprising CDRH1 of SEQ ID NO:1, CDRH2 of SEQ ID NO:2 and CDRH3 of SEQ ID NO:76 and a light chain variable region comprising CDRL1 of SEQ ID NO:4, CDRL2 of SEQ ID NO:5 and CDRL3 of SEQ ID NO:222;

(x) a heavy chain variable region comprising CDR H1 of SEQ ID NO:1, CDRH2 of SEQ ID NO:2 and CDRH3 of SEQ ID NO:67 and a light chain variable region comprising CDRL1 of SEQ ID NO:4, CDRL2 of SEQ ID NO:5 and CDRL3 of SEQ ID NO:156;

(xi) a heavy chain variable region comprising CDR H1 of SEQ ID NO:1, CDRH2 of SEQ ID NO:2 and CDRH3 of SEQ ID NO:3 and a light chain variable region comprising CDRL1 of SEQ ID NO:4, CDRL2 of SEQ ID NO:5 and CDRL3 of SEQ ID NO:109;

(xii) a heavy chain variable region comprising CDR H1 of SEQ ID NO:1, CDRH2 of SEQ ID NO:2 and CDRH3 of SEQ ID NO:76 and a light chain variable region comprising CDRL1 of SEQ ID NO:4, CDRL2 of SEQ ID NO:5 and CDRL3 of SEQ ID NO:157;

(xiii) a heavy chain variable region comprising CDR H1 of SEQ ID NO:1, CDRH2 of SEQ ID NO:2 and CDRH3 of SEQ ID NO:67 and a light chain variable region comprising CDRL1 of SEQ ID NO:4, CDRL2 of SEQ ID NO:5 and CDRL3 of SEQ ID NO:154;

(xiv) a heavy chain variable region comprising CDR H1 of SEQ ID NO:1, CDRH2 of SEQ ID NO:2 and CDRH3 of SEQ ID NO:3 and a light chain variable region comprising CDRL1 of SEQ ID NO:4, CDRL2 of SEQ ID NO:5 and CDRL3 of SEQ ID NO:220;

(xv) a heavy chain variable region comprising CDR H1 of SEQ ID NO:1, CDRH2 of SEQ ID NO:2 and CDRH3 of SEQ ID NO:64 and a light chain variable region comprising CDRL1 of SEQ ID NO:4, CDRL2 of SEQ ID NO:5 and CDRL3 of SEQ ID NO:178;

(xvi) a heavy chain variable region comprising CDR H1 of SEQ ID NO:1, CDRH2 of SEQ ID NO:2 and CDRH3 of SEQ ID NO:64 and a light chain variable region comprising CDRL1 of SEQ ID NO:4, CDRL2 of SEQ ID NO:5 and CDRL3 of SEQ ID NO:6;

(xvii) a heavy chain variable region comprising CDR H1 of SEQ ID NO:1, CDRH2 of SEQ ID NO:2 and CDRH3 of SEQ ID NO:71 and a light chain variable region comprising CDRL1 of SEQ ID NO:4, CDRL2 of SEQ ID NO:5 and CDRL3 of SEQ ID NO:155;

(xviii) a heavy chain variable region comprising CDR H1 of SEQ ID NO:1, CDRH2 of SEQ ID NO:2 and CDRH3 of SEQ ID NO:3 and a light chain variable region comprising CDRL1 of SEQ ID NO:4, CDRL2 of SEQ ID NO:5 and CDRL3 of SEQ ID NO:131;

(xix) a heavy chain variable region comprising CDR H1 of SEQ ID NO:1, CDRH2 of SEQ ID NO:2 and CDRH3 of SEQ ID NO:71 and a light chain variable region comprising CDRL1 of SEQ ID NO:4, CDRL2 of SEQ ID NO:5 and CDRL3 of SEQ ID NO:6 or (xx) a heavy chain variable region comprising CDR H1 of SEQ ID NO:1, CDRH2 of SEQ ID NO:2 and CDRH3 of SEQ ID NO:83 and a light chain variable region comprising CDRL1 of SEQ ID NO:4, CDRL2 of SEQ ID NO:5 and CDRL3 of SEQ ID NO:6.

2. The antibody or antigen-binding fragment thereof according to claim 1, wherein the heavy chain variable region of (i), (ii), (iii), (iv), (xi), (xiv) and (xviii) comprises the amino acid sequence of SEQ ID NOs: 8 or 24.

3. The antibody or antigen-binding fragment thereof according to claim 1, wherein the light chain variable region of (i), (v), (vi), (vii), (viii), (xvi), (xix), and (xx) comprises the amino acid sequence of SEQ ID NOs: 10 or 26.

4. A pharmaceutical composition comprising: (a) a pharmaceutically effective amount of the antibody to HER2 or antigen-binding fragment thereof according to claim 1; and (b) a pharmaceutically acceptable carrier.

5. The pharmaceutical composition according to claim 4, wherein the composition further comprises trastuzumab.

6. A pharmaceutical composition for inducing apoptosis, comprising: (a) a pharmaceutically effective amount of the antibody to HER2 or antigen-binding fragment thereof according to claim 1; and (b) a pharmaceutically acceptable carrier.

7. The pharmaceutical composition according to claim 6, wherein the pharmaceutical composition induces apoptosis for treatment of a hyperproliferative disease that expresses HER2; and wherein the hyperproliferative disease is cancer, hyperplasia, keloid, Cushing syndrome, primary aldosteronism, erythroplakia, polycythemia vera, leukoplakia, hyperplastic scar, lichen planus, lentiginosis, arteriosclerosis, atherosclerosis, restenosis, or stenosis.

8. A kit for detecting HER2 in a biological sample comprising the antibody to HER2 or antigen-binding fragment thereof according to claim 1.

9. A pharmaceutical composition comprising: (a) a pharmaceutically effective amount of the antibody to HER2 or antigen-binding fragment thereof according to claim 2; and (b) a pharmaceutically acceptable carrier.

10. A pharmaceutical composition comprising: (a) a pharmaceutically effective amount of the antibody to HER2 or antigen-binding fragment thereof according to claim 3; and (b) a pharmaceutically acceptable carrier.

11. The pharmaceutical composition according to claim 9, wherein the composition further comprises trastuzumab.

12. The pharmaceutical composition according to claim 10, wherein the composition further comprises trastuzumab.

13. A pharmaceutical composition for inducing apoptosis, comprising: (a) a pharmaceutically effective amount of the antibody to HER2 or antigen-binding fragment thereof according to claim 2; and (b) a pharmaceutically acceptable carrier.

14. The pharmaceutical composition according to claim 13, wherein the pharmaceutical composition induces apoptosis for treatment of a hyperproliferative disease that expresses HER2; wherein the hyperproliferative disease is cancer, hyperplasia, keloid, Cushing syndrome, primary aldosteronism, erythroplakia, polycythemia vera, leukoplakia, hyperplastic scar, lichen planus, lentiginosis, arteriosclerosis, atherosclerosis, restenosis or stenosis.

15. A pharmaceutical composition for inducing apoptosis, comprising: (a) a pharmaceutically effective amount of the antibody to HER2 or antigen-binding fragment thereof according to claim 3; and (b) a pharmaceutically acceptable carrier.

16. The pharmaceutical composition according to claim 15, wherein the pharmaceutical composition induces apoptosis for treatment of a hyperproliferative disease that express HER2; and wherein the hyperproliferative disease is cancer, hyperplasia, keloid, Cushing syndrome, primary aldosteronism, erythroplakia, polycythemia vera, leukoplakia, hyperplastic scar, lichen planus, lentiginosis, arteriosclerosis, atherosclerosis, restenosis or stenosis.

17. A kit for detecting HER2 in a biological sample comprising the antibody to HER2 or antigen-binding fragment thereof according to claim 2.

18. A kit for detecting HER2 in a biological comprising the antibody to HER2 or antigen-binding fragment thereof according to claim 3.

19. A method for treating a cancer and/or inducing apoptosis for treatment of a hyperproliferative disease of a subject, comprising administering to the subject in need thereof a composition comprising (a) a pharmaceutically effective amount of the antibody to HER2 or antigen-binding fragment thereof according to claim 1; and (b) a pharmaceutically acceptable carrier,
wherein the cancer and the hyperproliferative disease express HER2.

20. The method according to claim 19, which further comprises administering trastuzumab.

21. The method according to claim 19, wherein the cancer that expresses HER2 is breast cancer, ovarian cancer, stomach cancer, lung cancer, liver cancer, bronchus cancer, nasopharyngeal cancer, laryngeal cancer, pancreatic cancer, bladder cancer, colorectal cancer, colon cancer, cervical cancer, brain cancer, prostate cancer, bone cancer, head and neck cancer, skin cancer, thyroid cancer, parathyroid cancer, or ureteral cancer.

22. The method according to claim 19, wherein the hyperproliferative disease that expresses HER2 is cancer, hyperplasia, keloid, Cushing syndrome, primary aldosteronism, erythroplakia, polycythemia vera, leukoplakia, hyperplastic scar, lichen planus, lentiginosis, arteriosclerosis, atherosclerosis, restenosis or stenosis.

23. A method for treating a cancer and/or inducing apoptosis for treatment of a hyperproliferative disease of a subject, comprising administering to the subject in need thereof a composition comprising (a) a pharmaceutically effective amount of the antibody to HER2 or antigen-binding fragment thereof according to claim 2; and (b) a pharmaceutically acceptable carrier,
wherein the cancer and the hyperproliferative disease express HER2.

24. The method according to claim 23, which further comprises administering trastuzumab.

25. The method according to claim 23, wherein the cancer that expresses HER2 is breast cancer, ovarian cancer, stomach cancer, lung cancer, liver cancer, bronchus cancer, nasopharyngeal cancer, laryngeal cancer, pancreatic cancer, bladder cancer, colorectal cancer, colon cancer, cervical cancer, brain cancer, prostate cancer, bone cancer, head and neck cancer, skin cancer, thyroid cancer, parathyroid cancer, or ureteral cancer.

26. The method according to claim 23, wherein the hyperproliferative disease that expresses HER2 is cancer, hyperplasia, keloid, Cushing syndrome, primary aldosteronism, erythroplakia, polycythemia vera, leukoplakia, hyperplastic scar, lichen planus, lentiginosis, arteriosclerosis, atherosclerosis, restenosis or stenosis.

27. A method for treating a cancer and/or inducing apoptosis for treatment of a hyperproliferative disease of a subject, comprising administering to the subject in need thereof a composition comprising (a) a pharmaceutically effective amount of the antibody to HER2 or antigen-binding fragment thereof according to claim 3; and (b) a pharmaceutically acceptable carrier,
wherein the cancer and the hyperproliferative disease express HER2.

28. The method according to claim 27, which further comprises administering trastuzumab.

29. The method according to claim 27, wherein the cancer that expresses HER2 is breast cancer, ovarian cancer, stomach cancer, lung cancer, liver cancer, bronchus cancer, nasopharyngeal cancer, laryngeal cancer, pancreatic cancer, bladder cancer, colorectal cancer, colon cancer, cervical cancer, brain cancer, prostate cancer, bone cancer, head and neck cancer, skin cancer, thyroid cancer, parathyroid cancer, or ureteral cancer.

30. The method according to claim 27, wherein the hyperproliferative disease that expresses HER2 is cancer, hyperplasia, keloid, Cushing syndrome, primary aldosteronism, erythroplakia, polycythemia vera, leukoplakia, hyperplastic scar, lichen planus, lentiginosis, arteriosclerosis, atherosclerosis, restenosis or stenosis.

31. The antibody or antigen-binding fragment thereof according to claim 1, wherein the heavy chain variable region of (i) comprises the amino acid sequence of SEQ ID NOs: 8 or 24.

32. The antibody or antigen-binding fragment thereof according to claim 1, wherein the light chain variable region of (i), (iv), (ii), and (iii) comprises the amino acid sequence of SEQ ID NOs: 26, 247, 249, and 251, respectively.

* * * * *

```
                       SEQUENCE LISTING

<160> NUMBER OF SEQ ID NOS: 253

<210> SEQ ID NO 1
<211> LENGTH: 5
<212> TYPE: PRT
<213> ORGANISM: Artificial Sequence
<220> FEATURE:
<223> OTHER INFORMATION: CDRH1 of 1E11 antibody

<400> SEQUENCE: 1

Ser Tyr Thr Met Ser
 1               5

<210> SEQ ID NO 2
<211> LENGTH: 17
<212> TYPE: PRT
<213> ORGANISM: Artificial Sequence
<220> FEATURE:
<223> OTHER INFORMATION: CDRH2 of 1E11 antibody

<400> SEQUENCE: 2

Tyr Ile Ser Asn Gly Gly Gly Ser Thr Tyr Tyr Pro Asp Thr Val Lys
 1               5                  10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: CDRH3 of 1E11 antibody

<400> SEQUENCE: 3

His Leu Gly Gly Thr Ala Ser Phe Asp Tyr
 1               5                  10

<210> SEQ ID NO 4
<211> LENGTH: 11
<212> TYPE: PRT
<213> ORGANISM: Artificial Sequence
<220> FEATURE:
<223> OTHER INFORMATION: CDRL1 of 1E11 antibody

<400> SEQUENCE: 4

Leu Ala Ser Gln Thr Ile Gly Thr Trp Leu Ala
 1               5                  10

<210> SEQ ID NO 5
<211> LENGTH: 6
<212> TYPE: PRT
<213> ORGANISM: Artificial Sequence
```

```
<220> FEATURE:
<223> OTHER INFORMATION: CDRL2 of 1E11 antibody

<400> SEQUENCE: 5

Ala Thr Ser Leu Ala Asp
  1               5

<210> SEQ ID NO 6
<211> LENGTH: 9
<212> TYPE: PRT
<213> ORGANISM: Artificial Sequence
<220> FEATURE:
<223> OTHER INFORMATION: CDRL3 of 1E11 antibody

<400> SEQUENCE: 6

Gln Gln Leu Tyr Ser Thr Pro Trp Thr
  1               5

<210> SEQ ID NO 7
<211> LENGTH: 357
<212> TYPE: DNA
<213> ORGANISM: Artificial Sequence
<220> FEATURE:
<223> OTHER INFORMATION: Nucleotide sequence of 1E11 heavy chain
      variable region

<400> SEQUENCE: 7
gaggtgaagt tggtggagtc tgggggaggt ttagtgcagc ctggagggtc cctgaaactc      60
tcctgtgcag cctctggatt cactttcagt agctatacca tgtcttgggt tcgccagact     120
ccagagaaga ggctggagtg ggtcgcatac attagtaatg gtggtggtag cacttactat     180
ccagacactg taaagggccg attcaccatc tccagagaca atgccaagaa caccctgtac     240
ctgcaaatga gcagtctgaa gtctgaggac acggccatgt attactgtgc aagacatcta     300
ggtgggactg cctcttttga ctactggggc caaggcacca cggtcaccgt ctcctca       357

<210> SEQ ID NO 8
<211> LENGTH: 119
<212> TYPE: PRT
<213> ORGANISM: Artificial Sequence
<220> FEATURE:
<223> OTHER INFORMATION: Amino acid sequence of 1E11 heavy chain
      variable region

<400> SEQUENCE: 8

Glu Val Lys Leu Val Glu Ser Gly Gly Gly Leu Val Gln Pro Gly Gly
  1               5                  10                  15

Ser Leu Lys Leu Ser Cys Ala Ala Ser Gly Phe Thr Phe Ser Ser Tyr
             20                  25                  30

Thr Met Ser Trp Val Arg Gln Thr Pro Glu Lys Arg Leu Glu Trp Val
         35                  40                  45

Ala Tyr Ile Ser Asn Gly Gly Gly Ser Thr Tyr Tyr Pro Asp Thr Val
     50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Arg His Leu Gly Gly Thr Ala Ser Phe Asp Tyr Trp Gly Gln Gly
            100                 105                 110

Thr Thr Val Thr Val Ser Ser
        115
```

<210> SEQ ID NO 9
<211> LENGTH: 321
<212> TYPE: DNA
<213> ORGANISM: Artificial Sequence
<220> FEATURE:
<223> OTHER INFORMATION: Nucleotide sequence of 1E11 light chain
      variable region

<400> SEQUENCE: 9

```
gacattcaga tgactcagtc tcctgcctcc cagtctgcat ctctgggaga aagtgtcacc    60
atcacatgcc tggcaagtca gaccattggt acatggttag catggtatca gcagaaacca   120
gggaaatctc ctcagctcct gatttatgtt gcaaccagcc tggcagatgg ggtcccatca   180
aggttcagtg gtagtggatc tggcacaaaa ttttctttca agatcagcag cctacaggct   240
gaagattttg taagttatta ctgtcaacaa ctttacagta ctccgtggac gttcggtgga   300
gggaccaagc tggagctgaa a                                             321
```

<210> SEQ ID NO 10
<211> LENGTH: 107
<212> TYPE: PRT
<213> ORGANISM: Artificial Sequence
<220> FEATURE:
<223> OTHER INFORMATION: Amino acid sequence of 1E11 light chain
      variable region

<400> SEQUENCE: 10

Asp Ile Gln Met Thr Gln Ser Pro Ala Ser Gln Ser Ala Ser Leu Gly
 1               5                  10                  15

Glu Ser Val Thr Ile Thr Cys Leu Ala Ser Gln Thr Ile Gly Thr Trp
            20                  25                  30

Leu Ala Trp Tyr Gln Gln Lys Pro Gly Lys Ser Pro Gln Leu Leu Ile
        35                  40                  45

Tyr Val Ala Thr Ser Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Glu Asp Phe Val Ser Tyr Tyr Cys Gln Gln Leu Tyr Ser Thr Pro Trp
                85                  90                  95

Thr Phe Gly Gly Gly Thr Lys Leu Glu Leu Lys
            100                 105

<210> SEQ ID NO 11
<211> LENGTH: 324
<212> TYPE: DNA
<213> ORGANISM: Artificial Sequence
<220> FEATURE:
<223> OTHER INFORMATION: Constant region of human IgG kappa chain

<400> SEQUENCE: 11

```
cgtacggtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagttcgcc cgtcacaaag   300
agcttcaaca ggggagagtg ttaa                                          324
```

<210> SEQ ID NO 12

<211> LENGTH: 107
<212> TYPE: PRT
<213> ORGANISM: Artificial Sequence
<220> FEATURE:
<223> OTHER INFORMATION: Constant region of human IgG kappa chain

<400> SEQUENCE: 12

```
Arg Thr Val Ala Ala Pro Ser Val Phe Ile Phe Pro Pro Ser Asp Glu
  1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 13
<211> LENGTH: 990
<212> TYPE: DNA
<213> ORGANISM: Artificial Sequence
<220> FEATURE:
<223> OTHER INFORMATION: Constant region of human IgG heavy chain

<400> SEQUENCE: 13

```
gctagcacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagaa agttgagccc   300
aaatcttgcg acaaaactca cacatgccca ccgtgcccag cacctgaact cctggggggga   360
ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacaac   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag gcagccccg agaaccacag gtgtacaccc tgcccccatc ccgggatgag   720
ctgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctac agcaagctca ccgtggacaa gagcaggtgg   900
cagcagggga acgtcttctc atgctccgtg atgcatgagg ctctgcacaa ccactacacg   960
cagaagagcc tctccctgtc cccgggtaaa                                    990
```

<210> SEQ ID NO 14
<211> LENGTH: 330
<212> TYPE: PRT
<213> ORGANISM: Artificial Sequence
<220> FEATURE:

<223> OTHER INFORMATION: Constant region of human IgG heavy chain

<400> SEQUENCE: 14

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 15
<211> LENGTH: 81
<212> TYPE: DNA
<213> ORGANISM: Artificial Sequence
<220> FEATURE:
<223> OTHER INFORMATION: Synthetic construct LF-1

<400> SEQUENCE: 15
ccgatcgata tggagacaga cacactcctg ctatgggtac tgctgctctg ggttccaggt    60
tccacgtggg atattcagat g                                         81

<210> SEQ ID NO 16
<211> LENGTH: 26
<212> TYPE: DNA
<213> ORGANISM: Artificial Sequence
<220> FEATURE:
<223> OTHER INFORMATION: Synthetic construct LR-1

<400> SEQUENCE: 16
cggcgtacgt ttcagctcca gcttgg                                    26

<210> SEQ ID NO 17
<211> LENGTH: 80
<212> TYPE: DNA
<213> ORGANISM: Artificial Sequence
<220> FEATURE:
<223> OTHER INFORMATION: Synthetic construct HF-1

<400> SEQUENCE: 17
ccgatcgata tggagacaga cacactcctg ctatgggtac tgctgctctg ggttccaggt    60
tccacgtggg aggtgaagct                                           80

<210> SEQ ID NO 18
<211> LENGTH: 24
<212> TYPE: DNA
<213> ORGANISM: Artificial Sequence
<220> FEATURE:
<223> OTHER INFORMATION: Synthetic construct HR-1

<400> SEQUENCE: 18
cgggctagct gaggagacgg tgac                                      24

<210> SEQ ID NO 19
<211> LENGTH: 27
<212> TYPE: DNA
<213> ORGANISM: Artificial Sequence
<220> FEATURE:
<223> OTHER INFORMATION: Synthetic construct Ck-F

<400> SEQUENCE: 19
ggagctgaaa cgtacggtgg ctgcacc                                   27

<210> SEQ ID NO 20
<211> LENGTH: 28
<212> TYPE: DNA
<213> ORGANISM: Artificial Sequence
<220> FEATURE:
<223> OTHER INFORMATION: Synthetic construct Ck-R

<400> SEQUENCE: 20
ccgctcgagt taacactctc ccctgttg                                  28

<210> SEQ ID NO 21
<211> LENGTH: 34
<212> TYPE: DNA
<213> ORGANISM: Artificial Sequence
<220> FEATURE:
<223> OTHER INFORMATION: Synthetic construct CH-F

<400> SEQUENCE: 21
caccgtctcc tcagctagca ccaagggccc atcg                           34

<210> SEQ ID NO 22
<211> LENGTH: 31

```
<212> TYPE: DNA
<213> ORGANISM: Artificial Sequence
<220> FEATURE:
<223> OTHER INFORMATION: Synthetic construct CH-R

<400> SEQUENCE: 22
ccgctcgagt catttacccg gggacaggga g                                    31

<210> SEQ ID NO 23
<211> LENGTH: 357
<212> TYPE: DNA
<213> ORGANISM: Artificial Sequence
<220> FEATURE:
<223> OTHER INFORMATION: Nucleotide sequence of hz1E11 heavy chain
      variable region

<400> SEQUENCE: 23
gaagtgcagc tagtggagtc aggcggcggt ttagtgcagc cgggggctc cctcaggctg       60 tcttgcgccg caagtggatt taccttcagc agctatacaa tgtcttgggt cagacaagcg    120
cctggaaagg gactggagtg gtagcctac atctccaacg ggggcggaag tacgtattat     180
ccagatactg ttaaagggag atttacaatt agcagagaca atgccaagaa ttccttgtat    240
ctgcagatga actctctcag agctgaagat accgcagtct actattgtgc tagacacctg    300
ggtgggaccg cctccttcga ctactggggc cagggtacac ttgttactgt gtcatct        357

<210> SEQ ID NO 24
<211> LENGTH: 119
<212> TYPE: PRT
<213> ORGANISM: Artificial Sequence
<220> FEATURE:
<223> OTHER INFORMATION: Amino acid sequence of hz1E11 heavy chain
      variable region

<400> SEQUENCE: 24

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Tyr Ile Ser Asn Gly Gly Gly Ser Thr Tyr Tyr Pro Asp Thr Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg His Leu Gly Gly Thr Ala Ser Phe Asp Tyr Trp Gly Gln Gly
            100                 105                 110

Thr Leu Val Thr Val Ser Ser
        115

<210> SEQ ID NO 25
<211> LENGTH: 321
<212> TYPE: DNA
<213> ORGANISM: Artificial Sequence
<220> FEATURE:
<223> OTHER INFORMATION: Nucleotide sequence of hz1E11 light chain
      variable region

<400> SEQUENCE: 25
gatatccaga tgacacaaag cccatcatct ttatctgcca gcgtgggaga tagagtgacc     60
```

```
atcacatgtc tggcatcaca gaccatcgga acttggttgg cctggtacca gcaaaaacca    120
ggcaaggccc ctaagctgct gatttacgtc gcaacgagtc tcgctgacgg tgtgccttcc    180
agattttccg gttccggcag cggcacagac tttactctga caattagttc cctgcagccc    240
gaggacttcg ctacttatta ctgccagcag ctttatagca cccccctggac cttcgggcag    300 gggaccaaag ttgaaataaa g                                               321
```

<210> SEQ ID NO 26
<211> LENGTH: 107
<212> TYPE: PRT
<213> ORGANISM: Artificial Sequence
<220> FEATURE:
<223> OTHER INFORMATION: Amino acid sequence of hz1E11 light chain
      variable region

<400> SEQUENCE: 26

```
Asp Ile Gln Met Thr Gln Ser Pro Ser Ser Leu Ser Ala Ser Val Gly
 1               5                  10                  15

Asp Arg Val Thr Ile Thr Cys Leu Ala Ser Gln Thr Ile Gly Thr Trp
            20                  25                  30

Leu Ala Trp Tyr Gln Gln Lys Pro Gly Lys Ala Pro Lys Leu Leu Ile
        35                  40                  45

Tyr Val Ala Thr Ser Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Tyr Ser Thr Pro Trp
                85                  90                  95

Thr Phe Gly Gln Gly Thr Lys Val Glu Ile Lys
            100                 105
```

<210> SEQ ID NO 27
<211> LENGTH: 10
<212> TYPE: PRT
<213> ORGANISM: Artificial Sequence
<220> FEATURE:
<223> OTHER INFORMATION: Alanine substituted sequence of CDRH3 of hz1E11

<400> SEQUENCE: 27

```
Ala Leu Gly Gly Thr Ala Ser Phe Asp Tyr
 1               5                  10
```

<210> SEQ ID NO 28
<211> LENGTH: 10
<212> TYPE: PRT
<213> ORGANISM: Artificial Sequence
<220> FEATURE:
<223> OTHER INFORMATION: Alanine substituted sequence of CDRH3 of hz1E11

<400> SEQUENCE: 28

```
His Ala Gly Gly Thr Ala Ser Phe Asp Tyr
 1               5                  10
```

<210> SEQ ID NO 29
<211> LENGTH: 10
<212> TYPE: PRT
<213> ORGANISM: Artificial Sequence
<220> FEATURE:
<223> OTHER INFORMATION: Alanine substituted sequence of CDRH3 of hz1E11

<400> SEQUENCE: 29

His Leu Ala Gly Thr Ala Ser Phe Asp Tyr
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Alanine substituted sequence of CDRH3 of hz1E11

<400> SEQUENCE: 30

His Leu Gly Ala Thr Ala Ser Phe Asp Tyr
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Alanine substituted sequence of CDRH3 of hz1E11

<400> SEQUENCE: 31

His Leu Gly Gly Ala Ala Ser Phe Asp Tyr
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Alanine substituted sequence of CDRH3 of hz1E11

<400> SEQUENCE: 32

His Leu Gly Gly Thr Ala Ala Phe Asp Tyr
1               5                   10

<210> SEQ ID NO 33
<211> LENGTH: 9
<212> TYPE: PRT
<213> ORGANISM: Artificial Sequence
<220> FEATURE:
<223> OTHER INFORMATION: Alanine substituted sequence of CDRL3 of hz1E11

<400> SEQUENCE: 33

Ala Gln Leu Tyr Ser Thr Pro Trp Thr
1               5

<210> SEQ ID NO 34
<211> LENGTH: 9
<212> TYPE: PRT
<213> ORGANISM: Artificial Sequence
<220> FEATURE:
<223> OTHER INFORMATION: Alanine substituted sequence of CDRL3 of hz1E11

<400> SEQUENCE: 34

Gln Ala Leu Tyr Ser Thr Pro Trp Thr
1               5

<210> SEQ ID NO 35
<211> LENGTH: 9
<212> TYPE: PRT
<213> ORGANISM: Artificial Sequence
<220> FEATURE:
<223> OTHER INFORMATION: Alanine substituted sequence of CDRL3 of hz1E11

<400> SEQUENCE: 35

Gln Gln Ala Tyr Ser Thr Pro Trp Thr

<210> SEQ ID NO 36
<211> LENGTH: 9
<212> TYPE: PRT
<213> ORGANISM: Artificial Sequence
<220> FEATURE:
<223> OTHER INFORMATION: Alanine substituted sequence of CDRL3 of hz1E11

<400> SEQUENCE: 36

Gln Gln Leu Ala Ser Thr Pro Trp Thr
1               5

<210> SEQ ID NO 37
<211> LENGTH: 9
<212> TYPE: PRT
<213> ORGANISM: Artificial Sequence
<220> FEATURE:
<223> OTHER INFORMATION: Alanine substituted sequence of CDRL3 of hz1E11

<400> SEQUENCE: 37

Gln Gln Leu Tyr Ala Thr Pro Trp Thr
1               5

<210> SEQ ID NO 38
<211> LENGTH: 9
<212> TYPE: PRT
<213> ORGANISM: Artificial Sequence
<220> FEATURE:
<223> OTHER INFORMATION: Alanine substituted sequence of CDRL3 of hz1E11

<400> SEQUENCE: 38

Gln Gln Leu Tyr Ser Ala Pro Trp Thr
1               5

<210> SEQ ID NO 39
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 39

Ala Phe Gly Gly Thr Ala Ser Phe Asp Tyr
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 40

Asp Leu Gly Gly Thr Ala Ser Phe Asp Tyr
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 41

Phe Trp Gly Gly Thr Ala Ser Phe Asp Tyr
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 42

His Cys Gly Gly Thr Ala Ser Phe Asp Tyr
 1               5                  10

<210> SEQ ID NO 43
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 43

His Phe Gly Gly Thr Ala Ser Phe Asp Tyr
 1               5                  10

<210> SEQ ID NO 44
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 44

His His Gly Gly Thr Ala Ser Phe Asp Tyr
 1               5                  10

<210> SEQ ID NO 45
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 45

His Ile Gly Gly Thr Ala Ser Phe Asp Tyr
 1               5                  10

<210> SEQ ID NO 46
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 46

His Leu Cys Ser Thr Ala Ser Phe Asp Tyr
 1               5                  10

<210> SEQ ID NO 47
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 47

His Leu Cys Val Thr Ala Ser Phe Asp Tyr
 1               5                  10

<210> SEQ ID NO 48
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 48

His Leu Gly Gly Ala Ala Ser Phe Asp Tyr
 1               5                  10

<210> SEQ ID NO 49
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 49

His Leu Gly Gly Leu Pro Ser Phe Asp Tyr
 1               5                  10

<210> SEQ ID NO 50
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 50

His Leu Gly Gly Met Ala Ser Phe Asp Tyr
 1               5                  10

<210> SEQ ID NO 51
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 51

His Leu Gly Gly Met Ser Ser Phe Asp Tyr
 1               5                  10

<210> SEQ ID NO 52
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 52

His Leu Gly Gly Met Thr Ser Phe Asp Tyr
 1               5                  10

<210> SEQ ID NO 53
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 53

His Leu Gly Gly Ser Ser Ser Phe Asp Tyr
 1               5                  10

```
<210> SEQ ID NO 54
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 54

His Leu Gly Gly Thr Ala Cys Phe Asp Tyr
 1               5                  10

<210> SEQ ID NO 55
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 55

His Leu Gly Gly Thr Gly Ala Phe Asp Tyr
 1               5                  10

<210> SEQ ID NO 56
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 56

His Leu Gly Gly Thr Gly Ser Phe Asp Tyr
 1               5                  10

<210> SEQ ID NO 57
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 57

His Leu Gly Gly Thr Ser Thr Phe Asp Tyr
 1               5                  10

<210> SEQ ID NO 58
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 58

His Leu Gly Gly Thr Thr Ser Phe Asp Tyr
 1               5                  10

<210> SEQ ID NO 59
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 59

His Leu Gly Ser Thr Ala Ser Phe Asp Tyr
 1               5                  10

<210> SEQ ID NO 60
```

```
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 60

His Leu Tyr Arg Thr Ala Ser Phe Asp Tyr
 1               5                  10

<210> SEQ ID NO 61
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 61

His Met Gly Gly Thr Ala Ser Phe Asp Tyr
 1               5                  10

<210> SEQ ID NO 62
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 62

His Arg Gly Gly Thr Ala Ser Phe Asp Tyr
 1               5                  10

<210> SEQ ID NO 63
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 63

His Val Gly Gly Thr Ala Ser Phe Asp Tyr
 1               5                  10

<210> SEQ ID NO 64
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 64

His Trp Gly Gly Thr Ala Ser Phe Asp Tyr
 1               5                  10

<210> SEQ ID NO 65
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 65

His Tyr Gly Gly Thr Ala Ser Phe Asp Tyr
 1               5                  10

<210> SEQ ID NO 66
<211> LENGTH: 10
```

<212> TYPE: PRT
<213> ORGANISM: Artificial Sequence
<220> FEATURE:
<223> OTHER INFORMATION: Randomized sequence of CDRH3 of hz1E11

<400> SEQUENCE: 66

Met Asn Gly Gly Thr Ala Ser Phe Asp Tyr
 1               5                  10

<210> SEQ ID NO 67
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 67

Asn Phe Gly Gly Thr Ala Ser Phe Asp Tyr
 1               5                  10

<210> SEQ ID NO 68
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 68

Asn His Gly Gly Met Ala Ser Phe Asp Tyr
 1               5                  10

<210> SEQ ID NO 69
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 69

Asn His Gly Gly Thr Ala Ser Phe Asp Tyr
 1               5                  10

<210> SEQ ID NO 70
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 70

Asn Ile Gly Gly Thr Ala Ser Phe Asp Tyr
 1               5                  10

<210> SEQ ID NO 71
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 71

Asn Leu Gly Gly Thr Ala Ser Phe Asp Tyr
 1               5                  10

<210> SEQ ID NO 72
<211> LENGTH: 10
<212> TYPE: PRT

```
<213> ORGANISM: Artificial Sequence
<220> FEATURE:
<223> OTHER INFORMATION: Randomized sequence of CDRH3 of hz1E11

<400> SEQUENCE: 72

Asn Met Gly Gly Thr Ala Ser Phe Asp Tyr
 1               5                  10

<210> SEQ ID NO 73
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 73

Asn Asn Gly Gly Thr Ala Ser Phe Asp Tyr
 1               5                  10

<210> SEQ ID NO 74
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 74

Asn Trp Gly Gly Thr Ala Ser Phe Asp Tyr
 1               5                  10

<210> SEQ ID NO 75
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 75

Asn Tyr Gly Gly Ala Ala Ser Phe Asp Tyr
 1               5                  10

<210> SEQ ID NO 76
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 76

Asn Tyr Gly Gly Thr Ala Ser Phe Asp Tyr
 1               5                  10

<210> SEQ ID NO 77
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 77

Pro Leu Gly Gly Thr Ala Ser Phe Asp Tyr
 1               5                  10

<210> SEQ ID NO 78
<211> LENGTH: 10
<212> TYPE: PRT
<213> ORGANISM: Artificial Sequence
```

<220> FEATURE:
<223> OTHER INFORMATION: Randomized sequence of CDRH3 of hz1E11

<400> SEQUENCE: 78

Gln Leu Ala Gly Thr Ala Ser Phe Asp Tyr
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 79

Ser Phe Gly Gly Thr Ala Ser Phe Asp Tyr
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 80

Ser His Gly Gly Thr Ala Ser Phe Asp Tyr
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 81

Ser Leu Gly Gly Thr Ala Ser Phe Asp Tyr
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 82

Ser Met Gly Gly Thr Ala Ser Phe Asp Tyr
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 83

Ser Asn Gly Gly Thr Ala Ser Phe Asp Tyr
1               5                   10

<210> SEQ ID NO 84
<211> LENGTH: 10
<212> TYPE: PRT
<213> ORGANISM: Artificial Sequence
<220> FEATURE:

-continued

<223> OTHER INFORMATION: Randomized sequence of CDRH3 of hz1E11

<400> SEQUENCE: 84

Ser Trp Gly Gly Thr Ala Ser Phe Asp Tyr
 1               5                  10

<210> SEQ ID NO 85
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 85

Ser Tyr Gly Gly Thr Ala Ser Phe Asp Tyr
 1               5                  10

<210> SEQ ID NO 86
<211> LENGTH: 10
<212> TYPE: PRT
<213> ORGANISM: Artificial Sequence
<220> FEATURE:
<223> OTHER INFORMATION: Randomized sequence of CDRH3 of hz1E11

<400> SEQUENCE: 86

Tyr Tyr Gly Gly Thr Ala Ser Phe Asp Tyr
 1               5                  10

<210> SEQ ID NO 87
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 87

Asp Gln Leu Tyr Gly Thr Pro Trp Thr
 1               5

<210> SEQ ID NO 88
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 88

Asp Gln Met Tyr Ser Thr Pro Trp Thr
 1               5

<210> SEQ ID NO 89
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 89

His Gln Leu Ala Phe Thr Pro Trp Thr
 1               5

<210> SEQ ID NO 90
<211> LENGTH: 9
<212> TYPE: PRT
<213> ORGANISM: Artificial Sequence
<220> FEATURE:
<223> OTHER INFORMATION: Randomized sequence of CDRL3 of hz1E11

-continued

```
<400> SEQUENCE: 90

Leu Gln His Asn Glu Phe Pro Trp Thr
  1               5

<210> SEQ ID NO 91
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 91

Gln Asp Met Ser Arg Thr Pro Trp Thr
  1               5

<210> SEQ ID NO 92
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 92

Gln Glu Leu Ser Thr Thr Pro Trp Thr
  1               5

<210> SEQ ID NO 93
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 93

Gln Glu Met Met Arg Thr Pro Trp Thr
  1               5

<210> SEQ ID NO 94
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 94

Gln Asn Leu Ala Tyr Ser Pro Trp Thr
  1               5

<210> SEQ ID NO 95
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 95

Gln Asn Met Tyr Gly Thr Pro Trp Thr
  1               5

<210> SEQ ID NO 96
<211> LENGTH: 9
<212> TYPE: PRT
<213> ORGANISM: Artificial Sequence
<220> FEATURE:
<223> OTHER INFORMATION: Randomized sequence of CDRL3 of hz1E11
```

```
<400> SEQUENCE: 96

Gln Gln Ala Ala Phe Ser Pro Trp Thr
  1               5

<210> SEQ ID NO 97
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 97

Gln Gln Ala Ala Tyr Ser Pro Trp Thr
  1               5

<210> SEQ ID NO 98
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 98

Gln Gln Ala Ala Tyr Val Pro Trp Thr
  1               5

<210> SEQ ID NO 99
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 99

Gln Gln Cys Thr Ser Asp Pro Trp Thr
  1               5

<210> SEQ ID NO 100
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 100

Gln Gln His Asp Val Gly Pro Trp Thr
  1               5

<210> SEQ ID NO 101
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 101

Gln Gln Ile Ala Phe Gly Pro Trp Thr
  1               5

<210> SEQ ID NO 102
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 102
```

Gln Gln Ile Ala Phe Asn Pro Trp Thr
  1               5

<210> SEQ ID NO 103
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 103

Gln Gln Ile Ala Phe Ser Pro Trp Thr
  1               5

<210> SEQ ID NO 104
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 104

Gln Gln Ile Ala Phe Thr Pro Trp Thr
  1               5

<210> SEQ ID NO 105
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 105

Gln Gln Ile Ala Phe Val Pro Trp Thr
  1               5

<210> SEQ ID NO 106
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 106

Gln Gln Ile Ala Lys Thr Pro Trp Thr
  1               5

<210> SEQ ID NO 107
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 107

Gln Gln Ile Ala Tyr Ser Pro Trp Thr
  1               5

<210> SEQ ID NO 108
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 108

Gln Gln Ile Ala Tyr Thr Pro Trp Thr
1               5

<210> SEQ ID NO 109
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 109

Gln Gln Ile Ala Tyr Val Pro Trp Thr
1               5

<210> SEQ ID NO 110
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 110

Gln Gln Ile Phe Ser Val Pro Trp Thr
1               5

<210> SEQ ID NO 111
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 111

Gln Gln Ile Gly Phe Ser Pro Trp Thr
1               5

<210> SEQ ID NO 112
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 112

Gln Gln Ile Gly Trp Thr Pro Trp Thr
1               5

<210> SEQ ID NO 113
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 113

Gln Gln Ile Met Thr Leu Pro Trp Thr
1               5

<210> SEQ ID NO 114
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 114

Gln Gln Ile Arg Glu Ile Pro Trp Thr

```
1               5

<210> SEQ ID NO 115
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 115

Gln Gln Ile Ser Phe Met Pro Trp Thr
1               5

<210> SEQ ID NO 116
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 116

Gln Gln Ile Ser Phe Ser Pro Trp Thr
1               5

<210> SEQ ID NO 117
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 117

Gln Gln Ile Tyr Ile Thr Pro Trp Thr
1               5

<210> SEQ ID NO 118
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 118

Gln Gln Lys Ala Tyr Ala Pro Trp Thr
1               5

<210> SEQ ID NO 119
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 119

Gln Gln Lys Lys Gly Ile Pro Trp Thr
1               5

<210> SEQ ID NO 120
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 120

Gln Gln Lys Met Gly Asn Pro Trp Thr
1               5
```

<210> SEQ ID NO 121
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 121

Gln Gln Lys Ser Val Ala Pro Trp Thr
 1               5

<210> SEQ ID NO 122
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 122

Gln Gln Leu Ala Phe Ala Pro Trp Thr
 1               5

<210> SEQ ID NO 123
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 123

Gln Gln Leu Ala Phe Met Pro Trp Thr
 1               5

<210> SEQ ID NO 124
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 124

Gln Gln Leu Ala Phe Ser Pro Trp Thr
 1               5

<210> SEQ ID NO 125
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 125

Gln Gln Leu Ala Phe Val Pro Trp Thr
 1               5

<210> SEQ ID NO 126
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 126

Gln Gln Leu Ala Tyr Glu Pro Trp Thr
 1               5

<210> SEQ ID NO 127
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 127

Gln Gln Leu Ala Tyr Ser Pro Trp Thr
 1               5

<210> SEQ ID NO 128
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 128

Gln Gln Leu Ala Tyr Thr Pro Trp Thr
 1               5

<210> SEQ ID NO 129
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 129

Gln Gln Leu Ala Tyr Val Pro Trp Thr
 1               5

<210> SEQ ID NO 130
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 130

Gln Gln Leu Gly Phe Ala Pro Trp Thr
 1               5

<210> SEQ ID NO 131
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 131

Gln Gln Leu Gly Phe Ile Pro Trp Thr
 1               5

<210> SEQ ID NO 132
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 132

Gln Gln Leu Gly Phe Ser Pro Trp Thr
 1               5

-continued

<210> SEQ ID NO 133
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 133

Gln Gln Leu Gly Phe Val Pro Trp Thr
 1               5

<210> SEQ ID NO 134
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 134

Gln Gln Leu Gly Tyr Ala Pro Trp Thr
 1               5

<210> SEQ ID NO 135
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 135

Gln Gln Leu Gly Tyr Ser Pro Trp Thr
 1               5

<210> SEQ ID NO 136
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 136

Gln Gln Leu His Ser Thr Pro Trp Thr
 1               5

<210> SEQ ID NO 137
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 137

Gln Gln Leu Lys Asn Thr Pro Trp Thr
 1               5

<210> SEQ ID NO 138
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 138

Gln Gln Leu Met Arg Lys Pro Trp Thr
 1               5

<210> SEQ ID NO 139

```
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 139

Gln Gln Leu Arg Ala Ser Pro Trp Thr
 1               5

<210> SEQ ID NO 140
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 140

Gln Gln Leu Arg Asn Leu Pro Trp Thr
 1               5

<210> SEQ ID NO 141
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 141

Gln Gln Leu Arg Asn Ser Pro Trp Thr
 1               5

<210> SEQ ID NO 142
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 142

Gln Gln Leu Arg Asn Val Pro Trp Thr
 1               5

<210> SEQ ID NO 143
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 143

Gln Gln Leu Arg Ser Ala Pro Trp Thr
 1               5

<210> SEQ ID NO 144
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 144

Gln Gln Leu Arg Ser Ser Pro Trp Thr
 1               5

<210> SEQ ID NO 145
<211> LENGTH: 9
```

```
<212> TYPE: PRT
<213> ORGANISM: Artificial Sequence
<220> FEATURE:
<223> OTHER INFORMATION: Randomized sequence of CDRL3 of hz1E11

<400> SEQUENCE: 145

Gln Gln Leu Arg Ser Val Pro Trp Thr
 1               5

<210> SEQ ID NO 146
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 146

Gln Gln Leu Arg Val Ile Pro Trp Thr
 1               5

<210> SEQ ID NO 147
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 147

Gln Gln Leu Ser Phe Thr Pro Trp Thr
 1               5

<210> SEQ ID NO 148
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 148

Gln Gln Leu Ser Phe Val Pro Trp Thr
 1               5

<210> SEQ ID NO 149
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 149

Gln Gln Leu Ser Lys Thr Pro Trp Thr
 1               5

<210> SEQ ID NO 150
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 150

Gln Gln Leu Ser Arg Ala Pro Trp Thr
 1               5

<210> SEQ ID NO 151
<211> LENGTH: 9
<212> TYPE: PRT
```

```
<213> ORGANISM: Artificial Sequence
<220> FEATURE:
<223> OTHER INFORMATION: Randomized sequence of CDRL3 of hz1E11

<400> SEQUENCE: 151

Gln Gln Leu Ser Arg Ser Pro Trp Thr
 1               5

<210> SEQ ID NO 152
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 152

Gln Gln Leu Ser Val Thr Pro Trp Thr
 1               5

<210> SEQ ID NO 153
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 153

Gln Gln Leu Ser Tyr Ala Pro Trp Thr
 1               5

<210> SEQ ID NO 154
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 154

Gln Gln Leu Ser Tyr Ser Pro Trp Thr
 1               5

<210> SEQ ID NO 155
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 155

Gln Gln Leu Val Arg Ile Pro Trp Thr
 1               5

<210> SEQ ID NO 156
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 156

Gln Gln Leu Val Arg Asn Pro Trp Thr
 1               5

<210> SEQ ID NO 157
<211> LENGTH: 9
<212> TYPE: PRT
<213> ORGANISM: Artificial Sequence
```

```
<220> FEATURE:
<223> OTHER INFORMATION: Randomized sequence of CDRL3 of hz1E11

<400> SEQUENCE: 157

Gln Gln Leu Val Arg Thr Pro Trp Thr
 1               5

<210> SEQ ID NO 158
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 158

Gln Gln Leu Val Arg Val Pro Trp Thr
 1               5

<210> SEQ ID NO 159
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 159

Gln Gln Leu Tyr Ser Ser Pro Trp Thr
 1               5

<210> SEQ ID NO 160
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 160

Gln Gln Met Ala Phe Ala Pro Trp Thr
 1               5

<210> SEQ ID NO 161
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 161

Gln Gln Met Ala Phe Gly Pro Trp Thr
 1               5

<210> SEQ ID NO 162
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 162

Gln Gln Met Ala Phe Ile Pro Trp Thr
 1               5

<210> SEQ ID NO 163
<211> LENGTH: 9
<212> TYPE: PRT
<213> ORGANISM: Artificial Sequence
<220> FEATURE:
```

<223> OTHER INFORMATION: Randomized sequence of CDRL3 of hz1E11

<400> SEQUENCE: 163

Gln Gln Met Ala Phe Asn Pro Trp Thr
 1               5

<210> SEQ ID NO 164
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 164

Gln Gln Met Ala Phe Ser Pro Trp Thr
 1               5

<210> SEQ ID NO 165
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 165

Gln Gln Met Ala Phe Thr Pro Trp Thr
 1               5

<210> SEQ ID NO 166
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 166

Gln Gln Met Ala Phe Val Pro Trp Thr
 1               5

<210> SEQ ID NO 167
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 167

Gln Gln Met Ala Phe Tyr Pro Trp Thr
 1               5

<210> SEQ ID NO 168
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 168

Gln Gln Met Ala Gly Phe Pro Trp Thr
 1               5

<210> SEQ ID NO 169
<211> LENGTH: 9
<212> TYPE: PRT
<213> ORGANISM: Artificial Sequence
<220> FEATURE:
<223> OTHER INFORMATION: Randomized sequence of CDRL3 of hz1E11

```
<400> SEQUENCE: 169

Gln Gln Met Ala Ser Val Pro Trp Thr
 1               5

<210> SEQ ID NO 170
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 170

Gln Gln Met Ala Tyr Gly Pro Trp Thr
 1               5

<210> SEQ ID NO 171
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 171

Gln Gln Met Ala Tyr Ser Pro Trp Thr
 1               5

<210> SEQ ID NO 172
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 172

Gln Gln Met Ala Tyr Thr Pro Trp Thr
 1               5

<210> SEQ ID NO 173
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 173

Gln Gln Met Asp Phe Thr Pro Trp Thr
 1               5

<210> SEQ ID NO 174
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 174

Gln Gln Met Glu His Thr Pro Trp Thr
 1               5

<210> SEQ ID NO 175
<211> LENGTH: 9
<212> TYPE: PRT
<213> ORGANISM: Artificial Sequence
<220> FEATURE:
<223> OTHER INFORMATION: Randomized sequence of CDRL3 of hz1E11
```

```
<400> SEQUENCE: 175

Gln Gln Met Phe Ala Ile Pro Trp Thr
  1               5

<210> SEQ ID NO 176
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 176

Gln Gln Met Phe Gly Ser Pro Trp Thr
  1               5

<210> SEQ ID NO 177
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 177

Gln Gln Met Phe Arg Thr Pro Trp Thr
  1               5

<210> SEQ ID NO 178
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 178

Gln Gln Met Phe Ser Thr Pro Trp Thr
  1               5

<210> SEQ ID NO 179
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 179

Gln Gln Met Phe Ser Val Pro Trp Thr
  1               5

<210> SEQ ID NO 180
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 180

Gln Gln Met Gly Phe Ser Pro Trp Thr
  1               5

<210> SEQ ID NO 181
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 181
```

```
Gln Gln Met Gly Tyr Ala Pro Trp Thr
  1               5

<210> SEQ ID NO 182
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 182

Gln Gln Met Gly Tyr Ser Pro Trp Thr
  1               5

<210> SEQ ID NO 183
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 183

Gln Gln Met His Ile Phe Pro Trp Thr
  1               5

<210> SEQ ID NO 184
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 184

Gln Gln Met Met Ala Val Pro Trp Thr
  1               5

<210> SEQ ID NO 185
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 185

Gln Gln Met Met Lys Ser Pro Trp Thr
  1               5

<210> SEQ ID NO 186
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 186

Gln Gln Met Met Arg Thr Pro Trp Thr
  1               5

<210> SEQ ID NO 187
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 187
```

Gln Gln Met Met Arg Val Pro Trp Thr
1               5

<210> SEQ ID NO 188
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 188

Gln Gln Met Arg Lys Ile Pro Trp Thr
1               5

<210> SEQ ID NO 189
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 189

Gln Gln Met Arg Asn Val Pro Trp Thr
1               5

<210> SEQ ID NO 190
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 190

Gln Gln Met Arg Arg Val Pro Trp Thr
1               5

<210> SEQ ID NO 191
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 191

Gln Gln Met Arg Ser Thr Pro Trp Thr
1               5

<210> SEQ ID NO 192
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 192

Gln Gln Met Ser Phe Ser Pro Trp Thr
1               5

<210> SEQ ID NO 193
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 193

Gln Gln Met Ser His Ser Pro Trp Thr

```
                    1               5

<210> SEQ ID NO 194
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 194

Gln Gln Met Ser Lys Ile Pro Trp Thr
 1               5

<210> SEQ ID NO 195
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 195

Gln Gln Met Ser Arg Val Pro Trp Thr
 1               5

<210> SEQ ID NO 196
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 196

Gln Gln Met Ser Tyr Ala Pro Trp Thr
 1               5

<210> SEQ ID NO 197
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 197

Gln Gln Met Ser Tyr Gly Pro Trp Thr
 1               5

<210> SEQ ID NO 198
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 198

Gln Gln Met Ser Tyr Ile Pro Trp Thr
 1               5

<210> SEQ ID NO 199
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 199

Gln Gln Met Ser Tyr Ser Pro Trp Thr
 1               5
```

<210> SEQ ID NO 200
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 200

Gln Gln Met Ser Tyr Thr Pro Trp Thr
 1               5

<210> SEQ ID NO 201
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 201

Gln Gln Met Ser Tyr Val Pro Trp Thr
 1               5

<210> SEQ ID NO 202
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 202

Gln Gln Met Thr Arg Val Pro Trp Thr
 1               5

<210> SEQ ID NO 203
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 203

Gln Gln Met Val Ile Ile Pro Trp Thr
 1               5

<210> SEQ ID NO 204
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 204

Gln Gln Met Val Arg Glu Pro Trp Thr
 1               5

<210> SEQ ID NO 205
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 205

Gln Gln Met Val Arg Ser Pro Trp Thr
 1               5

```
<210> SEQ ID NO 206
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 206

Gln Gln Met Val Arg Thr Pro Trp Thr
 1               5

<210> SEQ ID NO 207
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 207

Gln Gln Met Val Arg Val Pro Trp Thr
 1               5

<210> SEQ ID NO 208
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 208

Gln Gln Met Val Ser Ile Pro Trp Thr
 1               5

<210> SEQ ID NO 209
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 209

Gln Gln Met Tyr Gly Thr Pro Trp Thr
 1               5

<210> SEQ ID NO 210
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 210

Gln Gln Met Tyr Lys Thr Pro Trp Thr
 1               5

<210> SEQ ID NO 211
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 211

Gln Gln Met Tyr Arg Thr Pro Trp Thr
 1               5
```

```
<210> SEQ ID NO 212
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 212

Gln Gln Asn Ala Phe Glu Pro Trp Thr
 1               5

<210> SEQ ID NO 213
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 213

Gln Gln Asn Ala Phe Gly Pro Trp Thr
 1               5

<210> SEQ ID NO 214
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 214

Gln Gln Asn Ala Phe Ile Pro Trp Thr
 1               5

<210> SEQ ID NO 215
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 215

Gln Gln Asn Ala Phe Ser Pro Trp Thr
 1               5

<210> SEQ ID NO 216
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 216

Gln Gln Asn Ala Phe Thr Pro Trp Thr
 1               5

<210> SEQ ID NO 217
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 217

Gln Gln Asn Ala Phe Val Pro Trp Thr
 1               5

<210> SEQ ID NO 218
```

```
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 218

Gln Gln Asn Ala Tyr Ala Pro Trp Thr
  1               5

<210> SEQ ID NO 219
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 219

Gln Gln Asn Ala Tyr Gly Pro Trp Thr
  1               5

<210> SEQ ID NO 220
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 220

Gln Gln Asn Ala Tyr Asn Pro Trp Thr
  1               5

<210> SEQ ID NO 221
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 221

Gln Gln Asn Ala Tyr Ser Pro Trp Thr
  1               5

<210> SEQ ID NO 222
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 222

Gln Gln Asn Phe Ile Ala Pro Trp Thr
  1               5

<210> SEQ ID NO 223
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 223

Gln Gln Asn Met Ile Val Pro Trp Thr
  1               5

<210> SEQ ID NO 224
<211> LENGTH: 9
```

<212> TYPE: PRT
<213> ORGANISM: Artificial Sequence
<220> FEATURE:
<223> OTHER INFORMATION: Randomized sequence of CDRL3 of hz1E11

<400> SEQUENCE: 224

Gln Gln Asn Arg Ile Ser Pro Trp Thr
 1               5

<210> SEQ ID NO 225
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 225

Gln Gln Asn Arg Ile Trp Pro Trp Thr
 1               5

<210> SEQ ID NO 226
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 226

Gln Gln Asn Arg Val Ile Pro Trp Thr
 1               5

<210> SEQ ID NO 227
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 227

Gln Gln Asn Arg Val Val Pro Trp Thr
 1               5

<210> SEQ ID NO 228
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 228

Gln Gln Asn Ser Tyr Ser Pro Trp Thr
 1               5

<210> SEQ ID NO 229
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 229

Gln Gln Asn Val Ile Val Pro Trp Thr
 1               5

<210> SEQ ID NO 230
<211> LENGTH: 9
<212> TYPE: PRT

<213> ORGANISM: Artificial Sequence
<220> FEATURE:
<223> OTHER INFORMATION: Randomized sequence of CDRL3 of hz1E11

<400> SEQUENCE: 230

Gln Gln Asn Val Asn Val Pro Trp Thr
1               5

<210> SEQ ID NO 231
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 231

Gln Gln Asn Tyr Lys Leu Pro Trp Thr
1               5

<210> SEQ ID NO 232
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 232

Gln Gln Ser Ala Phe Val Pro Trp Thr
1               5

<210> SEQ ID NO 233
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 233

Gln Gln Ser Ala Tyr Ala Pro Trp Thr
1               5

<210> SEQ ID NO 234
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 234

Gln Gln Ser Ala Tyr Ile Pro Trp Thr
1               5

<210> SEQ ID NO 235
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 235

Gln Gln Ser Glu Ala Cys Pro Trp Thr
1               5

<210> SEQ ID NO 236
<211> LENGTH: 9
<212> TYPE: PRT
<213> ORGANISM: Artificial Sequence

```
<220> FEATURE:
<223> OTHER INFORMATION: Randomized sequence of CDRL3 of hz1E11

<400> SEQUENCE: 236

Gln Gln Ser Phe Asn Thr Pro Trp Thr
1               5

<210> SEQ ID NO 237
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 237

Gln Gln Ser Lys Thr Val Pro Trp Thr
1               5

<210> SEQ ID NO 238
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 238

Gln Gln Thr Ala Phe Gly Pro Trp Thr
1               5

<210> SEQ ID NO 239
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 239

Gln Gln Thr Ala Phe Ser Pro Trp Thr
1               5

<210> SEQ ID NO 240
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 240

Gln Gln Thr Ala Tyr Ala Pro Trp Thr
1               5

<210> SEQ ID NO 241
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 241

Gln Gln Thr Ala Tyr Ser Pro Trp Thr
1               5

<210> SEQ ID NO 242
<211> LENGTH: 9
<212> TYPE: PRT
<213> ORGANISM: Artificial Sequence
<220> FEATURE:
```

<223> OTHER INFORMATION: Randomized sequence of CDRL3 of hz1E11

<400> SEQUENCE: 242

Gln Gln Thr Arg Arg Thr Pro Trp Thr
1               5

<210> SEQ ID NO 243
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 243

Gln Gln Thr Ser Phe Ala Pro Trp Thr
1               5

<210> SEQ ID NO 244
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 244

Gln Gln Val Ala Tyr Ser Pro Trp Thr
1               5

<210> SEQ ID NO 245
<211> LENGTH: 9
<212> TYPE: PRT
<213> ORGANISM: Artificial Sequence
<220> FEATURE:
<223> OTHER INFORMATION: Randomized sequence of CDRL3 of hz1E11

<400> SEQUENCE: 245

Gln Gln Val Phe Ala Ile Pro Trp Thr
1               5

<210> SEQ ID NO 246
<211> LENGTH: 321
<212> TYPE: DNA
<213> ORGANISM: Artificial Sequence
<220> FEATURE:
<223> OTHER INFORMATION: Nucleoide sequence of hz1E11-3 light chain
      variable region

<400> SEQUENCE: 246
gatatccaga tgacacaaag cccatcatct ttatctgcca gcgtgggaga tagagtgacc      60
atcacatgtc tggcatcaca gaccatcgga acttggttgg cctggtacca gcaaaaacca     120
ggcaaggccc ctaagctgct gatttacgtc gcaacgagtc tcgctgacgg tgtgccttcc     180 agatttccg gttccggcag cggcacagac tttactctga caattagttc cctgcagccc      240
gaggacttcg ctacttatta ctgcgaccag atgtacagca cgccctggac cttcgggcag     300
gggaccaaag ttgaaataaa g                                               321

<210> SEQ ID NO 247
<211> LENGTH: 107
<212> TYPE: PRT
<213> ORGANISM: Artificial Sequence
<220> FEATURE:
<223> OTHER INFORMATION: Amino acid sequence of hz1E11-3 light chain
      variable region

<400> SEQUENCE: 247

Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Thr Ile Gly Thr Trp
            20                  25                  30

Leu Ala Trp Tyr Gln Gln Lys Pro Gly Lys Ala Pro Lys Leu Leu Ile
        35                  40                  45

Tyr Val Ala Thr Ser Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Asp Gln Met Tyr Ser Thr Pro Trp
                85                  90                  95

Thr Phe Gly Gln Gly Thr Lys Val Glu Ile Lys
            100                 105

<210> SEQ ID NO 248
<211> LENGTH: 321
<212> TYPE: DNA
<213> ORGANISM: Artificial Sequence
<220> FEATURE:
<223> OTHER INFORMATION: Nucleoide sequence of hz1E11-133 light chain
      variable region

<400> SEQUENCE: 248
gatatccaga tgacacaaag cccatcatct ttatctgcca gcgtgggaga tagagtgacc      60
atcacatgtc tggcatcaca gaccatcgga acttggttgg cctggtacca gcaaaaacca    120
ggcaaggccc ctaagctgct gatttacgtc gcaacgagtc tcgctgacgg tgtgccttcc    180 agatttccg gttccggcag cggcacagac tttactctga caattagttc cctgcagccc     240
gaggacttcg ctactatta ctgccagcag aatgcttatg cgccctggac cttcgggcag     300
gggaccaaag ttgaaataaa g                                               321

<210> SEQ ID NO 249
<211> LENGTH: 107
<212> TYPE: PRT
<213> ORGANISM: Artificial Sequence
<220> FEATURE:
<223> OTHER INFORMATION: Amino acid sequence of hz1E11-133 light chain
      variable region

<400> SEQUENCE: 249

Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Thr Ile Gly Thr Trp
            20                  25                  30

Leu Ala Trp Tyr Gln Gln Lys Pro Gly Lys Ala Pro Lys Leu Leu Ile
        35                  40                  45

Tyr Val Ala Thr Ser Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Asn Ala Tyr Ala Pro Trp
                85                  90                  95

Thr Phe Gly Gln Gly Thr Lys Val Glu Ile Lys
            100                 105

<210> SEQ ID NO 250

```
<211> LENGTH: 321
<212> TYPE: DNA
<213> ORGANISM: Artificial Sequence
<220> FEATURE:
<223> OTHER INFORMATION: Nucleoide sequence of hz1E11-154 light chain
      variable region

<400> SEQUENCE: 250
gatatccaga tgacacaaag cccatcatct ttatctgcca gcgtgggaga tagagtgacc      60
atcacatgtc tggcatcaca gaccatcgga acttggttgg cctggtacca gcaaaaacca     120
ggcaaggccc ctaagctgct gatttacgtc gcaacgagtc tcgctgacgg tgtgccttcc     180
agattttccg gttccggcag cggcacagac tttactctga caattagttc cctgcagccc     240
gaggacttcg ctacttatta ctgccagcag acggcttttt ctccctggac cttcgggcag     300
gggaccaaag ttgaaataaa g                                                321

<210> SEQ ID NO 251
<211> LENGTH: 107
<212> TYPE: PRT
<213> ORGANISM: Artificial Sequence
<220> FEATURE:
<223> OTHER INFORMATION: Amino acid sequence of hz1E11-154 light chain
      variable region

<400> SEQUENCE: 251

Asp Ile Gln Met Thr Gln Ser Pro Ser Ser Leu Ser Ala Ser Val Gly
 1               5                  10                  15

Asp Arg Val Thr Ile Thr Cys Leu Ala Ser Gln Thr Ile Gly Thr Trp
            20                  25                  30

Leu Ala Trp Tyr Gln Gln Lys Pro Gly Lys Ala Pro Lys Leu Leu Ile
        35                  40                  45

Tyr Val Ala Thr Ser Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Ala Phe Ser Pro Trp
                85                  90                  95

Thr Phe Gly Gln Gly Thr Lys Val Glu Ile Lys
            100                 105

<210> SEQ ID NO 252
<211> LENGTH: 10
<212> TYPE: PRT
<213> ORGANISM: Artificial Sequence
<220> FEATURE:
<223> OTHER INFORMATION: CDRH3 of 1E11 antibody
<220> FEATURE:
<221> NAME/KEY: VARIANT
<222> LOCATION: (1)
<223> OTHER INFORMATION: Xaa is His, Asn, Ser or Ala
<220> FEATURE:
<221> NAME/KEY: VARIANT
<222> LOCATION: (2)
<223> OTHER INFORMATION: Xaa is Leu, Phe, Tyr, His, Met, Trp, Asn, Ile
      or Ala
<220> FEATURE:
<221> NAME/KEY: VARIANT
<222> LOCATION: (3)
<223> OTHER INFORMATION: Xaa is Gly or Cys
<220> FEATURE:
<221> NAME/KEY: VARIANT
<222> LOCATION: (4)
<223> OTHER INFORMATION: Xaa is Gly or Ser
<220> FEATURE:
<221> NAME/KEY: VARIANT
```

```
<222> LOCATION: (5)
<223> OTHER INFORMATION: Xaa is Thr, Met or Ala
<220> FEATURE:
<221> NAME/KEY: VARIANT
<222> LOCATION: (6)
<223> OTHER INFORMATION: Xaa is Ala, Ser, Gly or Thr
<220> FEATURE:
<221> NAME/KEY: VARIANT
<222> LOCATION: (7)
<223> OTHER INFORMATION: Xaa is Ser, Ala, Cys or Thr

<400> SEQUENCE: 252

Xaa Xaa Xaa Xaa Xaa Xaa Xaa Phe Asp Tyr
 1               5                  10

<210> SEQ ID NO 253
<211> LENGTH: 9
<212> TYPE: PRT
<213> ORGANISM: Artificial Sequence
<220> FEATURE:
<223> OTHER INFORMATION: CDRL3 of Formula 2
<220> FEATURE:
<221> NAME/KEY: VARIANT
<222> LOCATION: (1)
<223> OTHER INFORMATION: Xaa is Gln, Asp or Ala
<220> FEATURE:
<221> NAME/KEY: VARIANT
<222> LOCATION: (2)
<223> OTHER INFORMATION: Xaa is Gln, Asn, Glu or Ala
<220> FEATURE:
<221> NAME/KEY: VARIANT
<222> LOCATION: (3)
<223> OTHER INFORMATION: Xaa is Leu, Met, Asn, Ile, Ser, Thr, Ala or
      Lys
<220> FEATURE:
<221> NAME/KEY: VARIANT
<222> LOCATION: (4)
<223> OTHER INFORMATION: Xaa is Tyr, Ala, Ser, Arg, Val, Gly, Met or
      Phe
<220> FEATURE:
<221> NAME/KEY: VARIANT
<222> LOCATION: (5)
<223> OTHER INFORMATION: Xaa is Ser, Phe, Tyr, Arg, Ile, Gly, Lys,
      Asn, Val or Ala
<220> FEATURE:
<221> NAME/KEY: VARIANT
<222> LOCATION: (6)
<223> OTHER INFORMATION: Xaa is Thr, Ser, Val, Ile, Ala, Gly, Asn,
      Glu, Phe or Leu

<400> SEQUENCE: 253

Xaa Xaa Xaa Xaa Xaa Xaa Pro Trp Thr
 1               5
```